(12) United States Patent
Mazur et al.

(10) Patent No.: US 10,184,099 B2
(45) Date of Patent: Jan. 22, 2019

(54) FLEXIBLE BIOREACTOR AND SUPPORT STRUCTURE SYSTEM

(71) Applicant: Heliae Development, LLC, Gilbert, AZ (US)

(72) Inventors: Richard Mazur, Phoenix, AZ (US); Luke Cizek, Mesa, AZ (US); Mason Oelschlager, Gilbert, AZ (US); Mason McCarty, Scottsdale, AZ (US); Minh Duc Tram, Gilbert, AZ (US); Justin Hayden, Phoenix, AZ (US); Candyce Bair, Peoria, AZ (US)

(73) Assignee: Heliae Development LLC, Gilbert, AZ (US)

( * ) Notice: Subject to any disclaimer, the term of this patent is extended or adjusted under 35 U.S.C. 154(b) by 293 days.

(21) Appl. No.: 15/142,811

(22) Filed: Apr. 29, 2016

(65) Prior Publication Data

US 2016/0289620 A1    Oct. 6, 2016

Related U.S. Application Data

(63) Continuation of application No. PCT/US2016/025343, filed on Mar. 31, 2016, which
(Continued)

(51) Int. Cl.
*C12M 1/00*    (2006.01)
*C12M 3/00*    (2006.01)
(Continued)

(52) U.S. Cl.
CPC ............ *C12M 21/02* (2013.01); *C12M 23/14* (2013.01); *C12M 23/26* (2013.01); *C12M 23/34* (2013.01);
(Continued)

(58) Field of Classification Search
CPC ............ C12M 23/26; B01J 2219/00092; B01J 2219/00096; B01J 2219/0009
See application file for complete search history.

(56) References Cited

U.S. PATENT DOCUMENTS

| | | | |
|---|---|---|---|
| 4,236,349 A | 12/1980 | Ramus | |
| 4,654,240 A | 3/1987 | Johnston | |

(Continued)

FOREIGN PATENT DOCUMENTS

| | | |
|---|---|---|
| CA | 2801768 | 1/2013 |
| GB | 2202549 | 9/1988 |

(Continued)

OTHER PUBLICATIONS

Pulz, O., "Photobioreactors: Production Systems for Phototrophic Microorganisms," Applied Microbiology and Biotechnology, vol. 57, pp. 287-293 (Aug. 22, 2001).

(Continued)

*Primary Examiner* — Jonathan M Hurst
(74) *Attorney, Agent, or Firm* — Heliae Development LLC; Veronica-Adele R Cao; Justin Kniep

(57) ABSTRACT

Some embodiments include a system having a support structure configured to mechanically support a first bioreactor. The support structure can have a first frame and a second frame together being configured to mechanically support the first bioreactor in interposition between the first frame and the second frame. The first frame can maintain a first set point temperature of the first bioreactor through an exchange of thermal energy between the first frame and the first bioreactor when the first bioreactor is vitally supporting one or more first microorganisms and when the support structure is mechanically supporting the first bioreactor. Other embodiments of related systems and methods are also disclosed.

6 Claims, 12 Drawing Sheets

Related U.S. Application Data is a continuation-in-part of application No. 14/675,432, filed on Mar. 31, 2015, now abandoned.

(51) Int. Cl.
  *C12M 1/02* (2006.01)
  *C12M 1/34* (2006.01)
  *C12M 1/04* (2006.01)
  *C12M 1/12* (2006.01)

(52) U.S. Cl.
  CPC ............ *C12M 23/40* (2013.01); *C12M 23/48* (2013.01); *C12M 27/04* (2013.01); *C12M 29/04* (2013.01); *C12M 29/06* (2013.01); *C12M 31/00* (2013.01); *C12M 37/00* (2013.01); *C12M 41/22* (2013.01); *C12M 41/36* (2013.01); *C12M 41/40* (2013.01)

(56) References Cited

U.S. PATENT DOCUMENTS

| | | | |
|---|---|---|---|
| 5,565,015 | A | 10/1996 | Kobayashi |
| 5,686,304 | A | 11/1997 | Codner |
| 6,165,372 | A | 12/2000 | Ziemer et al. |
| 6,432,698 | B1 | 8/2002 | Gaugler et al. |
| 6,571,735 | B1 | 6/2003 | Wilkinson |
| 8,910,494 | B2 | 12/2014 | Kahlert |
| 2005/0239198 | A1 | 10/2005 | Kunas et al. |
| 2006/0013749 | A1* | 1/2006 | Arencibia, Jr. ........ B01F 7/1675 422/202 |
| 2006/0198763 | A1 | 9/2006 | Dang |
| 2006/0270036 | A1 | 11/2006 | Goodwin |
| 2007/0113474 | A1 | 5/2007 | Everett et al. |
| 2008/0139865 | A1 | 6/2008 | Galliher et al. |
| 2008/0153080 | A1 | 6/2008 | Woods et al. |
| 2008/0160591 | A1 | 7/2008 | Willson et al. |
| 2009/0180933 | A1 | 7/2009 | Kauling et al. |
| 2009/0305389 | A1 | 12/2009 | Willson et al. |
| 2010/0028990 | A1 | 2/2010 | Broadley et al. |
| 2010/0099170 | A1 | 4/2010 | Aswani |
| 2010/0255458 | A1 | 10/2010 | Kinkaid |
| 2011/0013474 | A1 | 1/2011 | Ludwig et al. |
| 2011/0104790 | A1 | 5/2011 | Kassebaum et al. |
| 2011/0281340 | A1 | 11/2011 | Turner et al. |
| 2013/0082410 | A1* | 4/2013 | Goodwin ............ B01F 15/0085 261/42 |
| 2013/0089925 | A1* | 4/2013 | Damren .................. C12M 41/24 435/303.3 |
| 2013/0244319 | A1 | 9/2013 | Dimitrelos |
| 2014/0113340 | A1 | 4/2014 | Harethi et al. |
| 2014/0134672 | A1 | 5/2014 | Tuttman et al. |
| 2014/0315290 | A1* | 10/2014 | Mottahedeh ........... C12M 21/02 435/288.7 |
| 2014/0322804 | A1 | 10/2014 | Boily et al. |
| 2015/0315538 | A1 | 11/2015 | Whitman et al. |
| 2015/0330903 | A1 | 11/2015 | Koeperick |

FOREIGN PATENT DOCUMENTS

| | | |
|---|---|---|
| JP | 2007282629 | 11/2007 |
| WO | 2005006838 | 1/2005 |
| WO | 2007025968 | 3/2007 |
| WO | 2007070452 | 6/2007 |
| WO | 2010076795 | 7/2010 |
| WO | 2011017171 | 2/2011 |

OTHER PUBLICATIONS

International Search Report and Written Opinion for PCT/US2016/025343, dated Sep. 22, 2016.
GE Healthcare Life Sciences, "ReadyCircuit bags and tubing assemblies," Data file 28-9606-44 AE, Nov. 2013.
Eibl et al., "Single-use Technology in Biopharmaceutical Production," Dechema Biotechnologie, www.dechema.de, 2nd Edition, Mar. 2012.
ATMI Life Sciences, Integrity PadReactor A New Culture in Cell Growth, www.atmi-lifesciences.com, 2010.
Results of the Partial International Search Report for PCT/US2016/025343, dated Jun. 6, 2016, 4 pages.
Ugwu, et al., "Photobioreactors for Mass Cultivation of Algae," Bioresource Technology, Jul. 2008 (available online Mar. 26, 2017), pp. 4021-4028, vol. 99, Institute of Life Sciences and Bioengineering, University of Tsukuba, 1-1-1 Tennodai, Tsukuba City, Ibaraki 305-8572, Japan.

* cited by examiner

FLEXIBLE BIOREACTOR AND SUPPORT STRUCTURE SYSTEM

CROSS-REFERENCE TO RELATED APPLICATIONS

This application is a continuation of International Patent Application No. PCT/US2016/025343, filed Mar. 31, 2016, and is a continuation-in-part of U.S. Non-Provisional patent application Ser. No. 14/675,432, filed Mar. 31, 2015. Meanwhile, International Patent Application No. PCT/US2016/025343 is a continuation-in-part of U.S. Non-Provisional patent application Ser. No. 14/675,432. International Patent Application No. PCT/US2016/025343 and U.S. Non-Provisional patent application Ser. No. 14/675,432 are incorporated by reference herein in their entirety.

FIELD OF THE INVENTION

This invention relates generally to systems for vitally supporting one or more organisms, and relates more particularly to such systems that permit for bioreactor sterilization, bioreactor mechanical support and temperature maintenance, and/or increased organism growth and methods of providing and using the same.

DESCRIPTION OF THE BACKGROUND

Worldwide traditional sources of protein, nutritional fatty acids, and petroleum oil are being depleted as the population and consumer demand increases. Algae (e.g., microalgae) is a renewable source with potential from traditional sources to produce biochemically active substances (e.g., lipids, proteins, polysaccharides) that can be used in whole cell and extract product forms to produce food, agricultural additives, nutritional supplements, cosmetics, specialty chemicals, and biofuels, as well as various other co-products (e.g., carotenoids, chlorophyll, phycocyanin, etc.) providing natural colorants and antioxidants. Algae also can be suitable as a replacement feedstock for traditional sources due to a variety of factors, including algae's high per-acre productivity compared to other terrestrial plants, algae's availability as a non-fish-based feedstock resources in places where the fish meal is becoming a scarce commodity, algae's ability to be grown on otherwise non-productive or non-arable land, and algae's ability to use a wide variety of water sources (fresh, brackish, saline, and wastewater). Realizing the potential for algae as a replacement resource can depend on the ability to culture the algae in reliable bioreactor systems capable of repeatedly producing high culture densities, high productivity rates, and high quality biomass (e.g., desirable profiles of biochemically active substances, low concentrations of contamination, etc.).

Accordingly, improved systems and methods for vitally supporting organisms (e.g., algae) able to produce biochemically active substances are desirable for their promise in satisfying future nutritional, agricultural, chemical, and energy needs in a clean, innocuous, sustainable, and/or cost effective manner.

BRIEF DESCRIPTION OF THE DRAWINGS

To facilitate further description of the embodiments, the following drawings are provided in which.

Figure 1:
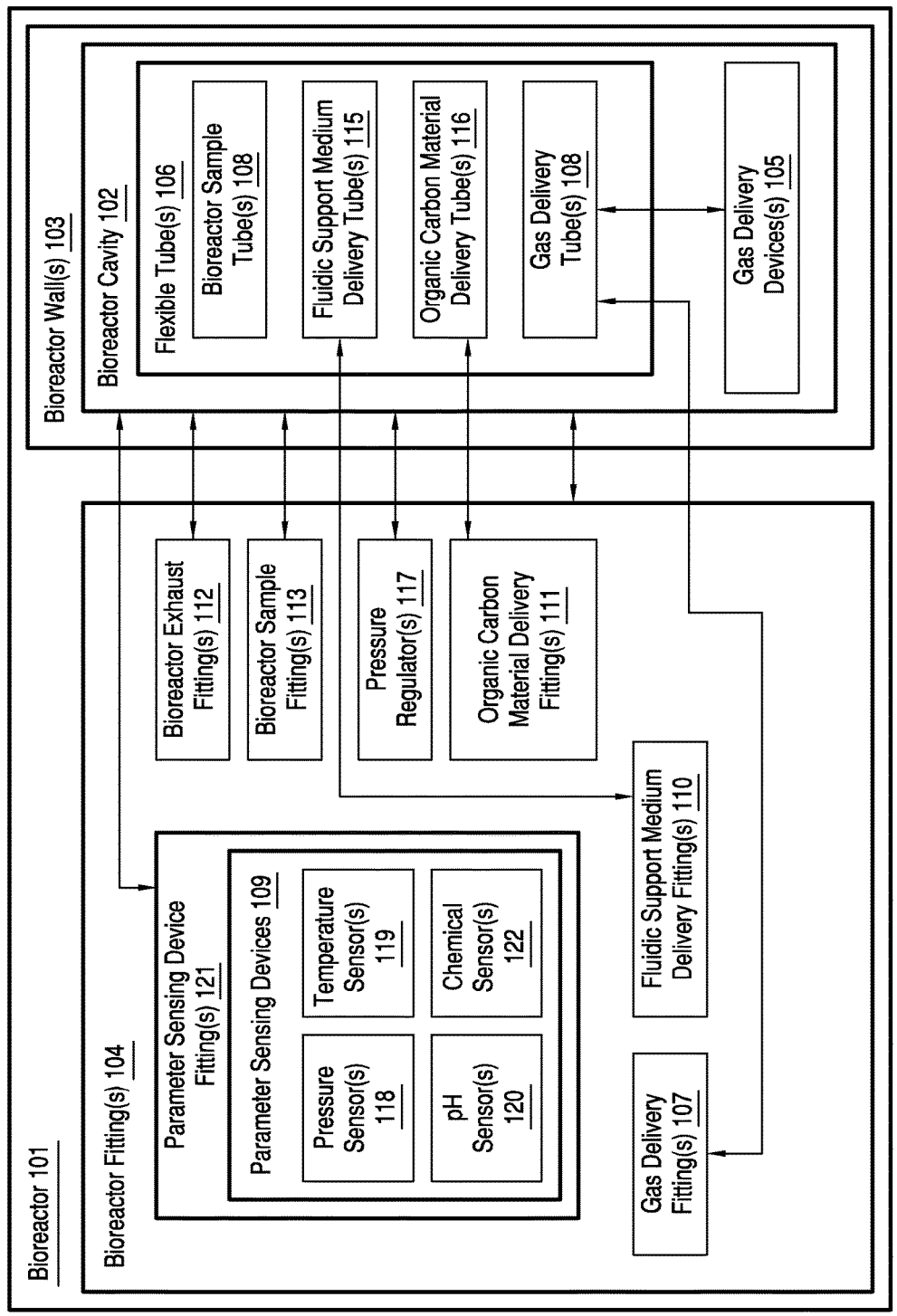
FIG. 1 illustrates an exemplary block diagram of a system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments include a system. The system comprises a bioreactor operable to vitally support one or more microorganisms and enclose the microorganism(s) and a fluidic support medium. The bioreactor can comprise a bioreactor cavity and one or more bioreactor walls at least partially forming the bioreactor cavity and comprising at least one bioreactor wall material. Further, the bioreactor can comprise one or more bioreactor fittings in communication with the bioreactor cavity, one or more gas delivery devices disposed within the bioreactor cavity, and one or more flexible tubes disposed within the bioreactor cavity. Further, the bioreactor fitting(s) can comprise at least one gas delivery fitting. Meanwhile, the gas delivery device(s) can be operable to inject gas into the bioreactor cavity to mix the microorganism(s), and the flexible tube(s) can comprise at least one gas delivery tube coupling the gas delivery device(s) to the gas delivery fitting(s). Further still, the bioreactor wall material(s) can be flexible, the bioreactor can be autoclaved one or more times to sterilize the bioreactor, and the bioreactor can be folded up and/or rolled up.

In these or other embodiments, the microorganism(s) can comprise at least one of microalgae or cyanobacteria, can comprise phototropic microorganisms, can comprise heterotrophic microorganisms, and/or can comprise mixotrophic microorganisms. In these or other embodiments, the bioreactor can comprise a photobioreactor, and the at least one bioreactor wall material can be at least partially transparent. Further, the bioreactor fitting(s) can comprise at least one organic carbon material delivery fitting operable to supply an organic carbon material to the microorganism(s). In these or other embodiments, the at least one bioreactor wall material comprises polypropylene and polyamide. In these or other embodiments, the bioreactor can comprise at least one parameter sensing device. In these or other embodiments, the gas delivery device(s) can be configured so that the gas injected by the gas delivery device(s) into the bioreactor cavity can comprise gas bubbles comprising a diameter greater than or equal to approximately 40 micrometers and less than or equal to approximately 2 millimeters and/or can comprise a volumetric flow rate of greater than or equal to approximately 10 liters per minute and less than or equal to approximately 120 liters per minute. In these or other embodiments, the gas delivery device(s) can comprise at least one sparger, the sparger(s) can comprise a sparger material, and the sparger material can comprise porous stainless steel or silicon. In these or other embodiments, the bioreactor fitting(s) can comprise a fluidic support medium delivery fitting operable to supply the microorganism(s) and the fluidic support medium to the bioreactor cavity, and the flexible tube(s) can comprise a fluidic support medium delivery tube operable to convey the microorganism(s) and the fluidic support medium at the bioreactor cavity. Further, the fluidic support medium delivery tube can comprise a fluidic support medium delivery tube input and a fluidic support medium delivery tube output, the fluidic support medium delivery tube input can be coupled to the fluidic support medium delivery fitting, and the fluidic support medium delivery tube output can comprise a non-planar cross section located within the bioreactor cavity. In these or other embodiments, at least one of the bioreactor fitting(s) can comprise a bioreactor fitting filter. In these or other embodiments, the bioreactor can comprise at least one pressure regulator operable to limit a bioreactor cavity pressure of the bioreactor cavity. In these or other embodiments, the bioreactor cavity can comprise at least one heat weld coupling together the one or more bioreactor walls. In these or other embodiments, the bioreactor is configured so that the bioreactor is able to be autoclaved to sterilize the bioreactor before the bioreactor vitally supports the microorganism(s). In these or other embodiments, the bioreactor can be operable to vitally support one or more first microorganisms of the microorganism(s) and one or more second microorganisms of the microorganism(s) at different times, and the bioreactor can be autoclaved to sterilize the bioreactor after the bioreactor vitally supports the first microorganism(s) and before the bioreactor vitally supports the second microorganism(s). In these or other embodiments, the bioreactor cavity can be substantially axenic when operating to vitally support the microorganism(s).

Some embodiments include a system. The system can comprise a bioreactor operable to vitally support one or more microorganisms. Meanwhile, the bioreactor can comprise a bioreactor cavity means for containing the microorganism(s) and a fluidic support medium, a parameter sensing means for monitoring a cavity environment condition at the bioreactor, and a bioreactor mixing means for mixing the microorganism(s). Further, the bioreactor can be autoclaved one or more times to sterilize the bioreactor, and the bioreactor can be folded up and/or rolled up.

In these or other embodiments, the microorganism(s) can comprise at least one of microalgae or cyanobacteria, can comprise phototropic microorganisms, can comprise heterotrophic microorganisms, and/or can comprise mixotrophic microorganisms. In these or other embodiments, the bioreactor can comprise an organic carbon material delivery means for supplying organic carbon material to the microorganism(s). In these or other embodiments, the bioreactor can comprise a pressure regulation means for limiting a bioreactor cavity pressure of the bioreactor cavity. In these or other embodiments, the bioreactor can comprise a filtration means for filtering a supply of at least one of a gas, one or more nutritional media, or the fluidic support medium. In these or other embodiments, the bioreactor is configured so that the bioreactor is able to be autoclaved to sterilize the bioreactor before the bioreactor vitally supports the microorganism(s). In these or other embodiments, the bioreactor can be operable to vitally support one or more first microorganisms of the microorganism(s) and one or more second microorganisms of the microorganism(s) at different times, and the bioreactor can be autoclaved to sterilize the bioreactor after the bioreactor vitally supports the first microorganism(s) and before the bioreactor vitally supports the second microorganism(s).

Some embodiments include a method. The method can comprise: providing one or more bioreactor walls of a bioreactor, the bioreactor wall(s) comprising at least one bioreactor wall material; providing one or more bioreactor fittings of the bioreactor, the bioreactor fitting(s) comprising at least one gas delivery fitting; providing one or more gas delivery devices of the bioreactor; providing one or more flexible tubes of the bioreactor, the flexible tube(s) comprising at least one gas delivery tube; coupling together the bioreactor wall(s) to at least partially form a bioreactor cavity of the bioreactor, the bioreactor cavity being configured to contain one or more microorganisms and a fluidic support medium; coupling the bioreactor fitting(s) to the bioreactor wall(s); coupling the gas delivery device(s) to the gas delivery fitting(s) with the gas delivery tube(s); and placing the gas delivery device(s) inside the bioreactor cavity. Meanwhile, the bioreactor can be operable to vitally support the microorganism(s), the bioreactor fitting(s) can communicate with the bioreactor cavity when the bioreactor fitting(s) are coupled to the bioreactor wall(s), and the gas delivery device(s) are operable to inject gas into the bioreactor cavity to mix the microorganism(s). Further, the at least one bioreactor wall material can be flexible, the bioreactor can be autoclaved one or more times to sterilize the bioreactor, and the bioreactor can folded up and/or rolled up.

In these or other embodiments, coupling together the bioreactor wall(s) to at least partially form a bioreactor cavity of the bioreactor comprises heat welding together the bioreactor wall(s) to at least partially form the bioreactor cavity of the bioreactor.

Some embodiments include a method. The method can comprise: sterilizing a bioreactor, wherein sterilizing the bioreactor comprises at least one of gamma irradiating the bioreactor or autoclaving the bioreactor; after sterilizing the bioreactor, vitally supporting one or more first microorganisms with the bioreactor; after vitally supporting the first microorganism(s) with the bioreactor, removing the first microorganism(s) from the bioreactor; after removing the first microorganism(s) from the bioreactor, gathering up the bioreactor, wherein gathering up the bioreactor after removing the first microorganism(s) from the bioreactor comprises at least one of folding the bioreactor after removing the first microorganism(s) from the bioreactor or rolling up the bioreactor after removing the first microorganism(s) from the bioreactor; after gathering up the bioreactor, resterilizing the bioreactor, wherein resterilizing the bioreactor comprises autoclaving the bioreactor; and after resterilizing the bioreactor, vitally supporting one or more second microorganisms with the bioreactor.

In these or other embodiments, the method can further comprise gathering up the bioreactor before sterilizing the bioreactor, wherein gathering up the bioreactor before sterilizing the bioreactor comprises at least one of folding the bioreactor before sterilizing the bioreactor or rolling up the bioreactor before sterilizing the bioreactor. In these or other embodiments, vitally supporting the first microorganism(s) can comprise illuminating the first microorganism(s) and/or supplying organic carbon material to the first microorganism(s). In these or other embodiments, vitally supporting the first microorganism(s) can comprise mixing the first microorganism(s) within a fluidic support medium by injecting gas into the fluidic support medium, wherein the gas can comprise gas bubbles comprising a diameter greater than or equal to approximately 40 micrometers and less than or equal to approximately 2 millimeters. In these or other embodiments, vitally supporting the first microorganism(s) with the bioreactor can comprise vitally supporting the first microorganism(s) with the bioreactor while the bioreactor cavity is substantially axenic, and vitally supporting the second microorganism(s) with the bioreactor comprises vitally supporting the second microorganism(s) with the bioreactor while the bioreactor cavity is substantially axenic.

Some embodiments include a system. The system can comprise a support structure operable to mechanically support a first bioreactor. The support structure can comprise a first frame and a second frame together being operable to mechanically support the first bioreactor in interposition between the first frame and the second frame. The first frame can maintain a first set point temperature of the first bioreactor when the first bioreactor is vitally supporting one or more first microorganisms and when the support structure is mechanically supporting the first bioreactor. Further, the first bioreactor can be operable to vitally support the first microorganism(s). Meanwhile, the first bioreactor can comprise a first bioreactor cavity configured to contain the first microorganism(s) and a first fluidic support medium, and can comprise one or more first bioreactor walls at least partially forming the first bioreactor cavity. Also, the first bioreactor wall(s) can comprise at least one first bioreactor wall material and the at least one first bioreactor wall material can be flexible.

In these or other embodiments, the system can comprise the first bioreactor, the first bioreactor can be autoclaved one or more times to sterilize the first bioreactor, and/or the first bioreactor can be folded up and/or rolled up. In these or other embodiments, the first bioreactor can comprise one or more bioreactor fittings in communication with the first bioreactor cavity, one or more gas delivery devices disposed within the first bioreactor cavity, and one or more flexible tubes disposed within the first bioreactor cavity. Further, the bioreactor fitting(s) can comprise at least one gas delivery fitting, the gas delivery device(s) can inject gas into the first bioreactor cavity to mix the first microorganism(s), and the flexible tube(s) can comprise at least one gas delivery tube coupling the gas delivery device(s) to the gas delivery fitting(s). In these or other embodiments, the first microorganism(s) can comprise at least one of microalgae or cyanobacteria, can comprise phototropic microorganisms, can comprise heterotrophic microorganisms, and/or can comprise mixotrophic microorganisms. In these or other embodiments, the second frame can maintain the first set point temperature of the first bioreactor when the first bioreactor is vitally supporting the first microorganism(s) and when the support structure is mechanically supporting the first bioreactor. In these or other embodiments, the first frame can comprise two or more first frame rails, each first frame rail of the two or more first frame rails can comprise a first frame rail conduit, each first frame rail conduit of the two or more first frame rail conduits can convey a temperature maintenance fluid to exchange thermal energy between the first bioreactor and the temperature maintenance fluid in order to maintain the first set point temperature of the first bioreactor when the first bioreactor is vitally supporting the first microorganism(s), and the two or more first frame rails can mechanically support the first bioreactor. In these or other embodiments, the two or more first frame rails can receive the temperature maintenance fluid in parallel. In these or other embodiments, the two or more first frame rails can comprise stainless steel, and the temperature maintenance fluid can comprise water. In these or other embodiments, the support structure can comprise a floor gap underneath one of the first frame or the second frame to permit the first bioreactor to bulge into the floor gap when the support structure is mechanically supporting the first bioreactor. In these or other embodiments, the system can further comprise at least one light source mechanically supported by the support structure and operable to illuminate the first microorganism(s) when the first bioreactor is vitally supporting the first microorganism(s) and when the support structure is mechanically supporting the first bioreactor.

In these or other embodiments, the support structure can mechanically support a second bioreactor. The support structure can comprise a third frame and a fourth frame together being operable to mechanically support the second bioreactor in interposition between the third frame and the fourth frame, the third frame can maintain a second set point temperature of the second bioreactor when the second bioreactor is vitally supporting one or more second microorganisms and when the support structure is mechanically supporting the second bioreactor, and the second bioreactor can vitally support the second microorganism(s). Meanwhile, the second bioreactor can comprise a second bioreactor cavity configured to contain the second microorganism(s) and a second fluidic support medium, and can comprise one or more second bioreactor walls at least partially forming the second bioreactor cavity. Further, the second bioreactor wall(s) can comprise at least one second bioreactor wall material and the at least one second bioreactor wall material can be flexible. In these or other embodiments, the first set point temperature of the first bioreactor can be approximately equal to the second set point temperature of the second bioreactor. In these or other embodiments, the first microorganism(s) can comprise the second microorganism(s).

Some embodiments include a system. The system comprises a support means for mechanically supporting a first bioreactor and maintaining a first set point temperature of the first bioreactor when the first bioreactor is vitally supporting one or more first microorganisms and when the support means is mechanically supporting the first bioreactor. The first bioreactor can be operable to vitally support the first microorganism(s). Further, the first bioreactor can comprise a first bioreactor cavity configured to contain the first microorganism(s) and a first fluidic support medium, and can comprise one or more first bioreactor walls at least partially forming the first bioreactor cavity. Also, the first bioreactor wall(s) can comprise at least one first bioreactor wall material and the at least one first bioreactor wall material can be flexible.

In these or other embodiments, the support means can further be for mechanically supporting a second bioreactor and maintaining a second set point temperature of the second bioreactor when the second bioreactor is vitally supporting one or more second microorganisms and when the support means is mechanically supporting the second bioreactor. Further, the second bioreactor can vitally support the second microorganism(s). Meanwhile, the second bioreactor can comprise a second bioreactor cavity configured to contain the second microorganism(s) and a second fluidic support medium, and can comprise one or more second bioreactor walls at least partially forming the second bioreactor cavity. Also, the second bioreactor wall(s) can comprise at least one second bioreactor wall material and the at least one second bioreactor wall material can be flexible.

Some embodiments include a method. The method can comprise providing a support structure operable to mechanically support a first bioreactor operable to vitally support one or more first microorganisms. Meanwhile, providing the support structure can comprise: providing a first frame; providing a second frame; and configuring the first frame and the second frame such that the first frame and the second frame together are operable to mechanically support the first bioreactor in interposition between the first frame and the second frame. Further, the first frame can maintain a first set point temperature of the first bioreactor when the first bioreactor is vitally supporting the first microorganism(s) and when the support structure is mechanically supporting the first bioreactor. Further still, the first bioreactor can comprise a first bioreactor cavity configured to contain the first microorganism(s) and a first fluidic support medium, and can comprise one or more first bioreactor walls at least partially forming the first bioreactor cavity. Also, the one or more first bioreactor walls can comprise at least one first bioreactor wall material and the at least one first bioreactor wall material can be flexible.

In these or other embodiments, the method can comprise providing the first bioreactor, and interposing the first bioreactor between the first frame and the second frame. In these or other embodiments, providing the first frame can comprise providing two or more first frame rails. Further, each first frame rail of the two or more first frame rails can comprise a first frame rail conduit, each first frame rail conduit of the two or more first frame rail conduits can convey a temperature maintenance fluid to exchange thermal energy between the first bioreactor and the temperature maintenance fluid in order to maintain the first set point temperature of the first bioreactor when the first bioreactor is vitally supporting the first microorganism(s), and the two or more first frame rails can mechanically support the first bioreactor. In these or other embodiments, the method can comprise providing the temperature maintenance fluid to the first frame rail conduit of the two or more first frame rails.

Some embodiments can include a method. The method can comprise: vitally supporting one or more first microorganisms at a first bioreactor, the first bioreactor comprising (i) a first bioreactor cavity configured to contain the first microorganism(s) and a first fluidic support medium and (ii) one or more first bioreactor walls at least partially forming the first bioreactor cavity, the one or more first bioreactor walls comprising at least one first bioreactor wall material, and the at least one first bioreactor wall material being flexible; mechanically supporting the first bioreactor between a first frame and a second frame of a support structure; and supplying a temperature maintenance fluid to the first frame to maintain a first set point temperature of the first bioreactor while vitally supporting the first microorganism(s) at the first bioreactor and while mechanically supporting the first bioreactor between the first frame and the second frame of the support structure.

In these or other embodiments, the method can comprise supplying the temperature maintenance fluid to the second frame to maintain the first set point temperature of the first bioreactor while vitally supporting the first microorganism(s) at the first bioreactor and while mechanically supporting the first bioreactor between the first frame and the second frame of the support structure. In these or other embodiments, the method can further comprise: vitally supporting one or more second microorganisms at a second bioreactor, the second bioreactor comprising (i) a second bioreactor cavity configured to contain the second microorganism(s) and a second fluidic support medium and (ii) one or more second bioreactor walls at least partially forming the second bioreactor cavity, the one or more second bioreactor walls comprising at least one second bioreactor wall material, and the at least one second bioreactor wall material being flexible; mechanically supporting the second bioreactor between a third frame and a fourth frame of the support structure; and supplying the temperature maintenance fluid to the third frame to maintain a second set point temperature of the second bioreactor while vitally supporting the second microorganism(s) at the second bioreactor and while mechanically supporting the second bioreactor between the third frame and the fourth frame of the support structure.

Some embodiments can include a system. The system can comprise a bioreactor operable to vitally support one or more microorganisms. Further, the bioreactor can comprise a bioreactor cavity configured to contain the microorganism(s) and a fluidic support medium, and can comprise one or more bioreactor walls at least partially forming the bioreactor cavity. Also, the bioreactor wall(s) comprising at least one bioreactor wall material. Meanwhile, the at least one bioreactor wall material can be flexible, and the bioreactor can be configured to be folded up and/or rolled up.

In these or other embodiments, at least one of (a) when the microorganism(s) are taxonomically classified in taxonomic family Haematococcaceae, the bioreactor can vitally support the microorganism(s) such that an average density of the microorganism(s) is greater than or equal to approximately 12 grams per liter and/or an average maximum production rate of the microorganism(s) is greater than or equal to approximately 2.5 grams per liter per day; (b) when the microorganism(s) are taxonomically classified in taxonomic family Chlorellaceae, and the bioreactor can vitally support the microorganism(s) such that an average density of the microorganism(s) is greater than or equal to approximately 36 grams per liter, and/or an average maximum production rate of the microorganism(s) is greater than or equal to approximately 9 grams per liter per day; and/or (c) when the microorganism(s) are taxonomically classified in taxonomic family Chlamydomonadaceae, the bioreactor can vitally support the microorganism(s) such that an average density of the microorganism(s) is greater than or equal to approximately 7 grams per liter and/or an average maximum production rate of the microorganism(s) is greater than or equal to approximately 3 grams per liter per day.

In these or other embodiments, the bioreactor can be autoclaved one or more times to sterilize the bioreactor. In these or other embodiments, the bioreactor can comprise one or more bioreactor fittings in communication with the bioreactor cavity, one or more gas delivery devices disposed within the bioreactor cavity, and one or more flexible tubes disposed within the bioreactor cavity. Further, the bioreactor fitting(s) can comprise at least one gas delivery fitting, the gas delivery device(s) can inject gas into the first bioreactor cavity to mix the microorganism(s), and the flexible tube(s) can comprise at least one gas delivery tube coupling the gas delivery device(s) to the gas delivery fitting(s).

In these or other embodiments, the one or more gas delivery devices can be configured so that the gas injected by the gas delivery device(s) into the bioreactor comprises gas bubbles comprising a diameter greater than or equal to approximately 40 micrometers and less than or equal to approximately 2 millimeters and/or a volumetric flow rate of greater than or equal to approximately 10 liters per minute and less than or equal to approximately 120 liters per minute.

In these or other embodiments, the bioreactor can comprise a photobioreactor and the at least one bioreactor wall material can be at least partially transparent, and/or the bioreactor can comprise one or more bioreactor fittings in communication with the bioreactor cavity. Further, the bioreactor fitting(s) can comprise at least one organic carbon material delivery fitting operable to supply organic carbon material to the microorganism(s). In these or other embodiments, the at least one bioreactor wall material can comprise polypropylene and polyamide. In these or other embodiments, the bioreactor cavity can be substantially axenic when operating to vitally support the microorganism(s). In these or other embodiments, the bioreactor cavity can comprise a volume greater than or equal to approximately 18.92 liters.

In these or other embodiments, the system can further comprise a support structure operable to mechanically support the first bioreactor. Further, the support structure can comprise a first frame and a second frame together being operable to mechanically support the first bioreactor in interposition between the first frame and the second frame, and the first frame can maintain a first set point temperature of the first bioreactor when the first bioreactor is vitally supporting the first microorganism(s) and when the support structure is mechanically supporting the first bioreactor. In these or other embodiments, the second frame can maintain the first set point temperature of the first bioreactor when the first bioreactor is vitally supporting the first microorganism(s) and when the support structure is mechanically supporting the first bioreactor. In these or other embodiments, the first frame can comprise two or more first frame rails, each first frame rail of the two or more first frame rails can comprise a first frame rail conduit, each first frame rail conduit of the two or more first frame rail conduits can convey a temperature maintenance fluid to exchange thermal energy between the first bioreactor and the temperature maintenance fluid in order to maintain the first set point temperature of the first bioreactor when the first bioreactor is vitally supporting the first microorganism(s), and the two or more first frame rails can mechanically support the first bioreactor. In these or other embodiments, the two or more first frame rails can receive the temperature maintenance fluid in parallel.

Some embodiments include a system. The system can comprise a bioreactor operable to vitally support one or more microorganisms. Further, the bioreactor can comprise a bioreactor cavity means for containing the microorganism(s) and a fluidic support medium. In these or other embodiments, at least one of (a) when the microorganism(s) are taxonomically classified in taxonomic family Haematococcaceae, the bioreactor can vitally support the microorganism(s) such that an average density of the microorganism(s) is greater than or equal to approximately 12 grams per liter and/or an average maximum production rate of the microorganism(s) is greater than or equal to approximately 2.5 grams per liter per day; (b) when the microorganism(s) are taxonomically classified in taxonomic family Chlorellaceae, and the bioreactor can vitally support the microorganism(s) such that an average density of the microorganism(s) is greater than or equal to approximately 36 grams per liter, and/or an average maximum production rate of the microorganism(s) is greater than or equal to approximately 9 grams per liter per day; and/or (c) when the microorganism(s) are taxonomically classified in taxonomic family Chlamydomonadaceae, the bioreactor can vitally support the microorganism(s) such that an average density of the microorganism(s) is greater than or equal to approximately 7 grams per liter and/or an average maximum production rate of the microorganism(s) is greater than or equal to approximately 3 grams per liter per day.

Some embodiments include a method. The method can comprise providing a bioreactor operable to vitally support one or more microorganisms. Further, providing the bioreactor can comprise: providing one or more bioreactor walls, the bioreactor wall(s) comprising at least one bioreactor wall material and the at least one bioreactor wall material being flexible; and coupling together the bioreactor wall(s) so that the bioreactor wall(s) at least partially form a bioreactor cavity configured to contain the microorganism(s) and a fluidic support medium. In these or other embodiments, at least one of (a) when the microorganism(s) are taxonomically classified in taxonomic family Haematococcaceae, the bioreactor can vitally support the microorganism(s) such that an average density of the microorganism(s) is greater than or equal to approximately 12 grams per liter and/or an average maximum production rate of the microorganism(s) is greater than or equal to approximately 2.5 grams per liter per day; (b) when the microorganism(s) are taxonomically classified in taxonomic family Chlorellaceae, and the bioreactor can vitally support the microorganism(s) such that an average density of the microorganism(s) is greater than or equal to approximately 36 grams per liter, and/or an average maximum production rate of the microorganism(s) is greater than or equal to approximately 9 grams per liter per day; and/or (c) when the microorganism(s) are taxonomically classified in taxonomic family Chlamydomonadaceae, the bioreactor can vitally support the microorganism(s) such that an average density of the microorganism(s) is greater than or equal to approximately 7 grams per liter and/or an average maximum production rate of the microorganism(s) is greater than or equal to approximately 3 grams per liter per day.

In these or other embodiments, coupling together the bioreactor wall(s) so that the bioreactor wall(s) at least partially form the bioreactor cavity can comprise bonding together by heat welding the bioreactor wall(s) so that the bioreactor wall(s) at least partially form the bioreactor cavity. Further, the at least one bioreactor wall material can comprise a polymer material.

Some embodiments include a method. The method can comprise: inoculating a bioreactor with one or more first microorganisms and a first fluidic support medium, the bioreactor comprising one or more bioreactor walls at least partially forming a bioreactor cavity, the bioreactor being configured to be at least one of folded up or rolled up, the bioreactor wall(s) comprising at least one bioreactor wall material, and the at least one bioreactor wall material being flexible; and vitally supporting the first microorganism(s) with the bioreactor such that: (a) when the microorganism(s) are taxonomically classified in taxonomic family Haematococcaceae, the bioreactor can vitally support the microorganism(s) such that an average density of the microorganism(s) is greater than or equal to approximately 12 grams per liter and/or an average maximum production rate of the microorganism(s) is greater than or equal to approximately 2.5 grams per liter per day; (b) when the microorganism(s) are taxonomically classified in taxonomic family Chlorellaceae, and the bioreactor can vitally support the microorganism(s) such that an average density of the microorganism(s) is greater than or equal to approximately 36 grams per liter, and/or an average maximum production rate of the microorganism(s) is greater than or equal to approximately 9 grams per liter per day; and/or (c) when the microorganism(s) are taxonomically classified in taxonomic family Chlamydomonadaceae, the bioreactor can vitally support the microorganism(s) such that an average density of the microorganism(s) is greater than or equal to approximately 7 grams per liter and/or an average maximum production rate of the microorganism(s) is greater than or equal to approximately 3 grams per liter per day.

In these or other embodiments, the method can further comprise: after vitally supporting the first microorganism(s), autoclaving the bioreactor; after autoclaving the bioreactor, inoculating the bioreactor with one or more second microorganisms; and after inoculating the bioreactor with the second microorganism(s), vitally supporting the second microorganism(s) with the bioreactor.

In these or other embodiments, the method can further comprise: mechanically supporting the bioreactor with a support structure comprising a first frame and a second frame together being operable to mechanically support the bioreactor in interposition between the first frame and the second frame; and supplying a temperature maintenance fluid to the first frame to maintain a set point temperature of the bioreactor while vitally supporting the first microorganism(s) and while mechanically supporting the bioreactor with the support structure.

Some embodiments include a system. The system can comprise a bioreactor operable to vitally support one or more microorganisms and enclose the one or more microorganisms and a fluidic support medium. Meanwhile, the bioreactor can comprise a bioreactor cavity, one or more bioreactor walls at least partially forming the bioreactor cavity and comprising at least one bioreactor wall material, one or more bioreactor fittings in communication with the bioreactor cavity, one or more gas delivery devices disposed within the bioreactor cavity, one or more flexible tubes disposed within the bioreactor cavity, and at least one parameter sensing device. The one or more bioreactor fittings can comprise at least one gas delivery fitting, the one or more gas delivery devices can be operable to inject gas into the bioreactor cavity to mix the one or more microorganisms, and/or the one or more flexible tubes can comprise at least one gas delivery tube coupling the one or more gas delivery devices to the at least one gas delivery fitting. Further, the at least one bioreactor wall material can be flexible. Further still, while the bioreactor is assembled to include the one or more bioreactor fittings, the one or more gas delivery devices, the one or more flexible tubes, and the at least one parameter sensing device, the bioreactor can be configured so that the bioreactor, as assembled, is able to be autoclaved one or more times to sterilize the bioreactor; and while the bioreactor is assembled to include the one or more bioreactor fittings, the one or more gas delivery devices, the one or more flexible tubes, and the at least one parameter sensing device, the bioreactor, as assembled, is configured to be at least one of folded up or rolled up.

Some embodiments include a system. The system can comprise a bioreactor operable to vitally support one or more microorganisms. Meanwhile, the bioreactor can comprise a bioreactor cavity means for containing the one or more microorganisms and a fluidic support medium, a parameter sensing means for monitoring a cavity environment condition at the bioreactor, and a bioreactor mixing means for mixing the one or more microorganisms. Further, while the bioreactor is assembled to include the bioreactor cavity means, the parameter sensing means, and the bioreactor mixing means, the bioreactor, as assembled, is configured to be at least one of folded up or rolled up; and while the bioreactor is assembled to include the bioreactor cavity means, the parameter sensing means, and the bioreactor mixing means, and while the bioreactor, as assembled, is at least one of folded up or rolled up, the bioreactor is configured so that the bioreactor, as assembled, is able to be autoclaved one or more times to sterilize the bioreactor.

Some embodiments include a system. The system can comprise a support structure configured to mechanically support a first bioreactor. Meanwhile, the support structure can comprise a first frame and a second frame, together with the first frame, being configured to mechanically support the first bioreactor in interposition between the first frame and the second frame. The first frame can be configured to maintain a first set point temperature of the first bioreactor through an exchange of thermal energy between the first frame and the first bioreactor when the first bioreactor is vitally supporting one or more first microorganisms and when the support structure is mechanically supporting the first bioreactor. Further, the first bioreactor can comprise a first bioreactor cavity configured to contain the one or more first microorganisms and a first fluidic support medium, and one or more first bioreactor walls at least partially enclosing the first bioreactor cavity. The one or more first bioreactor walls can comprise at least one first bioreactor wall material, and the at least one first bioreactor wall material can be flexible.

Some embodiments include a system. The system can comprise a support means configured to mechanically support a first bioreactor and maintain a first set point temperature of the first bioreactor through an exchange of thermal energy between the support means and the first bioreactor when the first bioreactor is vitally supporting one or more first microorganisms and when the support means is mechanically supporting the first bioreactor. Meanwhile, the first bioreactor can comprise a first bioreactor cavity configured to contain the one or more first microorganisms and a first fluidic support medium, and one or more first bioreactor walls at least partially enclosing the first bioreactor cavity. The one or more first bioreactor walls can comprise at least one first bioreactor wall material, and the at least one first bioreactor wall material can be flexible.

Some embodiments include a system. The system can comprise a support structure configured to mechanically support a first bioreactor. Meanwhile, the support structure can comprise a first frame and a second frame, together with the first frame, being configured to mechanically support the first bioreactor in interposition between the first frame and the second frame. The first frame can be configured to maintain a first set point temperature of the first bioreactor through an exchange of thermal energy between the first frame and the first bioreactor when the first bioreactor is vitally supporting one or more first microorganisms and when the support structure is mechanically supporting the first bioreactor. Further, the second frame can be configured to maintain the first set point temperature of the first bioreactor through an exchange of thermal energy between the second frame and the first bioreactor when the first bioreactor is vitally supporting the one or more first microorganisms and when the support structure is mechanically supporting the first bioreactor. Also, the first bioreactor can comprise a first bioreactor cavity configured to contain the one or more first microorganisms and a first fluidic support medium, and one or more first bioreactor walls at least partially enclosing the first bioreactor cavity. The one or more first bioreactor walls can comprise at least one first bioreactor wall material, and the at least one first bioreactor wall material can be flexible. Further, the first frame can comprise two or more first frame rails, and each first frame rail of the two or more first frame rails can comprise a first frame rail conduit. Meanwhile, each first frame rail conduit of the two or more first frame rail conduits can be configured to convey a temperature maintenance fluid to exchange first thermal energy between the first bioreactor and the temperature maintenance fluid in order to maintain the first set point temperature of the first bioreactor when the first bioreactor is vitally supporting the one or more first microorganisms, and the two or more first frame rails can be operable to mechanically support the first bioreactor.

Some embodiments include a method. The method can comprise: providing one or more bioreactor walls of a bioreactor, the one or more bioreactor walls comprising at least one bioreactor wall material; providing one or more bioreactor fittings of the bioreactor, the one or more bioreactor fittings comprising at least one gas delivery fitting; providing one or more gas delivery devices of the bioreactor; providing one or more flexible tubes of the bioreactor, the one or more flexible tubes comprising at least one gas delivery tube; providing at least one parameter sensing device; and assembling the bioreactor. Further, assembling the bioreactor can comprise: coupling together the one or more bioreactor walls to at least partially form a bioreactor cavity of the bioreactor, the bioreactor cavity being configured to contain one or more microorganisms and a fluidic support medium; coupling the one or more bioreactor fittings to the one or more bioreactor walls; coupling the one or more gas delivery devices to the at least one gas delivery fitting with the at least one gas delivery tube; placing the one or more gas delivery devices inside the bioreactor cavity while the one or more gas delivery devices are coupled to the at least one gas delivery fitting by the at least one gas delivery tube; and placing the at least one parameter sensing device in at least one bioreactor fitting of the one or more bioreactor fittings. Meanwhile, when the bioreactor is assembled, the bioreactor can be operable to vitally support the one or more microorganisms. Further, the one or more bioreactor fittings can communicate with the bioreactor cavity when the bioreactor fittings are coupled to the one or more bioreactor walls and when the one or more bioreactor walls are coupled together, the one or more gas delivery devices can be operable to inject gas into the bioreactor cavity to mix the one or more microorganisms, and the at least one bioreactor wall material can be flexible. Further still, while the bioreactor is assembled to include the one or more bioreactor fittings, the one or more gas delivery devices, the one or more flexible tubes, and the at least one parameter sensing device, the bioreactor can be configured so that the bioreactor, as assembled, is able to be autoclaved one or more times to sterilize the bioreactor; and while the bioreactor is assembled to include the one or more bioreactor fittings, the one or more gas delivery devices, the one or more flexible tubes, and the at least one parameter sensing device, the bioreactor, as assembled, can be configured to be at least one of folded up or rolled up.

In these or other embodiments, providing the one or more bioreactor fittings of the bioreactor can comprise providing a pressure regulation device for limiting a bioreactor cavity pressure of the bioreactor cavity. Further, providing the one or more bioreactor fittings of the bioreactor can comprise providing a filter for filtering a supply of at least one of a gas, one or more nutritional media, or the fluidic support medium.

Some embodiments include a method of culturing one or more microalgae. The method can comprise: inoculating a bioreactor with the one or more microalgae and a fluidic support medium, the bioreactor comprising one or more bioreactor walls at least partially enclosing a bioreactor cavity, being configured to be at least one of folded up or rolled up, and being sterile when the bioreactor is inoculated with the one or more microalgae, the one or more bioreactor walls comprising at least one bioreactor wall material, the at least one bioreactor wall material being flexible and at least partially transparent; and vitally supporting the one or more microalgae. Meanwhile, vitally supporting the one or more microalgae can comprise: supplying the one or more microalgae with an organic carbon material; supplying the one or more microalgae with a quantity of light based on the culture density; and supplying one or more nutritional media to the one or more microalgae when a culture density of the one or more microalgae reaches a threshold culture density.

Some embodiments include a method. The method can comprise: inoculating a bioreactor with one or more first microorganisms and a first fluidic support medium, the bioreactor comprising one or more bioreactor walls at least partially enclosing a bioreactor cavity, being configured to be at least one of folded up or rolled up, and being sterile when the bioreactor is inoculated with the one or more first microorganisms, the one or more bioreactor walls comprising at least one bioreactor wall material, and the at least one bioreactor wall material being flexible and at least partially transparent; and vitally supporting the one or more first microorganisms with the bioreactor, a supply of light, and a supply of organic carbon, such that at least one of: (i) when the one or more first microorganisms are taxonomically classified in taxonomic family Haematococcaceae, at least one of an average density of the one or more first microorganisms is greater than or equal to approximately 12 grams per liter or an average maximum production rate of the one or more first microorganisms is greater than or equal to approximately 2.5 grams per liter per day, (ii) when the one or more first microorganisms are taxonomically classified in taxonomic family Chlorellaceae, at least one of the average density of the one or more first microorganisms is greater than or equal to approximately 36 grams per liter or the average maximum production rate of the one or more first microorganisms is greater than or equal to approximately 9 grams per liter per day, or (iii) when the one or more first microorganisms are taxonomically classified in taxonomic family Chlamydomonadaceae, at least one of the average density of the one or more first microorganisms is greater than or equal to approximately 7 grams per liter or the average maximum production rate of the one or more first microorganisms is greater than or equal to approximately 3 grams per liter per day.

Some embodiments include a method. The method can comprise: inoculating a bioreactor with one or more first microorganisms and a first fluidic support medium, the bioreactor comprising one or more bioreactor walls at least partially enclosing a bioreactor cavity, being configured to be at least one of folded up or rolled up, and being sterile when the bioreactor is inoculated with the one or more first microorganisms, the one or more bioreactor walls comprising at least one bioreactor wall material, and the at least one bioreactor wall material being flexible and at least partially transparent; vitally supporting the one or more first microorganisms with the bioreactor, a supply of light, and a supply of organic carbon, such that at least one of: (i) when the one or more first microorganisms are taxonomically classified in taxonomic family Haematococcaceae, at least one of an average density of the one or more first microorganisms is greater than or equal to approximately 12 grams per liter or an average maximum production rate of the one or more first microorganisms is greater than or equal to approximately 2.5 grams per liter per day, (ii) when the one or more first microorganisms are taxonomically classified in taxonomic family Chlorellaceae, at least one of the average density of the one or more first microorganisms is greater than or equal to approximately 36 grams per liter or the average maximum production rate of the one or more first microorganisms is greater than or equal to approximately 9 grams per liter per day, or (iii) when the one or more first microorganisms are taxonomically classified in taxonomic family Chlamydomonadaceae, at least one of the average density of the one or more first microorganisms is greater than or equal to approximately 7 grams per liter or the average maximum production rate of the one or more first microorganisms is greater than or equal to approximately 3 grams per liter per day; mechanically supporting the bioreactor with a support structure comprising a first frame and a second frame together being operable to mechanically support the bioreactor in interposition between the first frame and the second frame; and supplying a temperature maintenance fluid to the first frame to maintain a set point temperature of the bioreactor through an exchange of thermal energy between the first frame and the bioreactor while vitally supporting the one or more first microorganisms with the bioreactor and while mechanically supporting the bioreactor with the support structure.

Some embodiments include a method. The method can comprise: conducting a first sterilization of an assembled bioreactor, wherein sterilizing the assembled bioreactor comprises at least one of gamma irradiating the assembled bioreactor or autoclaving the assembled bioreactor; after conducting the first sterilization of the assembled bioreactor, vitally supporting one or more first microorganisms with the assembled bioreactor; after vitally supporting the one or more first microorganisms with the assembled bioreactor, removing the one or more first microorganisms from the assembled bioreactor; after removing the one or more first microorganisms from the assembled bioreactor, gathering up the assembled bioreactor, wherein gathering up the assembled bioreactor after removing the one or more first microorganisms from the assembled bioreactor comprises at least one of folding the assembled bioreactor after removing the one or more first microorganisms from the assembled bioreactor or rolling up the assembled bioreactor after removing the one or more first microorganisms from the assembled bioreactor; after gathering up the assembled bioreactor, conducting a second sterilization of the assembled bioreactor, wherein the second sterilization of the assembled bioreactor comprises autoclaving the bioreactor; and after conducting the second sterilization of the assembled bioreactor, vitally supporting one or more second microorganisms with the assembled bioreactor.

Some embodiments include a method. The method can comprise: gathering up an assembled bioreactor before conducting a first sterilization of the assembled bioreactor, wherein gathering up the assembled bioreactor before conducting the first sterilization of the assembled bioreactor comprises at least one of folding the assembled bioreactor before sterilizing the bioreactor or rolling up the bioreactor before sterilizing the assembled bioreactor; conducting the first sterilization of the assembled bioreactor, wherein sterilizing the assembled bioreactor comprises at least one of gamma irradiating the assembled bioreactor or autoclaving the assembled bioreactor; after conducting the first sterilization of the assembled bioreactor, vitally supporting one or more first microorganisms with the assembled bioreactor; after vitally supporting the one or more first microorganisms with the assembled bioreactor, removing the one or more first microorganisms from the assembled bioreactor; after removing the one or more first microorganisms from the assembled bioreactor, gathering up the assembled bioreactor, wherein gathering up the assembled bioreactor after removing the one or more first microorganisms from the assembled bioreactor comprises at least one of folding the assembled bioreactor after removing the one or more first microorganisms from the assembled bioreactor or rolling up the assembled bioreactor after removing the one or more first microorganisms from the assembled bioreactor; after gathering up the assembled bioreactor, conducting a second sterilization of the assembled bioreactor, wherein the second sterilization of the assembled bioreactor comprises autoclaving the bioreactor; and after conducting the second sterilization of the assembled bioreactor, vitally supporting one or more second microorganisms with the assembled bioreactor. Meanwhile, the assembled bioreactor can comprise a greatest physical dimension, and the assembled bioreactor can be the at least one of folded up or rolled up such that the greatest physical dimension is reducible by at least approximately 75%.

Some embodiments include a method. The method can comprise: providing a support structure; and providing a bioreactor operable to vitally support one or more microorganisms. The bioreactor can comprise a bioreactor cavity configured to contain the one or more microorganisms and a fluidic support medium, and one or more bioreactor walls at least partially enclosing the bioreactor cavity. Meanwhile, the one or more bioreactor walls can comprise at least one bioreactor wall material, and the at least one bioreactor wall material can be flexible. Also, the support structure can be operable to mechanically support the bioreactor. Further, providing the support structure can comprise: providing a first frame; providing a second frame; and configuring the first frame and the second frame such that the first frame and the second frame together are operable to mechanically support the bioreactor in interposition between the first frame and the second frame. The first frame can be further operable to maintain a set point temperature of the bioreactor through an exchange of thermal energy between the first frame and the bioreactor when the bioreactor is vitally supporting the one or more microorganisms and when the support structure is mechanically supporting the bioreactor.

Some embodiments include a method. The method can comprise: providing a support structure; providing a bioreactor operable to vitally support one or more microorganisms; and interposing the bioreactor between the first frame and the second frame. The bioreactor can comprise a bioreactor cavity configured to contain the one or more microorganisms and a fluidic support medium, and one or more bioreactor walls at least partially enclosing the bioreactor cavity. Meanwhile, the one or more bioreactor walls can comprise at least one bioreactor wall material, and the at least one bioreactor wall material can be flexible. Also, the support structure can be operable to mechanically support the bioreactor. Further, providing the support structure can comprise: providing a first frame; providing a second frame; and configuring the first frame and the second frame such that the first frame and the second frame together are operable to mechanically support the bioreactor in interposition between the first frame and the second frame. Further still, the first frame can be operable to maintain a set point temperature of the bioreactor through an exchange of thermal energy between the first frame and the bioreactor when the bioreactor is vitally supporting the one or more microorganisms and when the support structure is mechanically supporting the bioreactor, and the second frame can be operable to maintain the set point temperature of the bioreactor through an exchange of thermal energy between the second frame and the bioreactor when the bioreactor is vitally supporting the one or more first microorganisms and when the support structure is mechanically supporting the bioreactor.

Turning to the drawings, FIG. 1 illustrates an exemplary block diagram of a system 100, according to an embodiment. System 100 is merely exemplary and is not limited to the embodiments presented herein. System 100 can be employed in many different embodiments or examples not specifically depicted or described herein.

System 100 comprises a bioreactor 101. Meanwhile, bioreactor 101 comprises a bioreactor cavity 102 and one or more bioreactor walls 103. Further, bioreactor 101 can comprise one or more bioreactor fittings 104, one or more gas delivery devices 105, one or more flexible tubes 106, one or more parameter sensing devices 109, and/or one or more pressure regulators 117.

In many embodiments, bioreactor fitting(s) 104 can comprise one or more gas delivery fittings 107, one or more fluidic support medium delivery fittings 110, one or more organic carbon material delivery fittings 111, one or more bioreactor exhaust fittings 112, one or more bioreactor sample fittings 113, and/or one or more parameter sensing device fittings 121. In these or other embodiments, flexible tube(s) 106 can comprise one or more gas delivery tubes 108, one or more organic carbon material delivery tubes 114, one or more bioreactor sample tubes 115, and/or one or more fluidic support medium delivery tubes 116. Further, in these or other embodiments, parameter sensing device(s) 109 can comprise one or more pressure sensors 118, one or more temperature sensors 119, one or more pH sensors 120, and/or one or more chemical sensors 122.

As explained in greater detail herein, bioreactor 101 is operable to vitally support (e.g., sustain, grow, nurture, cultivate, etc.) one or more organisms (e.g., one or more macroorganisms, one or more microorganisms, etc.). In these or other embodiments, the organism(s) can comprise one or more autotrophic organisms or one or more heterotrophic organisms. In further embodiments, the organism(s) can comprise one or more mixotrophic organisms. In many embodiments, the organism(s) can comprise one or more phototrophic organisms. In still other embodiments, the organism(s) can comprise one or more genetically modified organisms. In some embodiments, the organism(s) vitally supported by bioreactor 101 can comprise one or more organism(s) of a single type, multiple single organisms of different types, or multiple ones of one or more organisms of different types.

In many embodiments, exemplary microorganism(s) that bioreactor 101 may be implemented to vitally support can include algae (e.g., microalgae), fungi (e.g., mold), and/or cyanobacteria. For example, in many embodiments, bioreactor 101 can be implemented to vitally support microalgae that are taxonomically classified in one or more of the following taxonomic phyla: Chlorophyta, Cyanophyta (Cyanobacteria), and Heterokontophyta. Further, in many embodiments, bioreactor 101 can be implemented to vitally support microalgae that are taxonomically classified in one or more of the following taxonomic classes: Bacillariophyceae, Eustigmatophyceae, Chrysophyceae, Chlorophyceae, and Trebouxiophyceae. Further still, in many embodiments, bioreactor 101 can be implemented to vitally support microalgae that are taxonomically classified in one or more of the following taxonomic familiae: Chlorellaceae, Haematococcaceae, Scenedesmaceae, Porphyridiaceae, Chlamydomonadaceae, or Micractiniaceae. Even further still, in various embodiments, bioreactor 101 can be implemented to vitally support microalgae that are taxonomically classified in one or more of the following taxonomic genera: *Nannochloropsis, Chlorella, Haematococcus, Dunaliella, Scenedesmus, Selenastrum, Oscillatoria, Phormidium, Porphyridium, Chlamydomonas, Micractinium, Spirulina, Amphora,* and *Ochromonas*. Even further still yet, in a variety of embodiments, bioreactor 101 can be implemented to vitally support microalgae that are taxonomically classified in one or more of the following taxonomic species: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana*.

Exemplary embodiments of bioreactor 101 and exemplary types of organisms able to be vitally supported by bioreactor 101 are disclosed herein, including at Tables 1-5 below, which are not in any way intended to limit the scope of the invention. As would be understood in the art, the reclassification of various taxa is not unusual, and occurs as developments in science are made. Any disclosure in the specification regarding the taxonomic classification of exemplary types of organisms should be viewed in light of such developments.

For example, a strain of microalgae taxonomically classified in the *Chlorella* genus that achieved the performance characteristics described herein with respect to taxonomic family Chlorellaceae, and that was implemented with the methods described herein provides an exemplary organism able to be vitally supported by bioreactor 101 but is not intended to limit implementation of the invention to a particular strain of microalgae. Analysis of the deoxyribonucleic acid (DNA) sequence of the exemplary strain of *Chlorella* in the NCBI 18s ribosomal DNA (rDNA) reference database of the Culture Collection of Algae at the University of Cologne (CCAC) in Cologne, Germany showed substantial similarity (i.e., greater than 95%) of the exemplary strain of *Chlorella* with multiple known strains of microalgae taxonomically classified in the *Chlorella* and *Micractinium* genera. Microalgae taxonomically classified in the *Chlorella* and *Micractinium* genera appear closely related in many taxonomic classification trees for microalgae, and types of microalgae may be re-classified from time to time within the *Chlorella* and *Micractinium* genera. Accordingly, while the exemplary microalgae strain is referred to herein as being of the *Chlorella* genus, it is recognized that microalgae strains in related taxonomic classifications with similar characteristics to the exemplary microalgae strain would reasonably be expected to produce similar results. Therefore, in many embodiments, references herein to an organism classified in a first taxonomic genus (e.g., *Chlorella*) can include an organism classified in another taxonomic genus (e.g., *Micractinium*) that is genetically and/or morphologically similar to the first genus, and vice versa.

Bioreactor cavity 102 can hold (e.g., contain) the organism(s) being vitally supported by bioreactor 101, and in many embodiments, also can contain a fluidic support medium configured to hold, and in many embodiments, submerge the organism(s). In many embodiments, the fluidic support medium can comprise a culture medium, and the culture medium can comprise water. Meanwhile, bioreactor cavity 102 is at least partially formed and enclosed by bioreactor wall(s) 103. When bioreactor 101 is implemented with bioreactor fitting(s) 104, bioreactor fitting(s) 104 together with bioreactor wall(s) 103 can fully form and enclose bioreactor cavity 102. Further, as explained in greater detail below, bioreactor wall(s) 103 and one or more of bioreactor fitting(s) 104, as applicable, can be operable to at least partially (e.g., fully) seal the contents of bioreactor cavity 102 (e.g., the organism(s) and/or fluidic support medium) within bioreactor cavity 102. As a result, bioreactor 101 can maintain conditions mitigating the risk of introducing foreign (e.g., unintended) and/or contaminating organisms to bioreactor cavity 102. In other words, bioreactor 101 can engender the dominance (e.g., proliferation) of certain (e.g., intended) organism(s) being vitally supported at bioreactor 102 over foreign (e.g., unintended) and/or contaminating organisms. For example, bioreactor 101 can maintain substantially (e.g., absolutely) axenic conditions in the bioreactor cavity 102.

Bioreactor wall(s) 103 comprise one or more bioreactor wall materials. When bioreactor wall(s) 103 comprise multiple bioreactor walls, two or more of the bioreactor walls can comprise the same bioreactor wall material(s) and/or two or more of the bioreactor walls can comprise different bioreactor wall material(s).

In many embodiments, part or all of the bioreactor wall material(s) can comprise (e.g., consist of) one or more flexible materials. In some embodiments, bioreactor 101 can comprise a bag bioreactor.

In these or other embodiments, part or all of the bioreactor wall material(s) (e.g., the flexible material(s)) can comprise one or more partially transparent (e.g., fully transparent) and/or partially translucent (e.g., fully translucent) materials, such as, for example, when bioreactor 101 comprises a photobioreactor (i.e., when the organism(s) comprise phototrophic organism(s)). For example, implementing the bioreactor wall material(s) (e.g., the flexible material(s)) with at least partially transparent or translucent materials can permit light radiation to pass through bioreactor wall(s) 103 to be used as an energy source by the organism(s) contained at bioreactor cavity 102. Still, in some embodiments, bioreactor 101 can vitally support phototrophic organisms when the bioreactor wall material(s) (e.g., the flexible material(s)) of bioreactor wall(s) 103 are opaque, such as, for example, by providing sources of light radiation internal to bioreactor cavity 102. Further, in some embodiments, part or all of the bioreactor wall material(s) (e.g., the flexible material(s)) can comprise one or more selectively partially transparent (e.g., fully transparent) and/or partially translucent (e.g., fully translucent) materials, able to shift from opaque to at least partial transparency (e.g., full transparency) or at least partial translucency (e.g., full translucency).

For example, the bioreactor wall material(s) (e.g., the flexible and/or at least partially transparent or translucent material(s)) can comprise one or more polymer materials or one or more other suitable materials. In these or other embodiments, exemplary polymer material(s) can comprise polypropylene, polyamide, polyethylene, polyphenylsulfone, polyvinylidene fluoride, ethylene chlorotrifluoroethylene copolymer, polyetherimide, polysulfone, polyphenylene sulfide, thermoplastic polyimide, polyetheretherkeytone, and/or polyaryletherketone. In some embodiments, the bioreactor wall material(s) (e.g., the flexible and/or at least partially transparent or translucent material(s)) can comprise a melting point greater than or equal to approximately 125 degrees Celsius and less than or equal to approximately 225 degrees Celsius. In further embodiments, the bioreactor wall material(s) (e.g., the flexible and/or at least partially transparent or translucent material(s)) can comprise an elastic modulus greater than or equal to approximately 1.1 Giga-Pascals and less than or equal to approximately 2.5 Giga-Pascals.

Further, bioreactor wall(s) 103 each can be manufactured from one or more sheets of material (e.g., thin films). In some embodiments, when one or more of bioreactor wall(s) 103 each comprise multiple sheets of material, the multiple sheets of material can be laminated or coextruded together.

In these laminated or coextruded embodiments, the multiple sheets can be devoid of any air bubbles between them or can comprise one or more air bubbles between them. In some embodiments, implementing the laminated or coextruded multiple sheets with air bubbles in between can make it easier to identify a leak is present to alert an operator of bioreactor 101 that bioreactor cavity 102 may no longer be sealed and/or in an axenic condition, as explained in greater detail below, and can facilitate cleanup efforts. In these or other embodiments, two or more of the multiple sheets of material can comprise the same bioreactor wall material(s) and/or two or more of the multiple sheets of material can comprise different bioreactor wall material(s). For example, in some embodiments, each of bioreactor wall(s) 103 can comprise two sheets of material laminated or coextruded together with one sheet comprising polypropylene and one sheet comprising polyamide.

Meanwhile, in many embodiments, one or more of bioreactor wall(s) 103 can be coupled together to at least partially form and enclose bioreactor cavity 102. For example, the one or more of bioreactor wall(s) 103 can be coupled together by heat welding (e.g., heat sealing, hot plate welding, laser welding, etc.) or by another suitable coupling method. Further, one or more parts of bioreactor wall(s) 103 can be coupled together (e.g., by heat welding) to structurally reinforce bioreactor 101. When bioreactor wall(s) 103 are manufactured from a single sheet of material, the single sheet of material can be folded over and coupled (e.g., bonded) to itself in order to form bioreactor cavity 102. Meanwhile, when bioreactor wall(s) 103 are manufactured from multiple sheets of material, the multiple sheets of material can be coupled (e.g., bonded) together to form bioreactor cavity 102.

Further, when one or more of bioreactor wall(s) 103 comprise two sheets of material laminated together with one sheet comprising polypropylene and one sheet comprising polyamide, bioreactor wall(s) 103 can be coupled (e.g., bonded) together at the sheet or sheets of bioreactor wall(s) 103 that comprise polypropylene. For example, in some embodiments, one or more sheets of the laminated materials (e.g., polypropylene sheet(s)) can be joined (e.g., bonded) by heat welding and one or more sheets of the laminated materials (e.g., polyamide sheet(s)) cannot be joined (e.g., bonded) together by heat welding. In these or other embodiments, the joinable sheets of the laminated materials can be arranged so that the joinable sheets face inwardly toward bioreactor cavity 102 and the non-joinable sheets face outwardly away from bioreactor cavity 102 when bioreactor wall(s) 103 are coupled together.

Bioreactor cavity 102 can comprise a cavity volume and a cavity surface area. The cavity surface area can refer to a total surface area of the one or more surfaces forming bioreactor cavity 102. The cavity volume and/or cavity surface area of bioreactor cavity 102 can comprise any desirable volume and/or surface area. However, in some embodiments, the cavity volume and/or cavity surface area can be constrained by an available geometry (e.g., the dimensions) of the sheet material(s) used to manufacture bioreactor wall(s) 103. Other factors that can constrain the cavity volume and/or cavity surface area can include a light penetration depth through bioreactor wall(s) 103 and into bioreactor cavity 102 (e.g., when the organism(s) vitally supported by bioreactor 101 are phototrophic organism(s)), a size of an available autoclave for sterilizing bioreactor 101 as discussed in greater detail below, and/or a size of a support structure implemented to mechanically support bioreactor 101. For example, the support structure can be similar or identical to support structure 323 (FIG. 3) and/or support structure 423 (FIG. 4). In many embodiments, the cavity volume of bioreactor cavity 102 can be greater than or equal to approximately 3.785 liters, greater than or equal to approximately 18.92 liters, and/or greater than or equal to approximately 25.48 liters. In some embodiments, the cavity volume of bioreactor cavity 102 can be less than or equal to approximately 248.9 liters.

Meanwhile, bioreactor cavity 102 can comprise a largest lateral cross sectional area. In many embodiments, the largest lateral cross sectional area of bioreactor cavity 102 can refer to a largest cross sectional area of bioreactor cavity 102 measured parallel to the width and depth dimensions of bioreactor 101. In these or other embodiments, the lateral cross sectional area of bioreactor cavity 102 can be measured from the cavity surface of bioreactor cavity 102. In many embodiments, the greatest lateral cross sectional area of bioreactor cavity 102 can be greater than or equal to approximately 0.043 square meters and less than or equal to approximately 0.318 square meters.

Bioreactor 101 and/or bioreactor cavity 102 can comprise any desirable geometries (e.g., dimensions and/or shapes). For example, the geometry of bioreactor 101 can be at least partially determined by cutting the sheet material(s) used for bioreactor wall(s) 103 to the desired geometry. Meanwhile, the geometry of bioreactor cavity 102 can be determined by the points of coupling (e.g., one or more weld lines) of bioreactor wall(s) 103, and in some embodiments, by one or more fold lines of bioreactor wall(s) 103. In many embodiments, bioreactor 101 and/or bioreactor cavity 102 can comprise an approximately polygonal prismatic shape (e.g., an approximately rectangular, hexagonal, or octagonal prismatic shape).

Meanwhile, bioreactor 101 can comprise a length (e.g., longest) dimension, a width dimension, and a depth dimension. The width and depth dimensions can represent greatest dimensions of bioreactor 101 in directions that are approximately orthogonal to the length dimension and to each other. In these embodiments, the length dimension can be greater than or equal to approximately 182 centimeters and less than or equal to approximately 244 centimeters; the width dimension can be greater than or equal to approximately 51 centimeters and less than or equal to approximately 102 centimeters; and/or the depth dimension can be greater than or equal to approximately 7 centimeters and less than or equal to approximately 10 centimeters.

Also, bioreactor wall(s) 103 can comprise a bioreactor wall thickness. When bioreactor wall(s) 103 comprise multiple bioreactor walls, two or more of the bioreactor walls can comprise the same bioreactor wall thickness and/or two or more of the bioreactor walls can comprise different bioreactor wall thicknesses. In many embodiments, the bioreactor wall thickness can be greater than or equal to approximately 152.4 micrometers and less than or equal to approximately 355.6 micrometers. In some embodiments, the bioreactor wall thickness can be approximately 254.0 micrometers.

Meanwhile, bioreactor wall(s) 103 can comprise an exterior surface area. The exterior surface area of bioreactor wall(s) 103 can refer to a total surface area of an exterior of bioreactor wall(s) 103.

Bioreactor fitting(s) 104 (e.g., gas delivery fitting(s) 107, fluidic support medium delivery fitting(s) 110, organic carbon material delivery fitting(s) 111, bioreactor exhaust fitting(s) 112, bioreactor sample fitting(s) 113, parameter sensing device fittings 121) can communicate with bioreactor cavity 102 to provide ingress to and/or egress from bioreactor cavity 102 (e.g., while maintaining an at least partial seal of bioreactor cavity 102). In many embodiments, bioreactor fitting(s) 104 can be coupled to bioreactor wall(s) 103 and/or can be located (e.g., disposed) at one or more apertures passing through bioreactor wall(s) 103. Meanwhile, flexible tube(s) 106 (e.g., gas delivery tube(s) 108, organic carbon material delivery tube(s) 114, bioreactor sample tube(s) 115) can be coupled to one or more of bioreactor fitting(s) 104 and can be located (e.g., disposed) within bioreactor cavity 102. Flexible tube(s) 106 can comprise one or more flexible and/or at least partially transparent materials, such as, for example, one or more polymers.

For example, fluidic support medium fitting(s) 110 can be coupled to fluidic support medium delivery tube(s) 116, such as, for example, at one or more inputs of fluidic support medium delivery tube(s) 116. Fluidic support medium fitting(s) 110 can receive and supply (e.g., via fluidic support medium delivery tube(s) 116) the organism(s) to bioreactor cavity 102. Further, fluidic support medium fitting(s) 110 can receive and supply (e.g., via fluidic support medium delivery tube(s) 116) the fluidic support medium, one or more nutritional media, one or more anti-foaming agents, and/or one or more surfactants to bioreactor cavity 102.

For example, nutritional media can comprise one or more components (e.g., organic compounds, inorganic compounds, and/or water) aiding in the vital support of the organism(s) at bioreactor cavity 102. Exemplary nutritional media can comprise magnesium sulfate heptahydrate, trace metals, phosphate, phosphate dibasic, one or more nitrates (e.g., sodium nitrate), iron, and/or potassium phosphate dibasic.

In many embodiments, the nutritional media can be supplied to the organism(s) at bioreactor cavity 102 when the organism(s) reach a certain culture density (e.g., a threshold culture density). For example, the nutritional media can be supplied to the organism(s) at bioreactor cavity 102 when the organism(s) reach a culture density of at least approximately 5 grams per liter, 10 grams per liter, or 15 grams per liter. In these or other embodiments, the nutritional media can be supplied to the organism(s) at bioreactor cavity 102 each time the culture density of the organism(s) increases by a certain culture density. For example, the nutritional media can be supplied to the organism(s) at bioreactor cavity 102 when and/or each time the organism(s) reach a culture density of greater than or equal to approximately 2 grams per liter and less than or equal to approximately 3 grams per liter.

Meanwhile, the anti-foaming agent(s) can comprise one or more agents (e.g., chemicals) configured to reduce and/or offset foam production by the organism(s). Reducing and/or offsetting foam production by the organism(s) can prevent bioreactor cavity 102 from rupturing.

Further, the surfactant(s) can comprise one or more compounds configured to reduce a surface tension between two or more of the contents (e.g., one or more organism(s) and a fluidic support medium) of bioreactor cavity 102. Reducing the surface tension between two or more of the contents of bioreactor cavity 102 can aid in mixing the contents of bioreactor cavity 102 as described further below with respect to gas delivery device(s) 105.

In many embodiments, fluidic support medium delivery tube(s) 116 can convey the organism(s), the fluidic support medium, the one or more nutritional media, the anti-foaming agent(s), and/or the surfactant(s) to one or more outputs of fluidic support medium delivery tube(s) 116 that drain into bioreactor cavity 102. In many embodiments, one or more of these output(s) can comprise a non-planar cross section within bioreactor cavity 102 to prevent the output(s) from suctioning to bioreactor wall(s) 103. For example, one or more v-shaped cuts can be provided at the output(s) to form the non-planar cross section(s). Still, in other embodiments, fluidic support medium delivery tube(s) 116 can be omitted.

In many embodiments, the organism(s) being vitally supported by bioreactor 101 can be partially and/or fully harvested (e.g., removed) from bioreactor cavity 102. In some embodiments, the organism(s) being vitally supported by bioreactor 101 can be partially and/or fully harvested (e.g., removed) from bioreactor cavity 102 via fluidic support medium fitting(s) 110. However, in many embodiments, one or more of fluidic support medium fitting(s) 110 can be decoupled (e.g., temporarily decoupled) and removed from bioreactor wall(s) 103 and the organism(s) can be partially and/or fully harvested (e.g., removed) from bioreactor cavity 102 via the aperture(s) in bioreactor wall(s) 103 from which the decoupled fitting(s) of fluidic support medium fitting(s) 110 are removed. In various embodiments, all of the organism(s) being vitally supported by bioreactor 101 can be harvested (e.g., removed) from bioreactor cavity 102 simultaneously in one entire batch (i.e., fully harverested) or the organism(s) being vitally supported by bioreactor 101 can be harvested (e.g., removed) from bioreactor cavity 102 in multiple batches over time (e.g., partially harvested). In other embodiments, the organism(s) being vitally supported by bioreactor 101 can be continuously partially harvested (e.g., removed) from bioreactor cavity 102 over time. In some embodiments, when the organism(s) being vitally supported at bioreactor 101 are partially and/or continuously harvested, bioreactor cavity 102 can also be re-inoculated with new organism(s) and/or fluidic support media. Exemplary embodiments of methods for inoculating (e.g., supplying) and re-inoculating bioreactor cavity 102 with organism(s) are discussed in greater detail below.

In some embodiments, the organism(s) being vitally supported by bioreactor 101 can be continuously partially harvested (e.g., removed) from bioreactor cavity 102 at intervals. Although the interval can be any suitable period of time, which may be determined based on the type of organism(s) being vitally supported by bioreactor 101, in many embodiments, the interval can be approximately 7-12 days or approximately 10-12 days.

In further embodiments, the organism(s) being vitally supported by bioreactor 101 can be partially and/or continuously partially harvested (e.g., removed) from bioreactor cavity 102 when a culture density of the organism(s) reaches a certain culture density. Although the culture density for partially and/or continuously partially harvesting (e.g., removing) the organism(s) from bioreactor cavity 102 can be any suitable culture density, which may be determined based on the type of organism(s) being vitally supported by bioreactor 101, in many embodiments, the culture density for partially and/or continuously partially harvesting (e.g., removing) the organism(s) from bioreactor cavity 102 can comprise at least approximately 2 grams per liter. In more specific embodiments, the culture density for partially and/or continuously partially harvesting (e.g., removing) the organism(s) from bioreactor cavity 102 can be (i) greater than or equal to approximately 2 grams per liter and less than or equal to approximately 5 grams per liter, (ii) greater than or equal to approximately 7 grams per liter and less than or equal to approximately 12 grams per liter, (iii) greater than or equal to approximately 7 grams per liter and less than or equal to approximately 10 grams per liter, or (iv) greater than or equal to approximately 20 grams per liter and less than or equal to approximately 30 grams per liter.

In implementation, fluidic support medium fitting(s) 110 can comprise any suitable fitting or fittings configured to provide ingress of the organism(s), the fluidic support medium, the one or more nutritional media, the anti-foaming agent(s), and/or the surfactant(s) into, and in some embodiments, egress of the organism(s), the fluidic support medium, the one or more nutritional media, the anti-foaming agent(s), and/or the surfactant(s) out of bioreactor cavity 102. In many embodiments, the fitting(s) are configured to provide unidirectional ingress of the organism(s), the fluidic support medium, the one or more nutritional media the anti-foaming agent(s), and/or the surfactant(s) into bioreactor cavity 102 to help maintain an at least partial seal of bioreactor cavity 102. For example, in some embodiments, fluidic support medium fitting(s) 110 can comprise one or more check valves. Further, fluidic support medium fitting(s) 110 (e.g., the check valve(s)) can be sealed in place with one or more gaskets. In some embodiments, fluidic support medium fitting(s) 110 can comprise one or more filters configured to filter the fluidic support medium and/or the one or more nutritional media. For example, the filter(s) can comprise a single filter or multiple filters in series, can be disc shaped, and/or can be operable to filter microparticles (e.g., down to approximately 0.1 micrometers).

In these or other embodiments, organic carbon material delivery fitting(s) 111 can be coupled to organic carbon material delivery tube(s) 114, such as, for example, at one or more inputs of organic carbon material delivery tube(s) 114. Organic carbon material delivery fitting(s) 111 can receive and supply (e.g., via organic carbon material delivery tube(s) 114) organic carbon material to bioreactor cavity 102. In some embodiments, the organic carbon material can be used as an energy source by the organism(s) being vitally supported by bioreactor 101, such as, for example, when the organism(s) comprise heterotrophic organism(s) or mixotrophic organism(s).

Exemplary organic carbon materials can comprise acetic acid, acetate, or glucose. In some embodiments, the organic carbon materials can be mixed with ammonium bicarbonate, magnesium sulfate heptahydrate, trace metals, iron, phosphate, phosphate dibasic, one or more nitrates (e.g., sodium nitrate), such as, for example, before the organic carbon material(s) are supplied to the organism(s) being vitally supported by bioreactor 101. In these or other embodiments, the organic carbon materials can be mixed with one or more of the nutritional media, such as, for example, before the organic carbon material(s) are supplied to the organism(s) being vitally supported by bioreactor 101.

Further, organic carbon material delivery tube(s) 114 can convey the organic carbon material to one or more outputs of organic carbon material delivery tube(s) 114 that drain into bioreactor cavity 102. In many embodiments, one or more of these output(s) can comprise a non-planar cross section located within bioreactor cavity 102 to prevent the output(s) from suctioning to bioreactor wall(s) 103. For example, one or more v-shaped cuts can be provided at the output(s) to form the non-planar cross section(s). Still, in some embodiments, organic carbon material delivery tube(s) 114 can be omitted, and in further embodiments, organic carbon material delivery fitting(s) 111 can be omitted, such as, for example, when the organism(s) being vitally supported by bioreactor 101 are not heterotrophic or mixotrophic.

In implementation, organic carbon material delivery fitting(s) 111 can comprise any suitable fitting or fittings configured to provide ingress (e.g., unidirectional ingress) of the carbon source material into bioreactor cavity 102. For example, in some embodiments, fluidic support medium fitting(s) 110 can comprise one or more check valves. Meanwhile, in many embodiments, organic carbon material delivery fitting(s) 111 can comprise one or more filters configured to filter the organic carbon material received at organic carbon material delivery fitting(s) 111 of contaminants. For example, the filter(s) can comprise a single filter or multiple filters in series, can be disc shaped, and/or can be operable to filter micro-particles or nano-particles. Further, organic carbon material delivery fitting(s) 111 (e.g., the check valve(s)) can be sealed in place with one or more gaskets.

In these or other embodiments, bioreactor sample fitting(s) 113 can be coupled to bioreactor sample tube(s) 115, such as, for example, at one or more outputs of bioreactor sample tube(s) 115. Bioreactor sample fitting(s) 113 can be used to obtain (e.g., via bioreactor sample tube(s) 115) one or more samples of the organism(s) held at bioreactor cavity 102, such as, for example, to determine a condition of the organism(s). For example, in many embodiments, bioreactor sample fitting(s) 113 can receive one or more syringes that can apply suction to bioreactor sample fitting(s) 113 to withdraw (e.g., via organic carbon material delivery tube(s) 114) the sample(s) of the organism(s) held at bioreactor cavity 102.

Further, bioreactor sample tube(s) 115 can receive the sample(s) from one or more inputs of bioreactor sample tube(s) 115 in communication with the organism(s) at bioreactor cavity 102 and convey the sample(s) to bioreactor sample fitting(s) 113. In many embodiments, one or more of these input(s) can comprise a non-planar cross section located within bioreactor cavity 102 to prevent the input(s) from suctioning to bioreactor wall(s) 103. For example, one or more v-shaped cuts can be provided at the input(s) to form the non-planar cross section(s). Still, in some embodiments, bioreactor sample tube(s) 115 can be omitted, and in further embodiments, bioreactor sample fitting(s) 113 can be omitted.

In implementation, bioreactor sample fitting(s) 113 can comprise any suitable fitting or fittings configured to permit the sample(s) of the organism(s) to be obtained from bioreactor cavity 102 without disrupting an at least partial seal of bioreactor cavity 102. For example, in some embodiments, bioreactor sample fitting(s) 113 can comprise one or more double check valves with stop cocks. In some embodiments, bioreactor sample fitting(s) 113 (e.g., the double check valve(s) with stop cocks) can be sealed in place with one or more gaskets.

In these or other embodiments, bioreactor exhaust fitting(s) 112 can vent gas (e.g., air) produced by the organism(s) being vitally supported by bioreactor 101 from bioreactor cavity 102 and/or gas injected into bioreactor cavity 102 by gas delivery device(s) 105, such as, for example, to reduce a cavity pressure at bioreactor cavity 102. In some embodiments, bioreactor exhaust fitting(s) 112 can be coupled (e.g., removably coupled) to one or more inputs of one or more bioreactor exhaust tubes located outside of bioreactor cavity 102. In other embodiments, the bioreactor exhaust tube(s) can be omitted.

In implementation, bioreactor exhaust fitting(s) 112 can comprise any suitable fitting or fittings configured to permit unidirectional egress of gas out from bioreactor cavity 102. For example, in some embodiments, bioreactor exhaust fitting(s) 112 can comprise one or more check valves. In some embodiments, bioreactor exhaust fitting(s) 112 (e.g., the check valve(s)) can be sealed in place with one or more gaskets.

In many embodiments, the bioreactor exhaust tube(s) can convey the gas vented from bioreactor exhaust fitting(s) 112 to a bleach-water solution in communication with the one or more outputs of the bioreactor exhaust tube(s) to sterilize contaminants of the vented gas. In some embodiments, the bleach-water solution can comprise a bleach to water ratio of greater than or equal to approximately 400 parts per million (ppm). In other embodiments, bioreactor exhaust fitting(s) 112 can comprise one or more filters configured to filter the vented gas of contaminants, such as, for example, when the bioreactor exhaust tube(s) are omitted. For example, the filter(s) can comprise a single filter or multiple filters in series, can be disc shaped, and/or can be operable to filter micro-particles (e.g., down to approximately 0.1 micrometers) or nano-particles.

In these or other embodiments, gas delivery fitting(s) 107 can be coupled to one or more inlets of gas delivery tube(s) 108, which can be coupled to gas delivery device(s) 105 at one or more outlets of gas delivery tube(s) 108. Gas delivery fitting(s) 107 can be configured to receive gas (e.g., air, oxygen, carbon dioxide, etc.) and supply the gas (e.g., via gas delivery tube(s) 108) to gas delivery device(s) 105. Gas delivery device(s) 105 can be located (e.g., disposed) within bioreactor cavity 102 and can be operable to inject the gas provided to gas delivery device(s) 105 into bioreactor cavity 102 to mix and/or aerate the organism(s) (e.g., within the fluidic support medium) being vitally supported by bioreactor 101. For example, gas delivery device(s) 105 can mix and/or aerate the organism(s) (e.g., within the fluidic support medium) being vitally supported by bioreactor 101 in order to prevent sedimentation of the organism(s) and to better distribute exposure of the organism(s) to energy sources (e.g., light and/or carbon source material) and/or nutritional components (e.g., the one or more nutritional media) at bioreactor cavity 102. In many embodiments, gas delivery device(s) 105 can be located (e.g., disposed) at a position low within bioreactor cavity 102 relative to the Earth to promote mixing of the organism(s) as gravitational forces return the organism(s) to gas delivery device(s) 105 after gas delivery device(s) 105 stir up the organism(s) with the injected gas. In some embodiments, gas delivery tube(s) 108 can be omitted and gas delivery device(s) 105 can be coupled directly to gas delivery fitting(s) 107.

In implementation, gas delivery fitting(s) 107 can comprise any suitable fitting or fittings configured to permit ingress (e.g., unidirectional ingress) of gas (e.g., air, oxygen, carbon dioxide, etc.) and to supply the gas to gas delivery device(s) 105. For example, in some embodiments, bioreactor sample fitting(s) 113 can comprise one or more check valves. Meanwhile, in many embodiments, gas delivery fitting(s) 107 can comprise one or more filters configured to filter the gas received at gas delivery fitting(s) 107 of contaminants. For example, the filter(s) can comprise a single filter or multiple filters in series, can be disc shaped, and/or can be operable to filter micro-particles (e.g., down to approximately 0.22 micrometers) or nano-particles. In some embodiments, bioreactor sample fitting(s) 113 (e.g., the check valve(s)) can be sealed in place with one or more gaskets.

Further, in implementation, gas delivery device(s) 105 can comprise one or more devices configured to inject gas into bioreactor cavity 102. In general, the arrangement and geometry of gas delivery device(s) 105 within bioreactor cavity 102 and the exit velocity, mass, and/or volume of gas injected by gas delivery device(s) 105 can affect the proficiency of the mixing and/or aeration of the organism(s) being vitally supported by bioreactor 101. However, increasing the exit velocity, mass, and/or volume of the gas also increases the shear forces acting on the organism(s), which at some level can harm (e.g., kill) the organism(s). Accordingly, in many embodiments, the exit velocity, mass, and/or volume of the gas can be limited based on the shear forces applied to the organism(s) and thus, the arrangement and geometry of gas delivery device(s) 105 can take on increased importance. In many embodiments, the arrangement and geometry of gas delivery device(s) 105 can be configured such that gas delivery device(s) 105 are no greater than approximately 10.2 centimeters away from at least part of bioreactor wall(s) 103, and when gas delivery device(s) 105 comprise multiple gas delivery devices, such that gas delivery device(s) 105 are no greater than approximately 10.2 centimeters away from each other. In these or other embodiments, gas delivery device(s) 105 can be configured such that a ratio of the active surface area of gas delivery device(s) 105 to the largest lateral cross sectional area of bioreactor cavity 102 is greater than or equal to approximately 13.00 and less than or equal to approximately 30.64. The active surface area of gas delivery device(s) 105 can refer to the surface area of gas delivery device(s) 105 from which gas can pass from gas delivery device(s) 105 to bioreactor cavity 102 (e.g., orifices, pores, etc.).

Meanwhile, gas delivery device(s) 105 can be configured so that gas bubbles of the gas injected into bioreactor cavity 102 comprise a diameter greater than or equal to approximately 40 micrometers and less than or equal to approximately 2 millimeters and/or so that a volumetric flow rate of the gas injected into bioreactor cavity 102 is greater than or equal to approximately 10 liters per minute and less than or equal to approximately 60, 120, 180, or 200 liters per minute. Further, gas delivery device(s) 105 can inject gas into bioreactor cavity 102 such that the gas comprises a superficial flow velocity when exiting gas delivery device(s) 105 of greater than or equal to approximately 0.000167 meters per second and less than or equal to approximately 0.0205 meters per second. Further still, gas delivery device(s) 105 can inject gas into bioreactor cavity 102 such that the volumetric mass-transfer coefficient ($k_L a$) of the gas to the organism(s) being vitally supported at bioreactor 101 is greater than or equal to approximately 0.062 inverse second ($s^{-1}$) to approximately 0.182 inverse second ($s^{-1}$).

In these or other embodiments, using surfactant(s) at bioreactor cavity 102 can permit improved mixing of the organism(s) being vitally supported by bioreactor 101 by reducing surface tension between two or more contents (e.g., one or more organisms and a fluidic support medium) at bioreactor cavity 102. Using the surfactant(s) in combination with gas delivery device(s) 105 configured so that gas bubbles of the gas injected into bioreactor cavity 102 comprise a diameter greater than or equal to approximately 40 micrometers and less than or equal to approximately 2 millimeters and/or so that a volumetric flow rate of the gas injected into bioreactor cavity 102 is greater than or equal to approximately 10 liters per minute and less than or equal to approximately 60, 120, 180, or 200 liters per minute can be advantageous when implementing bioreactor 101. For example, a residence time at bioreactor cavity 102 of the gas injected into bioreactor cavity 102 can be limited by a height of bioreactor cavity 102. In some embodiments, residence time can refer to an average amount of time taken for gas injected into bioreactor cavity 102 by gas delivery device(s) 105 to evacuate from bioreactor cavity 102 through bioreactor exhaust fitting(s) 112 and/or can refer to an average amount of time that gas injected into bioreactor cavity 102 by gas delivery device(s) 105 remains in contact with any organism(s) being vitally supported by bioreactor 101. Decreasing a height of bioreactor cavity 102 can decrease a residence time at bioreactor cavity 102 of the gas injected into bioreactor cavity 102, which can result in insufficient mixing and/or aeration, and therefore growth of the organism(s) being vitally supported by bioreactor 101. Accordingly, in many embodiments, using surfactant(s) in combination with gas delivery device(s) 105 configured so that gas bubbles of the gas injected into bioreactor cavity 102 comprise a diameter greater than or equal to approximately 40 micrometers and less than or equal to approximately 2 millimeters and/or so that a volumetric flow rate of the gas injected into bioreactor cavity 102 is greater than or equal to approximately 10 liters per minute and less than or equal to approximately 60, 120, 180, or 200 liters per minute can permit improved mixing and/or aeration of the organism(s) being vitally supported by bioreactor 101 to offset a decrease in residence time.

In many embodiments, gas delivery device(s) 105 can comprise one or more spargers. The sparger(s) can comprise porous and/or fixed-orifice sparger(s). Further, the fixed-orifice sparger(s) can be configured to inject gas uni-directionally and/or multi-directionally and/or can comprise fixed-orifices arranged uniformly and/or sparsely. Meanwhile, the porous sparger(s) inherently can be configured to inject gas multi-directionally and sparsely. The sparger(s) can comprise a sparger material comprising polymer (e.g., flashspun high density polyethylene, sintered polymer), ceramic, metalloid (e.g., silicon), and/or metal (e.g., stainless steel and/or porous stainless steel). Meanwhile, in some embodiments, the sparger material can comprise a flexible material. For example, in some embodiments, the sparger(s) can comprise tube or plate spargers. In these embodiments, the tube sparger(s) can comprise a diameter (e.g., 0.635 centimeters) and/or a length (e.g., 35.6 centimeters) as determined by the mixing and/or aeration needs of the organism(s) and/or as determined by the volume and geometry of bioreactor cavity 102. In many embodiments, the diameters of the pores and/or fixed-orifices of the sparger(s) implemented for gas delivery device(s) 105 can be configured so that gas bubbles of the gas injected into bioreactor cavity 102 comprise a diameter greater than or equal to approximately 40 micrometers and less than or equal to approximately 2 millimeters and/or so that a volumetric flow rate of the gas injected into bioreactor cavity 102 is greater than or equal to approximately 10 liters per minute and less than or equal to approximately 60, 120, 180, or 200 liters per minute.

Still, in other embodiments, gas delivery device(s) 105 and/or gas delivery fitting(s) 107 can be replaced or implemented concomitantly with one or more other bioreactor mixing and/or aeration device(s) configured to mix and/or aerate the organism(s) (e.g., within the fluidic support medium) being vitally supported by bioreactor 101. Exemplary other mixing device(s) can comprise one or more impellers, one or more air stones, etc.

In these or other embodiments, pressure regulator(s) 117 can limit a maximum cavity pressure of bioreactor cavity 102. In many embodiments, pressure regulator(s) 117 can be operable as a safety precaution to prevent bioreactor 101 from rupturing under the cavity pressure at bioreactor cavity 102.

For example, in some embodiments, one or more of pressure regulator(s) 117 can vent gas (e.g., air) produced by the organism(s) being vitally supported by bioreactor 101 from bioreactor cavity 102 to prevent the maximum cavity pressure of bioreactor cavity 102 from being exceeded. In some embodiments, bioreactor fitting(s) 104 and/or bioreactor exhaust fitting(s) 112 can comprise one or more of pressure regulator(s) 117. Further, in these or other embodiments, one or more of pressure regulator(s) 117 can be similar to bioreactor exhaust fitting(s) 112. For example, one or more of pressure regulator(s) 117 can communicate with bioreactor cavity 102 to provide egress from bioreactor cavity 102. In some embodiments, one or more of pressure regulator(s) 117 can comprise one or more blowoff valves configured to blow under a predetermined amount of cavity pressure. In other embodiments, one or more of pressure regulator(s) 117 can comprise one or more valves configured to open and vent the gas upon sensing the cavity pressure has exceeded a predetermined amount of cavity pressure, such as, for example, by reference to one or more of pressure sensor(s) 118 as discussed below.

In other embodiments, one or more of pressure regulator(s) 117 can restrict, stop, and/or reroute gas being received at gas delivery fitting(s) 107 and/or can restrict, stop, and/or reroute organic source material being received at organic carbon material delivery fitting(s) 111 to prevent the maximum cavity pressure of bioreactor cavity 102 from being exceeded. These pressure regulator(s) 117 can operate under the principal of preventing more gas from entering bioreactor cavity 102 (i.e., when regulating gas delivery fitting(s) 107) to prevent the maximum cavity pressure of bioreactor cavity 102 from being exceeded and/or under the principal of preventing more gas from being formed by the organism(s) (i.e., when regulating organic carbon material delivery fitting(s) 111) to prevent the maximum cavity pressure of bioreactor cavity 102 from being exceeded. In further embodiments, one or more of pressure regulator(s) 117 can comprise a valve configured to close (e.g., restricting or stopping flow) or open (e.g., rerouting flow) upon sensing the cavity pressure has exceeded a predetermined amount of cavity pressure, such as, for example, by reference to one or more of pressure sensor(s) 118 as discussed below.

In these or other embodiments, parameter sensing device fitting(s) 121 can receive parameter sensing device(s) 109 to permit parameter sensing devices to communicate with bioreactor cavity 102. Parameter sensing device(s) 109 (e.g., pressure sensor(s) 118, temperature sensor(s) 119, pH sensor(s) 120, chemical sensor(s) 122) can be operable to monitor (e.g., measure) one or more cavity environmental conditions (e.g., pressure, temperature, pH, chemical concentration, etc.) at bioreactor cavity 102. In some embodiments, one or more of parameter sensing device(s) 109 each can monitor (e.g., measure) multiple of the cavity environmental condition(s) at bioreactor cavity 102.

For example, pressure sensor(s) 118 can monitor the cavity pressure at bioreactor cavity 102, such as, for example, to determine the cavity pressure for pressure regulator(s) 117 and/or to help vitally support the organism(s) held at bioreactor cavity 102. Meanwhile, temperature sensor(s) 119 can monitor the cavity temperature of bioreactor cavity 102, pH sensor(s) 120 can monitor the cavity pH of bioreactor cavity 102, and oxygen sensor(s) 122 can monitor the quantity of one or more elements (e.g., oxygen) or compounds (e.g., carbon dioxide) present (e.g., dissolved) at bioreactor cavity 102 to help vitally support the organism(s) held at bioreactor cavity 102. For example, nutritional media, organic carbon material, light radiation, gas, etc. provided to bioreactor cavity 102 and/or the organism(s) can be regulated based on the data collected from parameter sensing device(s) 109. Further, bioreactor cavity 102 can be cooled or warmed to maintain a set point temperature of bioreactor 101. The set point temperature of bioreactor 101 can comprise a desired temperature of bioreactor 101. For example, the set point temperature can be determined based on the organism(s) being vitally supported by bioreactor 101 and can vary depending on the type or types of organism(s). In many examples, the set point temperature can be established to maximize an average density and/or average maximum production rate of the organism(s) being vitally supported at bioreactor 101.

In implementation, parameter sensing device fitting(s) 121 can comprise any suitable fitting or fittings configured to receive parameter sensing device(s) 109 for communication with bioreactor cavity 102. For example, in some embodiments, parameter sensing device fitting(s) 121 can comprise one or more check valves. In some embodiments, parameter sensing device fitting(s) 121 (e.g., the check valve(s)) can be sealed in place with one or more gaskets. Further, pressure sensor(s) 118 can comprise one or more pressure transducers; temperature sensor(s) 119 can comprise one or more thermometers, one or more thermocouples, etc.; pH sensor(s) 120 can comprise one or more pH meters; and/or chemical sensor(s) 122 can comprise one or more chemical meters (e.g., dissolved oxygen meters).

As indicated above, when bioreactor 101 comprises a photobioreactor, bioreactor 101 can permit light radiation to pass through bioreactor wall(s) 103 to be used as an energy source by the organism(s) being vitally supported by bioreactor 101. In these embodiments, light radiation can be supplied to the organism(s) by one or more light sources (e.g., light source(s) 337 (FIG. 3)) and/or by natural light. In many embodiments, a quantity of light supplied to the organism(s) being vitally supported by bioreactor 101 can depend on the type of organism(s) being vitally supported by bioreactor 101. Further, in these or other embodiments, a quantity of light supplied to the organism(s) being vitally supported by bioreactor 101 can be based upon a culture density of the organism(s). For example, in some embodiments, the quantity of light being supplied to the organism(s) can be changed (e.g., increased or decreased) when the organism(s) reach a certain culture density. In some embodiments, the quantity of light being supplied to the organism(s) can be doubled when the organism(s) reach a culture density of approximately 0.5 gram per liter. In these or other embodiments, the quantity of light can be measured in micro moles per square meter per second. Meanwhile, in many embodiments, a ratio of the exterior surface area of bioreactor wall(s) 103 to the cavity volume of bioreactor cavity 102 can be greater than or equal to approximately 5.23 inverse meters ($m^{-1}$) and less than or equal to approximately 17.98 inverse meters ($m^{-1}$).

Meanwhile, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be sterilized one or more times before being used to vitally support one or more organisms, such as, for example, when two or more or all of bioreactor cavity 102, bioreactor wall(s) 103, bioreactor fitting(s) 104, gas delivery device(s) 105, flexible tube(s) 106, parameter sensing device(s) 109, and pressure regulator(s) 117 are assembled together. Further, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be sterilized one or more times again after being used to vitally support one or more organisms to permit reuse of bioreactor 101 one or more times to support other organism(s). The organism(s) can be the same type or different types of organism(s) for the multiple uses of bioreactor 101. As a result, bioreactor cavity 102 can be substantially axenic when bioreactor 101 begins vitally supporting the organism(s) and can be maintained in a substantially axenic condition during the term of use by bioreactor wall(s) 103 and bioreactor fitting(s) 104 at least partially sealing bioreactor cavity 102. In many embodiments, bioreactor cavity 102 can be substantially axenic when bioreactor cavity 102 is at least 99.0 percent, 99.5 percent, or 99.9 percent free of organism(s) other than the organism(s) intended to be vitally supported by bioreactor 101 by relative volume to each other. In these or other embodiments, bioreactor cavity 102 can be substantially axenic when bioreactor cavity 102 is sufficiently free of foreign (e.g., unintended) and/or contaminating organism(s) that certain (e.g., intended) organism(s) being vitally supported at bioreactor cavity 102 maintain dominance (e.g., proliferate) over the foreign (e.g., unintended) and/or contaminating organism(s). Further, bioreactor cavity 102 can be absolutely axenic when bioreactor cavity 102 is 100 percent free of foreign (e.g., unintended) and/or contaminating organism(s) (e.g., macroorganisms and microorganisms).

In these embodiments, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be sterilized initially by gamma radiation exposure, autoclave, and/or chemical exposure (e.g., ethylene oxide) and then sterilized again for reuse by gamma radiation exposure, autoclave and/or chemical exposure. In many embodiments, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be sterilized again for reuse by autoclave at least once or multiple times without degrading (e.g., structurally damaging) bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) sufficiently to prevent bioreactor wall(s) 103 and bioreactor fitting(s) 104 from maintaining an at least partial seal of bioreactor cavity 102 and/or maintaining a level of non-contamination substantially similar to that of the level of non-contamination of an immediately prior use of bioreactor 101. In some embodiments, the level of non-contamination can be substantially similar when the contamination conditions are within approximately ±0.01 percent or ±0.02 percent of each other as it relates to the percentage extent to which bioreactor cavity 102 is free of organism(s) other than the organism(s) intended to be vitally supported by bioreactor 101 by relative volume to each other. In other words, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be sterilized again for reuse by gamma radiation exposure, autoclave, and/or chemical exposure at least once or multiple times while maintaining the structural integrity of bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117). Exemplary embodiments of methods for autoclaving bioreactor 101 are discussed in greater detail below.

As a volume of a contents (e.g., fluidic support medium, one or more nutritional media, organism(s), etc.) of bioreactor cavity 102 increases, stress placed on bioreactor 101, bioreactor wall(s) 103, and/or one or more welds coupling together bioreactor wall(s) 103 by the contents of bioreactor cavity 102 can cause bioreactor 101, bioreactor wall(s) 103, and/or one or more welds coupling together bioreactor wall(s) 103 to rupture. Accordingly, in some embodiments, bioreactor 101 can be positioned and/or at least partially sealed in a cavity of a containment vessel, such as, for example, to collect any of the fluidic support medium, one or more nutritional media, and/or organism(s) that may leak from bioreactor 101 in the event that bioreactor cavity 102 ruptures. Positioning and/or at least partially sealing bioreactor 101 in the cavity of the containment vessel can make it easier to identify a leak is present to alert an operator of bioreactor 101 that bioreactor cavity 102 may no longer be sealed and/or in an axenic condition, and can facilitate cleanup efforts. Notably, in some embodiments, loss of axenic conditions may warrant complete disposal of the contents of bioreactor cavity 102. However, in other embodiments, bioreactor cavity 101 can continue to vitally support the organism(s) even in the event an axenic condition of bioreactor cavity 102 is lost.

In these or other embodiments, the cavity of the containment vessel can be similar or identical to bioreactor cavity 102, and/or the containment vessel can be similar or identical to bioreactor 101. For example, the containment vessel can comprise a bag (e.g., an open bag). In many embodiments, the containment vessel can comprise one or more containment vessel walls. In these or other embodiments, the containment vessel walls can be similar or identical to bioreactor wall(s) 103.

In some embodiments, when bioreactor 101 is positioned and/or at least partially sealed in the cavity of the containment vessel, a containment vessel fluid can be positioned between an exterior of bioreactor wall(s) 103 and an interior of the containment vessel wall(s). In these embodiments, the containment vessel fluid can be operable to mechanically support bioreactor 101, such as, for example, by providing exterior pressure on the exterior of bioreactor wall(s) 103. Further, by providing exterior pressure on the exterior of bioreactor wall(s) 103, the containment vessel fluid can be operable to mitigate stress placed on bioreactor 101, bioreactor wall(s) 103, and/or one or more welds coupling together bioreactor wall(s) 103 by the contents (e.g., fluidic support medium, one or more nutritional media, organism(s), etc.) of bioreactor cavity 102.

The containment vessel fluid can comprise one or more fluids suitable to mechanically support bioreactor 101. In many embodiments, the containment vessel fluid can comprise water. In these embodiments, the containment vessel can be referred to as a water column. In some embodiments, implementing the containment vessel wall(s) and/or the containment vessel fluid to be transparent or translucent can permit light radiation to pass through the containment vessel wall(s) and/or the containment vessel fluid to reach the organism(s) at bioreactor cavity 102.

Further, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) is able to be gathered up by folding (e.g., in half or into quarters) and/or rolling up bioreactor 101 (e.g., like a sleeping bag). In many embodiments, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be manufactured of flexible materials permitting bioreactor 101 to be gathered up and/or fit into an autoclave. For example, in some embodiments, a greatest physical dimension of bioreactor 101 can be reduced by approximately 50 percent, 55 percent, 60 percent, 65 percent, 70 percent, 75 percent, 80 percent, 85 percent, or 90 percent by bioreactor 101 being gathered up. Accordingly, in some embodiments, flexible materials can refer to materials being sufficiently flexible to permit the greatest physical dimension of bioreactor 101 to be reduced by approximately 50 percent, 55 percent, 60 percent, 65 percent, 70 percent, 75 percent, 80 percent, 85 percent, or 90 percent by bioreactor 101 being gathered up and/or to be fit into an autoclave.

Advantageously, because bioreactor 101 can be sterilized one or more times generally, bioreactor 101 can be reused. Reuse of bioreactor 101 can result in cost savings over non-reusable bioreactors and can reduce material waste. Meanwhile, sterilization of bioreactor 101 by autoclaving can be beneficial over other forms of sterilization because bioreactor cavity 101 can be sterilized with little to no disassembly required and in a manner that is more cost effective than other forms of sterilization. For example, sterilization by autoclave does not require the expensive and complicated storage and transportation protocols that storing radioactive materials for gamma irradiation may require. Further, because bioreactor 101 can be gathered up, bioreactor 101 can be advantageously stored in more locations than would be possible with a constant geometry bioreactor and bioreactor 101 can also be gathered up when being autoclaved. Gathering up bioreactor 101 when bioreactor 101 is being autoclaved can mitigate damage inflicted on bioreactor 101 by the autoclave. Further still, because bioreactor cavity 102 can be maintained in a substantially (e.g., absolutely) axenic condition during operation of bioreactor 101, organism(s) vitally supported by bioreactor 101 can be vitally supported for extended lengths of time (e.g., as long as approximately three months) relative to organisms vitally supported at conventional bioreactors. Accordingly, in many examples, the frequency of stages at which the organism(s) of bioreactor 101 may need to be transferred to higher volume bioreactors compared to organisms vitally supported at conventional bioreactors can be reduced. For example, in some embodiments, organism(s) vitally supported by bioreactor 101 can be transferred directly to open air ponds rather than first needing to be progressively transferred between or among multiple bioreactors. Moreover, because bioreactor cavity 102 can be maintained in a substantially axenic condition during operation of bioreactor 101, bioreactor 101 can be particularly well suited for vitally supported genetically modified organisms, which may need to be isolated from competing organism(s) that have already naturally and/or optimally adapted to the environment until the genetically modified organisms are robust enough to survive. In many embodiments, the ability of bioreactor cavity 102 to be maintained in a substantially (e.g., absolutely) axenic condition during operation of bioreactor 101 can result from the ability to maintain bioreactor cavity 102 at least partially (e.g., fully) sealed after sterilization due to the configuration of bioreactor 101 and the conditions of operation of bioreactor 101 as described herein.

Notably, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be gathered up (e.g., folded up and/or rolled up) and autoclaved while being gathered up. By applying water to bioreactor cavity 102 during autoclaving, all surfaces of bioreactor 101 can be sterilized (e.g., autoclaved) despite bioreactor 101 being gathered up. That is, the advantages of gathering up bioreactor 101 during autoclaving may not detract from the ability of bioreactor 101 to be sterilized by being autoclaved.

Also advantageously, organism(s) being vitally supported by bioreactor 101 can achieve higher average densities and/or average maximum production rates than organism(s) vitally supported by conventional bioreactors. Average maximum production rate can refer to an increase in mass per unit volume per unit time (e.g., grams per liter per day) averaged across multiple similar or identical batches of organism(s) vitally supported by bioreactor 101. For example, the average maximum production rate for organism(s) taxonomically classified in taxonomic family Haematococcaceae can be based on multiple batches of organism(s) taxonomically classified in taxonomic family Haematococcaceae that are vitally supported by bioreactor 101. For example, in some embodiments, bioreactor 101 can vitally support organism(s) taxonomically classified in taxonomic family Haematococcaceae at an average density greater than or equal to approximately 12 grams per liter (e.g., approximately 13.34 grams per liter) or greater than or equal to approximately 14 grams per liter. In these or other embodiments, bioreactor 101 can vitally support organism(s) taxonomically classified in taxonomic family Haematococcaceae at an average maximum production rate of greater than or equal to approximately 2.5 grams per liter per day (e.g., approximately 2.78 grams per liter per day). Further, bioreactor 101 can vitally support organism(s) taxonomically classified in taxonomic family Chlorellaceae at an average density greater than or equal to approximately 36 grams per liter (e.g., approximately 40.3 grams per liter) or greater than or equal to approximately 50 grams per liter. In these or other embodiments, bioreactor 101 can vitally support organism(s) taxonomically classified in taxonomic family Chlorellaceae at an average maximum production rate of greater than or equal to approximately 9 grams per liter per day (e.g., approximately 9.86 grams per liter per day). Further still, bioreactor 101 can vitally support organism(s) taxonomically classified in taxonomic family Chlamydomonadaceae at an average density of greater than or equal to approximately 7 grams per liter (e.g., 7.63 grams per liter). In these or other embodiments, bioreactor 101 can vitally support organism(s) taxonomically classified in taxonomic family Chlamydomonadaceae at an average maximum production rate of greater than or equal to approximately 3 grams per liter per day (e.g., approximately 3.3 grams per liter per day). Notably, in these or other embodiments, the organism(s) can be harvested prior to achieving the foregoing average densities and/or average maximum production rates, and in some embodiments, the organism(s) can achieve higher average densities and/or average maximum production rates than the foregoing average densities and/or average maximum production rates.

In many embodiments, bioreactor cavity 102 can be inoculated (e.g., supplied) and/or re-inoculated with organism(s), such as, for example, while maintaining bioreactor cavity 102 in a substantially axenic or at least sterile condition. For example, in some embodiments, bioreactor cavity 102 can be inoculated (e.g., supplied) and/or re-inoculated with organism(s) using a sterile volume of a polymerase chain reaction (PCR) laminar flow hood or another implement configured to provide a sterile volume in which to work. In many embodiments, bioreactor cavity 102 can be inoculated (e.g., supplied) and/or re-inoculated with organism(s) in a similar or identical manner.

In many embodiments, the sterile volume of the PCR laminar flow hood can be prepared for use by wiping down the sterile volume with 70 percent ethanol one or more times and/or by irradiating the sterile volume with ultraviolet radiation for greater than or equal to approximately 30 minutes. In some embodiments, bioreactor 101 can be inflated with filtered (e.g., sterile) air to facilitate inoculation and/or installed in a support structure configured to mechanically support bioreactor 101. For example, the support structure can be similar or identical to support structure 323 (FIG. 3) and/or support structure 423 (FIG. 4).

In many embodiments, a filter assembly can be placed in the sterile volume of the PCR laminar flow hood. The filter assembly can be operable to filter the fluidic support medium when the fluidic support medium is transferred to bioreactor cavity 102. In these or other embodiments, the filter assembly can be stored in an autoclaved bag to maintain the filter assembly in sterile condition. When the filter assembly is stored in the autoclaved bag, the filter assembly can be removed from the autoclaved bag from within the sterile volume of the PCR laminar flow hood. The autoclaved bag can be sprayed with 70 percent ethanol prior to placement in the sterile volume of the PCR laminar flow hood.

In some embodiments, part of a bioreactor transfer tube can be sprayed with 70 percent ethanol nearest an input of the bioreactor transfer tube and that part of the bioreactor transfer tube can be placed in the sterile volume of the PCR laminar flow hood. The output of the bioreactor transfer tube can be coupled to an input of at least one of fluidic support medium delivery fitting(s) 110 in a sterile coupling. In many embodiments, the transfer tube can have been sterilized along with bioreactor 101 prior to inoculation of bioreactor 101. The input of the bioreactor transfer tube can be coupled to an output of the filter assembly within the sterile volume of the PCR laminar flow hood. In some embodiments, the bioreactor transfer tube can be coupled to an output of the filter assembly via one or more quick disconnects. The quick disconnects can be sprayed with 70 percent ethanol prior to coupling.

In some embodiments, an output of a fluidic support medium transfer tube can be fed through a peristaltic pump and can be coupled to an input of the filter assembly in the sterile volume of the PCR laminar flow hood. In some embodiments, the output of the fluidic support medium transfer tube can be coupled to the input of the filter assembly via one or more quick disconnects. In further embodiments, the quick disconnects can be sprayed with 70 percent ethanol prior to coupling. An input of the fluidic support medium transfer tube can be coupled to a fluidic support medium reservoir holding the fluidic support medium. Air can be purged from the peristaltic pump and/or the filter assembly and then the peristaltic pump can be operated to transfer the fluidic support medium through the fluidic support medium transfer tube, the filter assembly, the bioreactor transfer tube, and the at least one of fluidic support medium delivery fitting(s) 110 into bioreactor cavity 102.

In some embodiments, an output of an organism transfer tube can be fed through the peristaltic pump and can be coupled to the input of the bioreactor transfer tube in the sterile volume of the PCR laminar flow hood, such as, for example, via one or more quick disconnects. In many embodiments, the quick disconnects can be sprayed with 70 percent ethanol prior to coupling. In some embodiments, the part of the bioreactor transfer tube nearest the input of the bioreactor transfer tube can be sprayed with 70 percent ethanol and that part of the bioreactor transfer tube can be placed in the sterile volume of the PCR laminar flow hood. An input of the organism transfer tube can be coupled to an organism reservoir holding the organism(s), which may be in a nascent condition. The peristaltic pump can be operated to transfer the organisms through the organism transfer tube, the bioreactor transfer tube, and the at least one of fluidic support medium delivery fitting(s) 110 into bioreactor cavity 102.

Notably, in some embodiments, transfer of the fluidic support medium can be performed prior to transfer of the organism(s). However, in other embodiments, transfer of the organism(s) can be performed prior to the transfer of the fluidic support medium or simultaneously with the transfer of the fluidic support medium.

As previously introduced above, in many embodiments, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be autoclaved. For example, when being autoclaved, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be exposed to water elevated to high temperatures (e.g., temperatures in excess of approximately 121 or 134 degrees Celsius) as a result of the water being pressurized. Thus, in many embodiments, bioreactor 101 (e.g., bioreactor cavity 102, bioreactor wall(s) 103, bioreactor fitting(s) 104, gas delivery device(s) 105, flexible tube(s) 106, parameter sensing device(s) 109, and/or pressure regulator(s) 117) can be manufactured of materials able to resist these temperatures and pressures of water. Notably, methods for autoclaving bioreactor 101 can vary depending on the size of autoclave used.

In many embodiments, air can be purged from bioreactor 101 (e.g., via bioreactor exhaust tube(s)) using a vacuum pump. Further, any exterior tube(s) (e.g., the exhaust tube(s) and/or the bioreactor transfer tube) of bioreactor 101 can be coiled up and individually secured with autoclave tape. In various embodiments, bioreactor 101 can be gathered (e.g., folded and/or rolled up). For example, in some embodiments, bioreactor 101 can be rolled up from a top down along the length dimension of bioreactor 101. In other embodiments, bioreactor 101 can first be folded (e.g., in half) one or more times (e.g., about the length dimension of bioreactor 101) and then rolled up from a top down along the length dimension of bioreactor 101. In some embodiments, the coiled exterior tube(s) can be secured to bioreactor wall(s) 103 prior to gathering up bioreactor 101 or while gathering up bioreactor 101. In various embodiments, bioreactor 101 can be maintained in the gathered up configuration using autoclave tape and/or a heat welded strap of bioreactor wall material.

After gathering up bioreactor 101, bioreactor 101 can be placed in the autoclave. The autoclave can be operated to sterilize bioreactor 101. For example, the autoclave can be operated for approximately 45 minutes on an instrument or a liquid cycle.

Figure 2:
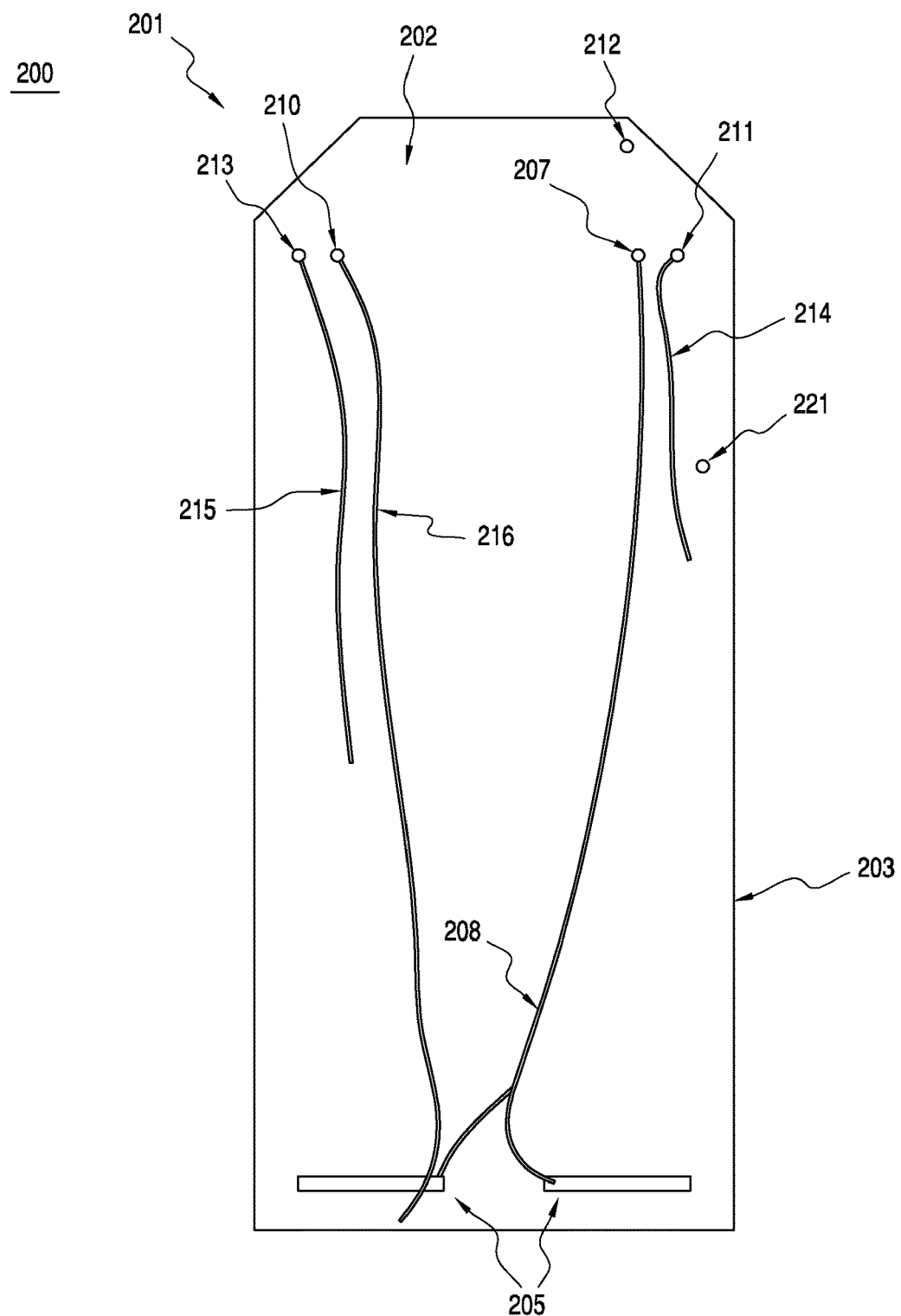
FIG. 2 illustrates a schematic side view of a system, according to an embodiment.

FIG. 2 illustrates a schematic side view of a system 200, according to an embodiment. System 200 can be similar or identical to system 100 (FIG. 1).

For example, system 200 can comprise bioreactor 201, bioreactor cavity 202, one or more bioreactor walls 203, one or more gas delivery devices 205, one or more gas delivery fittings 207, one or more gas delivery tubes 208, one or more fluidic support medium delivery fittings 210, one or more organic carbon material delivery fittings 211, one or more bioreactor exhaust fittings 212, one or more bioreactor sample fittings 213, one or more organic carbon material delivery tubes 214, one or more bioreactor sample tubes 215, one or more fluidic support medium delivery tubes 216, and one or more parameter sensing device fittings 221. In some embodiments, bioreactor 201 can be similar or identical to bioreactor 101 (FIG. 1); bioreactor cavity 202 can be similar or identical to bioreactor cavity 102 (FIG. 1); bioreactor wall(s) 203 can be similar or identical to bioreactor wall(s) 103 (FIG. 1); gas delivery device(s) 205 can be similar or identical to gas delivery device(s) 105 (FIG. 1); gas delivery fitting(s) 207 can be similar or identical to gas delivery fitting(s) 107 (FIG. 1); gas delivery tube(s) 208 can be similar or identical to gas delivery tube(s) 108 (FIG. 1); fluidic support medium delivery fitting(s) 210 can be similar or identical to fluidic support medium delivery fitting(s) 110 (FIG. 1); organic carbon material delivery fitting(s) 211 can be similar or identical to organic carbon material delivery fitting(s) 111 (FIG. 1); bioreactor exhaust fitting(s) 212 can be similar or identical to bioreactor exhaust fitting(s) 112 (FIG. 1); bioreactor sample fitting(s) 213 can be similar or identical to bioreactor sample fitting(s) 113 (FIG. 1); organic carbon material delivery tube(s) 214 can be similar or identical to organic carbon material delivery tube(s) 114 (FIG. 1); bioreactor sample tube(s) 215 can be similar or identical to bioreactor sample tube(s) 115 (FIG. 1); fluidic support medium delivery tube(s) 216 can be similar or identical to fluidic support medium delivery tube(s) 116 (FIG. 1); and/or parameter sensing device fitting(s) 221 can be similar or identical to parameter sensing device fitting(s) 121 (FIG. 1).

Tables 1-5 as follow illustrate various exemplary operational conditions under which bioreactor 101 (FIG. 1) and/or bioreactor 201 can be operated in order to vitally support exemplary taxonomically classified organisms.

TABLE 1

*Chlorella* sp.
(Mixotrophic Conditions)

| | |
|---|---|
| Organic Carbon Material | i) Option 1 (Mix of carbon and nitrogen) - Up to approximately 40% acetic acid and up to approximately 4% sodium nitrate; and ii) Option 2 (Mix of carbon and all nutrients) - Up to approximately 40% acetic acid, up to approximately 4% sodium nitrate, up to approximately 3.34 milligrams per liter trace metals solution, and up to approximately 6.67 milligrams per liter magnesium sulfate heptahydrate |
| Fluidic Support Medium | 2X modified BG-11 and approximately 100 microliters per liter Antifoam 204 |
| Nutritional Media Regimen | i) Implemented once culture density reaches approximately 5 grams per liter and approximately 15 grams per liter; ii) For Organic Carbon Material Option 1 - Add up to approximately 150 milligrams per liter magnesium sulfate heptahydrate, up to approximately 0.5 milliliters per liter trace metals, and up to approximately 200 milligrams per liter phosphate dibasic; and iii) For Organic Carbon Material Option 2 - Add up to approximately 200 milligrams per liter phosphate dibasic |
| Cavity Environment Conditions | i) pH - Approximately 7.5 ii) Temperature - Approximately 28 degrees Celsius |
| Lighting (e.g., both sides of bioreactor) | i) Either T-5 Fluorescent or light emitting diode; ii) For culture densities at or below approximately 0.5 grams per liter - Approximately 140 micro moles per/(meters$^2$ per second); and iii) For culture densities above approximately 0.5 grams per liter - Approximately 280 micro moles per/(meters$^2$ per second) |
| Aeration | i) Approximately 5 micron stainless steel air sparger; and ii) Approximately 60 liters per minute air flow rate |
| Substructure Frame Spacing (i.e., Bioreactor Depth) | Approximately 10.16 centimeters (e.g., Approximately 5.08 centimeters light path) |
| Partial Harvest Frequency | Approximately every 7 days |
| Partial Harvest Density | Approximately 20-30 grams per liter |

TABLE 2

*Haematococcus pluvialis*
(Mixotrophic conditions)

| | |
|---|---|
| Organic Carbon Material | i) Option 1 (Mix of carbon and nitrogen) - Up to approximately 20% acetic acid and up to approximately 2% sodium nitrate ii) Option 2 (carbon only) - Up to approximately 20% acetic acid |
| Fluidic Support Medium | Modified Microbio Media approximately 100 microliters per liter Antifoam 204 (mixture of organic polyether dispersions, available from Sigma Aldrich of St. Louis, Missouri, United States of America) |

TABLE 2-continued

*Haematococcus pluvialis*
(Mixotrophic conditions)

| | |
|---|---|
| Nutritional Media Regimen | i) Implemented each time the culture density increases by approximately 2-3 grams per liter;<br>ii) For first approximately 2-3 grams per liter increase - Add up to approximately 3.5 milliliters per liter nitrate stock, up to approximately 1.0 milliliters per liter trace metals stock, up to approximately 1.0 milliliters per liter iron stock, and up to approximately 1.5 milliliters per liter phosphate stock; and<br>iii) For additional approximately 2-3 grams per liter increases - Add up to approximately 1.0 milliliters per liter trace metals stock, up to approximately 1.0 milliliters per liter iron stock, and up to approximately 1.5 milliliters per liter phosphate stock |
| Cavity Environment Conditions | i) pH - Approximately 7.5<br>ii) Temperature - Approximately 25 degrees Celsius |
| Lighting (e.g., both sides of bioreactor) | i) Either T-5 Fluorescent or light emitting diode;<br>ii) For culture densities at or below approximately 0.5 grams per liter - Approximately 140 micro moles per/(meters$^2$ per second); and<br>iii) For culture densities above approximately 0.5 grams per liter - Approximately 280 micro moles per/(meters$^2$ per second) |
| Aeration | i) Approximately 5 micron stainless steel air sparger; or<br>ii) Flexible polymer air sparger |
| Substructure Frame Spacing (i.e., Bioreactor Depth) | Approximately 8.255 centimeters (4.1275 centimeters light path) |
| Partial Harvest Frequency | Approximately every 10-12 days |
| Partial Harvest Density | Approximately 7-10 grams per liter |

TABLE 3

*Scenedesmus* sp.
(Mixotrophic conditions)

| | |
|---|---|
| Organic Carbon Material | i) Option 1 (Mix of carbon and nitrogen) - Up to approximately 40% acetic acid and up to approximately 4% sodium nitrate; and<br>ii) Option 2 (carbon only) - Up to approximately 10 grams per liter glucose (feed batch) |
| Fluidic Support Medium | 2X modified BG-11 and approximately 100 microliters per liter Antifoam 204 |
| Nutritional Media Regimen | i) Implemented once culture density reaches approximately 5 grams per liter;<br>ii) Add up to approximately 150 milligrams per liter magnesium sulfate heptahydrate, up to approximately 0.5 milliliters per liter trace metals, and up to approximately 200 milligrams per liter potassium phosphate dibasic; and<br>iii) For Organic Carbon Material Option 2 ONLY - Add up to approximately 10 grams per liter glucose approximately every 3 grams per liter increase in culture density plus approximately 0.75X nitrate |
| Cavity Environment Conditions | i) pH - Approximately 7.5<br>ii) Temperature - Approximately 25 degrees Celsius |
| Lighting (e.g., both sides of bioreactor) | i) Either T-5 Fluorescent or light emitting diode;<br>ii) For culture densities at or below approximately 0.5 grams per liter - Approximately 140 micro moles per/(meters$^2$ per second); and<br>iii) For culture densities above approximately 0.5 grams per liter - Approximately 280 micro moles per/(meters$^2$ per second) |
| Aeration | i) (a) Approximately 5 micron stainless steel air sparger or (b) Flexible polymer air sparger; and<br>ii) 20 liters per minute air flow rate |
| Substructure Frame Spacing (i.e., Bioreactor Depth) | Approximately 10.16 centimeters (e.g., Approximately 5.08 centimeters light path) |
| Partial Harvest Frequency | Approximately every 7 days |
| Partial Harvest Density | Approximately 7-12 grams per liter |

TABLE 4

*Porphyridium* sp.
(Phototrophic conditions)

| | |
|---|---|
| Organic Carbon Material | None |
| Fluidic Support Medium | i) Modified f/2 and approximately 100 microliters per liter Antifoam 204 |
| Nutritional Media Regimen | i) Implemented once culture density reaches approximately 5 grams per liter; and |
| | ii) Add up to approximately 150 milligrams per liter magnesium sulfate heptahydrate, up to approximately 0.5 milliliters per liter trace metals, and up to approximately 200 milligrams per liter potassium phosphate dibasic |
| Cavity Environment Conditions | i) pH - Approximately 7.5 |
| | ii) Temperature - Approximately 25 degrees Celsius |
| Lighting (e.g., both sides of bioreactor) | i) Either T-5 Fluorescent or light emitting diode; |
| | ii) For culture densities at or below approximately 0.5 grams per liter - Approximately 140 micro moles per/(meters$^2$ per second); and |
| | iii) For culture densities above approximately 0.5 grams per liter - Approximately 280 micro moles per/(meters$^2$ per second) |
| Aeration | i) Flexible polymer air sparger; and |
| | ii) 30 liters per minute air flow rate |
| Substructure Frame Spacing (i.e., Bioreactor Depth) | Approximately 10.16 centimeters (e.g., Approximately 5.08 centimeters light path) |
| Partial Harvest Frequency | As needed |
| Partial Harvest Density | Approximately 1.5-2.5 grams per liter |

TABLE 5

*Chlamydomonas* sp.
(Mixotrophic conditions)

| | |
|---|---|
| Organic Carbon Material | Up to approximately 20% acetic acid and up to approximately 22 grams per liter ammonium bicarbonate |
| Fluidic Support Medium | Modified Bristol's Media and approximately 100 microliters per liter Antifoam 204 |
| Nutritional Medi Regimen | None |
| Cavity Environment Conditions | i) pH - Approximately 7.5 |
| | ii) Temperature - Approximately 25 degrees Celsius |
| Lighting (e.g., both sides of bioreactor) | i) Either T-5 Fluorescent or light emitting diode; |
| | ii) For culture densities at or below approximately 0.5 grams per liter - Approximately 140 micro moles per/(meters$^2$ per second); and |
| | iii) For culture densities above approximately 0.5 grams per liter - Approximately 280 micro moles per/(meters$^2$ per second) |
| Aeration | i) Approximately 5 micron stainless steel air sparger; and |
| | ii) Approximately 20 liters per minute air flow rate |
| Substructure Frame Spacing (i.e., Bioreactor Depth) | Approximately 10.16 centimeters (e.g., Approximately 5.08 centimeters light path) |
| Partial Harvest Frequency | None (Full harvest) |
| Partial Harvest Density | Approximately 2-5 grams per liter |

Figure 3:
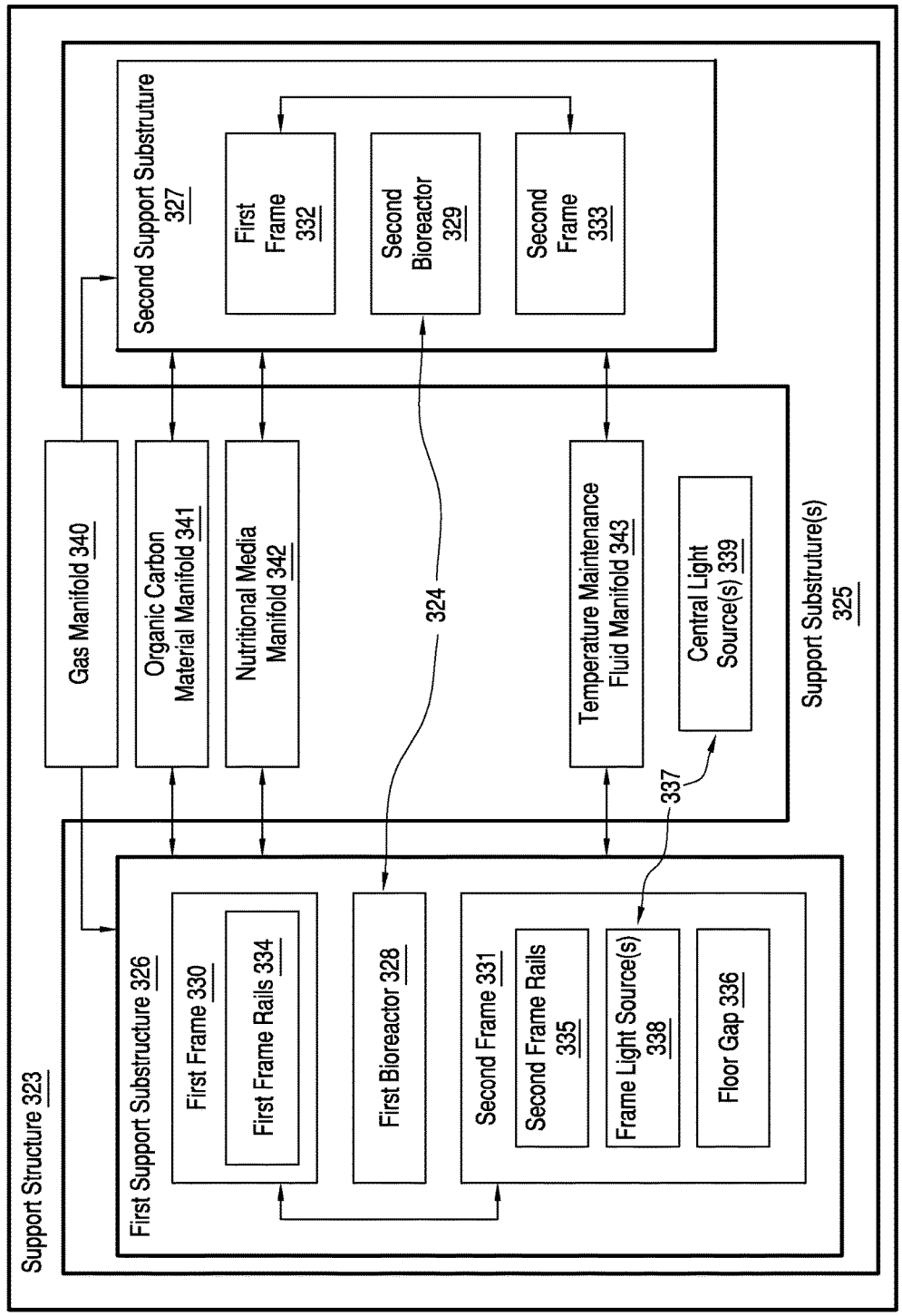
FIG. 3 illustrates an exemplary block diagram of a system, according to an embodiment.
Figure 4:
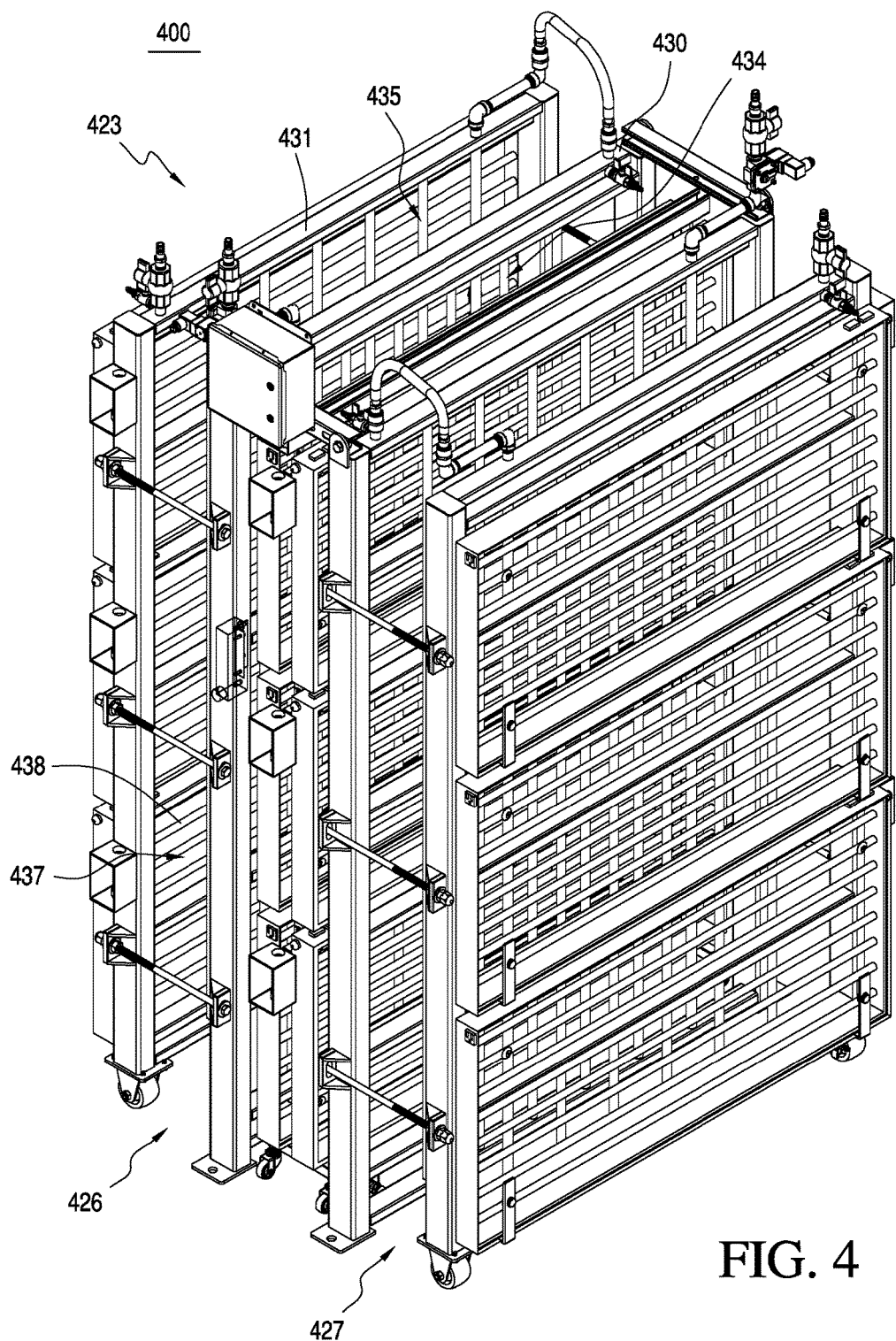
FIG. 4 illustrates a system, according to an embodiment.

Turning ahead now in the drawings, FIG. 3 illustrates an exemplary block diagram of a system 300, according to an embodiment. System 300 is merely exemplary and is not limited to the embodiments presented herein. System 300 can be employed in many different embodiments or examples not specifically depicted or described herein.

System 300 comprises a support structure 323. As explained in greater detail below, support structure 323 is operable to mechanically support one or more bioreactors 324. In these or other embodiments, as also explained in greater detail below, support structure 323 can be operable to maintain a set point temperature of one or more of bioreactor(s) 324, such as, for example, through an exchange of thermal energy between support structure 323 and one or more of bioreactor(s) 324. In many embodiments, one or more of bioreactor(s) 324 can be similar or identical to bioreactor 101 (FIG. 1) and/or bioreactor 201 (FIG. 2). Accordingly, the term set point temperature can refer to the set point temperature as defined above with respect to system 100 (FIG. 1). Further, when bioreactor(s) 324 comprise multiple bioreactors, two or more of bioreactor(s) 324 can be similar or identical to each other and/or two or more of bioreactor(s) 324 can be different form each other. For example, the bioreactor wall materials of the bioreactor walls of two or more of bioreactor(s) 324 can be different. In some embodiments, system 300 can comprise one or more of bioreactor(s) 324.

In many embodiments, support structure 323 comprises one or more support substructures 325. Each support substructure of support substructure(s) 325 can mechanically support one bioreactor of bioreactor(s) 324. In these or other embodiments, each support substructure of support substructure(s) 325 can maintain a set point temperature of one bioreactor of bioreactor(s) 324, such as, for example, through an exchange of thermal energy between the support substructure and the bioreactor. In further embodiments, each of support substructure(s) 325 can be similar or identical to each other.

For example, support substructure(s) 325 can comprise a first support substructure 326 and a second support substructure 327. In these embodiments, first support substructure 326 can mechanically support a first bioreactor 328 of bioreactor(s) 324, and second support substructure 327 can mechanically support a second bioreactor 329 of bioreactor(s) 324. Further, first support substructure 326 can comprise a first frame 330 and a second frame 331, and second support substructure 327 can comprise a first frame 332 and a second frame 333. In many embodiments, first frame 330 can be similar or identical to first frame 332, and second frame 331 can be similar or identical to second frame 333. Further, first frame 330 can be similar to second frame 331, and first frame 332 can be similar to second frame 333.

As indicated above, first support substructure 326 can be similar or identical to second support substructure 327. Accordingly, to increase the clarity of the description of system 300 generally, the description of second support substructure 327 is limited so as not to be redundant with respect to first support substructure 326.

In many embodiments, first frame 330 and second frame 331 together can mechanically support first bioreactor 328 in interposition between first frame 330 and second frame 331. That is, bioreactor 328 can be sandwiched between first frame 330 and second frame 331 at a slot formed between first frame 330 and second frame 331. In these or other embodiments, first frame 330 and second frame 331 together can mechanically support first bioreactor 328 in an approximately vertical orientation. Further, first frame 330 and second frame 331 can be oriented approximately parallel to each other.

In many embodiments, second frame 331 can be selectively moveable relative to first frame 330 so that the volume of the slot formed between first frame 330 and second frame 331 can be adjusted. For example, second frame 331 can be supported by one or more wheels permitting second frame 331 to be rolled closer to or further from first frame 330. Meanwhile, in these or other embodiments, second frame 331 can be coupled to first frame 330 by one or more adjustable coupling mechanisms. The adjustable coupling mechanism(s) can hold second frame 331 in a desired position relative to first frame 330 while being adjustable so that the position can be changed when desirable. In implementation, the adjustable coupling mechanism(s) can comprise one or more threaded screws extending between first frame 330 and second frame 331, such as, for example, in a direction orthogonal to first frame 330 and second frame 331. Turning the threaded screws can cause second frame 331 to move (e.g., on the wheel(s)) relative to first frame 330.

Meanwhile, in some embodiments, first frame 330 can be operable to maintain a set point temperature of first bioreactor 328 when first bioreactor 328 is operating to vitally support one or more organisms and when support structure 323 (e.g., first support substructure 326, first frame 330, and/or second frame 331) is mechanically supporting first bioreactor 328. In these or other embodiments, second frame 331 can be operable to maintain the set point temperature of first bioreactor 328 when first bioreactor 328 is operating to vitally support the organism(s) and when support structure 300 (e.g., second support substructure 327, first frame 330, and/or second frame 331) is mechanically supporting first bioreactor 328. Support structure 323, first frame 330, and/or second frame 331 can be operable to maintain the set point temperature of first bioreactor 328 through an exchange of thermal energy between support structure 323, first frame 330, and/or second frame 331 and first bioreactor 328.

In many embodiments, first frame 330 can comprise multiple first frame rails 334. First frame rails 334 can be approximately planar to each other and/or can be spaced at regular or irregular intervals relative to each other. Accordingly, first frame rails 334 can resemble pickets in a fence-like arrangement configured to mechanically support first bioreactor 328. Further, each frame rail of first frame rails 334 can comprise a hollow conduit. First frame rails 334 can be configured to receive and convey a temperature maintenance fluid at the hollow conduits. By conveying the temperature maintenance fluid through the hollow conduits of first frame rails 334 while first frame 330 mechanically supports first bioreactor 328, thermal energy can be transferred between first bioreactor 328 and the temperature maintenance fluid. For example, the temperature maintenance fluid can be chilled to lower a temperature of first bioreactor 328 or heated to raise a temperature of first bioreactor 328 in order to maintain the set point temperature of first bioreactor 328 when first bioreactor 328 is vitally supporting one or more organism(s). In these or other embodiments, thermal energy can be transferred from the temperature maintenance fluid to first frame 330 and from first frame 330 to first bioreactor 328, such as, for example, then the temperature maintenance fluid is used to raise the temperature of first bioreactor 328, or thermal energy can be transferred from first bioreactor 328 to first frame 330 and from first frame 330 to the temperature maintenance fluid, such as, for example, then the temperature maintenance fluid is used to lower the temperature of first bioreactor 328.

In many embodiments, two or more of the hollow conduits of first frame rails 334 can be coupled together, such as, for example, so that the two or more hollow conduits of first frame rails 334 can receive the temperature maintenance fluid from a same temperature maintenance source. In these or other embodiments, two or more of the hollow conduits of first frame rails 334 can receive the temperature maintenance fluid serially and/or two or more of the hollow conduits of first frame rails 334 can receive the temperature maintenance fluid in parallel. Configuring two or more of the hollow conduits of first frame rails 334 to receive the temperature maintenance fluid in parallel can be advantageous because a total path that a given volume of the temperature maintenance fluid takes through the hollow conduits of first frame rails 334 can be reduced. As a result, the temperature of the given volume of the temperature maintenance fluid can remain closer to a starting temperature of the given volume of the temperature maintenance fluid. That is, as the path length that the given volume of the temperature maintenance fluid increases, so too does the amount of time that the given volume of the temperature maintenance fluid undergoes thermal energy transfer with bioreactor 324. Meanwhile, minimizing the temperature flux in the temperature maintenance fluid can permit the set point temperature of bioreactor 324 to be more accurately maintained. To further minimize the temperature flux, the temperature maintenance fluid can be forced upward (e.g., against gravity) into and through first frame rails 334 from the temperature maintenance source.

In implementation, first frame rails 334 can comprise two or more pipes. First frame rails 334 (e.g., the pipes) can comprise one or more frame rail materials able to mechanically support bioreactor 324 while facilitating thermal energy transfer between the temperature maintenance fluid and bioreactor 324. In many embodiments, the frame rail material(s) can also be selected so as to minimally chemically react with the temperature maintenance fluid. For example, the frame rail material(s) can comprise metal (e.g., stainless steel, copper, etc.). In these or other examples, the temperature maintenance fluid can comprise water. Meanwhile, in many embodiments, first frame 330 can comprise one or more perimeter beams configured to reinforce (e.g., frame) first frame rails 334. In these embodiments, the perimeter beams can comprise one or more beam materials able to mechanically support bioreactor 324. In many embodiments, first frame 330 can also be bolted to the ground for support.

As indicated above, in many embodiments, in many embodiments, second frame 331 can be similar or identical to first frame 330. Accordingly, second frame 331 can comprise multiple second frame rails 335. Meanwhile, second frame rails 335 can be similar or identical to first frame rails 334. In some embodiments, the hollow conduits of first frame rails 334 can be coupled to hollow conduits of 335. In these embodiments, the hollow conduits of first frame rails 334 and second frame rails 335 can receive the temperature maintenance fluid from the same source. However, in these or other embodiments, the hollow conduits of first frame rails 334 and the hollow conduits of second frame rails 335 can receive the temperature maintenance fluid from different sources.

In many embodiments, first support substructure 326 comprises a floor gap 336. Floor gap 336 can be located underneath one of first frame 330 or second frame 331. Floor gap 336 can permit first bioreactor 328 to bulge into floor gap 336 past first support substructure 326 when first support substructure 326 is mechanically supporting first bioreactor 328. Permitting first bioreactor 328 to bulge into floor gap 336 can relieve stress from first bioreactor 328. For example, in many embodiments, bioreactor(s) 324 can experience the greatest amount of stress at their base(s) when being mechanically supported in a vertical position, such as, for example, by support structure 323. In these embodiments, permitting first bioreactor 328 to bulge into floor gap 336 such that first support substructure 326 is not restraining first bioreactor 328 at floor gap 336 can relieve more stress from first bioreactor 328 than constraining all of first bioreactor 328 at both sides with first frame 330 and second frame 331, even if first frame 330 and second frame 331 are reinforced.

System 300 (e.g., support structure 323) can comprise one or more light sources 337. Light source(s) 337 can be operable to illuminate the organism(s) being vitally supported at bioreactor(s) 324. In many embodiments, second frame 331 can comprise and/or mechanically support one or more frame light source(s) 338 of light source(s) 337. Meanwhile, system 300 (e.g., support structure 323) can comprise one or more central light source(s) 339. In these or other embodiments, support substructure(s) 325 (e.g., first support substructure 326 and second support substructure 327) can be mirrored about a central vertical plane of support structure 323. Accordingly, central light source(s) 339 can be interpositioned between first support substructure 326 and second support substructure 327 so that first bioreactor 328 and second bioreactor 329 each can receive light from central light source(s) 339.

In implementation, light source(s) 337 (e.g., frame light source(s) 338 and/or central light source(s) 339) can comprise one or more banks of light bulbs and/or light emitting diodes. In some embodiments, light source(s) 337 (e.g., the light bulbs and/or light emitting diodes) can emit one or more wavelengths of light, as desirable for the particular organism(s) being vitally supported by bioreactor(s) 324.

Advantageously, because each support substructure of support substructure(s) 325 can maintain a set point temperature of different ones of bioreactor(s) 324, each of bioreactor(s) 324 can be maintained at a set point temperature independently of each other. For example, when bioreactor(s) 324 are vitally supporting different types of organism(s), bioreactor(s) 324 can comprise different set point temperatures. Nonetheless, in many embodiments, bioreactor(s) 324 can comprise the same set point temperatures.

Meanwhile, in many embodiments, system 300 can comprise gas manifold 340, organic carbon material manifold 341, nutritional media manifold 342, and/or temperature maintenance fluid manifold 343. Gas manifold 340 can be operable to provide gas to one or more gas delivery fittings of bioreactor(s) 324. The gas delivery fitting(s) can be similar or identical to gas delivery fitting(s) 107 (FIG. 1) and/or gas delivery fitting(s) 207 (FIG. 2). Further, organic carbon material manifold 341 can be operable to deliver organic carbon material to one or more organic carbon material delivery fittings of bioreactor(s) 324. The organic carbon material delivery fitting(s) can be similar or identical to organic carbon material delivery fitting(s) 111 (FIG. 1) and/or organic carbon material delivery fitting(s) 211 (FIG. 2). Further still, nutritional media manifold 342 can be operable to provide nutritional media to one or more fluidic support medium delivery fittings of bioreactor(s) 324. The fluidic support medium delivery fitting(s) can be similar or identical to fluidic support medium delivery fitting(s) 110 (FIG. 1) and/or fluidic support medium delivery fitting(s) 210 (FIG. 2). Meanwhile, temperature maintenance fluid manifold can be configured to provide the temperature maintenance fluid to the hollow conduits of first frame 330 and/or second frame 331.

Gas manifold 340, organic carbon material manifold 341, nutritional media manifold 342, and/or temperature maintenance fluid manifold 343 each can comprise one or more tubes, one or more valves, one or more gaskets, one or more reservoirs, one or more pumps, and/or control logic (e.g., one or more computer processors, one or more transitory memory storage modules, and/or one or more non-transitory memory storage modules) configured to perform their respective functions. In these embodiments, the control logic can communicate with one or more parameter sensing devices of bioreactor(s) 324 to determine when to perform their respective functions (i.e., according to the needs of the organism(s) being vitally supported by bioreactor(s) 324). The parameter sensing device(s) can be similar or identical to parameter sensing device(s) 109 (FIG. 1).

In some embodiments, bioreactor(s) 324 can be positioned and/or at least partially sealed in one or more containment vessels while support structure 323 is mechanically supporting bioreactor(s) 324. Each of the containment vessel(s) can be similar or identical to the containment vessel described above with respect to bioreactor 101 (FIG. 1). In many embodiments, the containment vessel(s) can be filled with a containment vessel fluid to provide additional mechanical support for bioreactor(s) 324 while support structure 323 is mechanically supporting bioreactor(s) 324. The containment vessel fluid can be similar or identical to the containment vessel fluid described above with respect to bioreactor 101 (FIG. 1).

Turning to the next drawing, FIG. 4 illustrates a system 400, according to an embodiment. System 400 can be similar or identical to system 300 (FIG. 3).

For example, system 400 can comprise support structure 423, first support substructure 426, second support substructure 427, first frame 430, second frame 431, first frame rails 434, second frame rails 435, and one or more light source(s) 437. In these embodiments, light source(s) 437 can comprise one or more frame light sources 438. In many embodiments, support structure 423 can be similar or identical to support structure 323 (FIG. 3); first support substructure 426 can be similar or identical to first support substructure 326 (FIG. 3); second support substructure 427 can be similar or identical to second support substructure 327 (FIG. 3); first frame 430 can be similar or identical to first frame 330 (FIG. 3); second frame 431 can be similar or identical to second frame 331 (FIG. 3); first frame rails 434 can be similar or identical to first frame rails 334 (FIG. 3); second frame rails 435 can be similar or identical to second frame rails 335 (FIG. 3); and/or light source(s) 437 can be similar or identical to light source(s) 337 (FIG. 3). Further, frame light source(s) 438 can be similar or identical to frame light source(s) 338.

Figure 5:
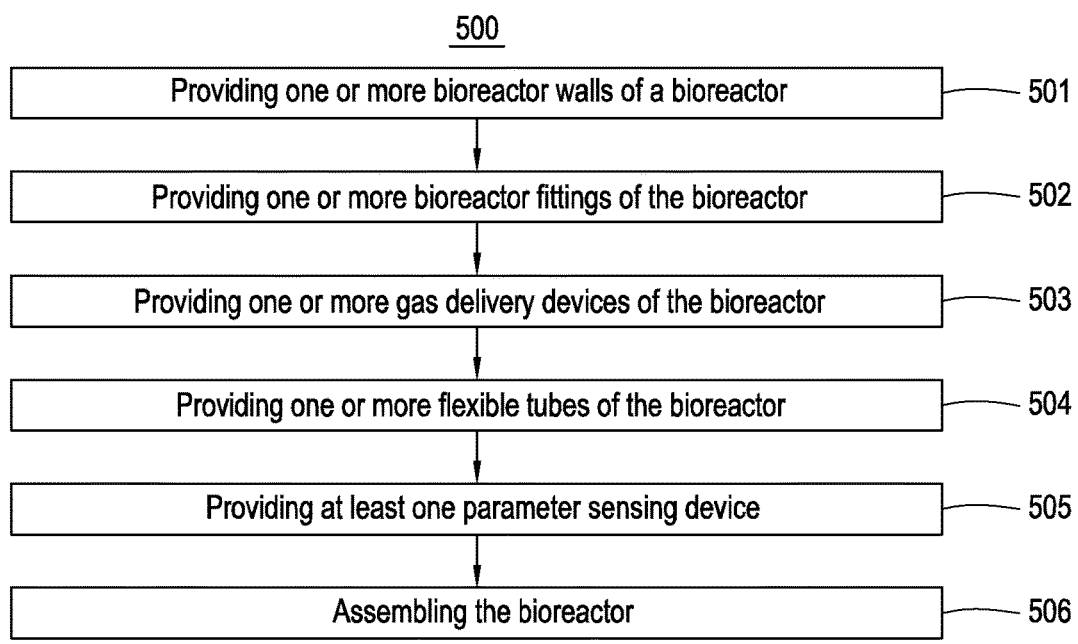
FIG. 5 illustrates a flow chart for an embodiment of a method.

Turning ahead again in the drawings, FIG. 5 illustrates a flow chart for an embodiment of a method 500. In some embodiments, method 500 can comprise a method of providing a system. The system can be similar or identical to system 100 (FIG. 1) and/or system 200 (FIG. 2). Method 500 is merely exemplary and is not limited to the embodiments presented herein. Method 500 can be employed in many different embodiments or examples not specifically depicted or described herein. In some embodiments, the activities of method 500 can be performed in the order presented. In other embodiments, the activities of method 500 can be performed in any other suitable order. In still other embodiments, one or more of the activities of method 500 can be combined or skipped.

In many embodiments, method 500 can comprise activity 501 of providing one or more bioreactor walls of a bioreactor. In these or other embodiments, the bioreactor wall(s) can be similar or identical to bioreactor wall(s) 103 (FIG. 1) and/or bioreactor wall(s) 203 (FIG. 2). Further, the bioreactor can be similar or identical to bioreactor 101 (FIG. 1) and/or bioreactor 201 (FIG. 2).

Figure 14:
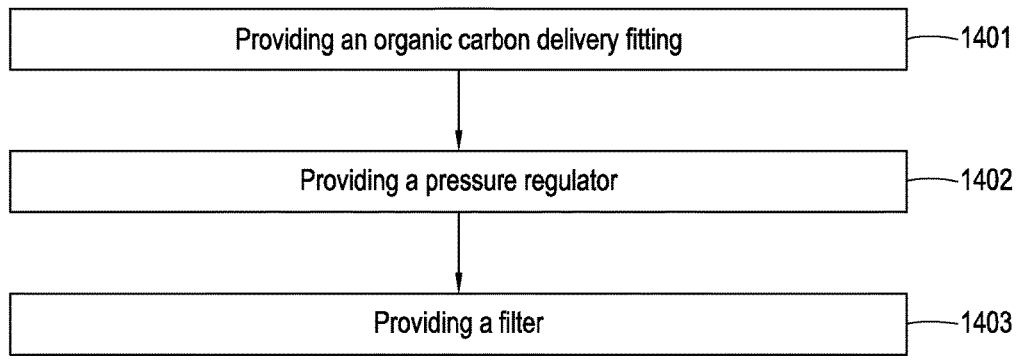
FIG. 14 illustrates a flow chart for an exemplary activity of providing one or more bioreactor fittings of a bioreactor, according to the method of FIG. 13.

In some embodiments, method 500 can comprise activity 502 of providing one or more bioreactor fittings of the bioreactor. In these or other embodiments, the bioreactor fitting(s) can be similar or identical to bioreactor fitting(s) 104 (FIG. 1). FIG. 14 illustrates an exemplary activity 502, according to the embodiment of FIG. 5.

For example, activity 502 can comprise activity 1401 of providing an organic carbon delivery fitting. In these or other embodiments, the organic carbon material delivery fitting can be similar or identical to one of organic carbon material delivery fitting(s) 111 (FIG. 1).

Further, activity 502 can comprise activity 1402 of providing a pressure regulator. In these or other embodiments, the pressure regulator can be similar or identical to one of pressure regulator(s) 117.

Further still, activity 502 can comprise activity 1403 of providing a filter. In these or other embodiments, the filter can be similar or identical to one of the filters described above with respect to system 100 (FIG. 1).

Referring now back to FIG. 5, in some embodiments, method 500 can comprise activity 503 of providing one or more gas delivery devices of the bioreactor. In these or other embodiments, the gas delivery device(s) can be similar or identical to gas delivery device(s) 105 (FIG. 1) and/or gas delivery device(s) 205 (FIG. 2).

In some embodiments, method 500 can comprise activity 504 of providing one or more flexible tubes of the bioreactor. In these or other embodiments, the flexible tube(s) can be similar or identical to flexible tube(s) 106 (FIG. 1). For example, in many embodiments, performing activity 504 can comprise providing an organic carbon material delivery tube of the one or more flexible tubes of the bioreactor. In some embodiments, the organic carbon material delivery tube can be similar or identical to one of organic carbon material delivery tube(s) 114 (FIG. 1) and/or organic carbon material delivery tube 214 (FIG. 2).

In some embodiments, method 500 can comprise activity 505 of providing at least one parameter sensing device. In these or other embodiments, the parameter sensing device(s) can be similar or identical to parameter sensing device(s) 109 (FIG. 1).

Figure 15:
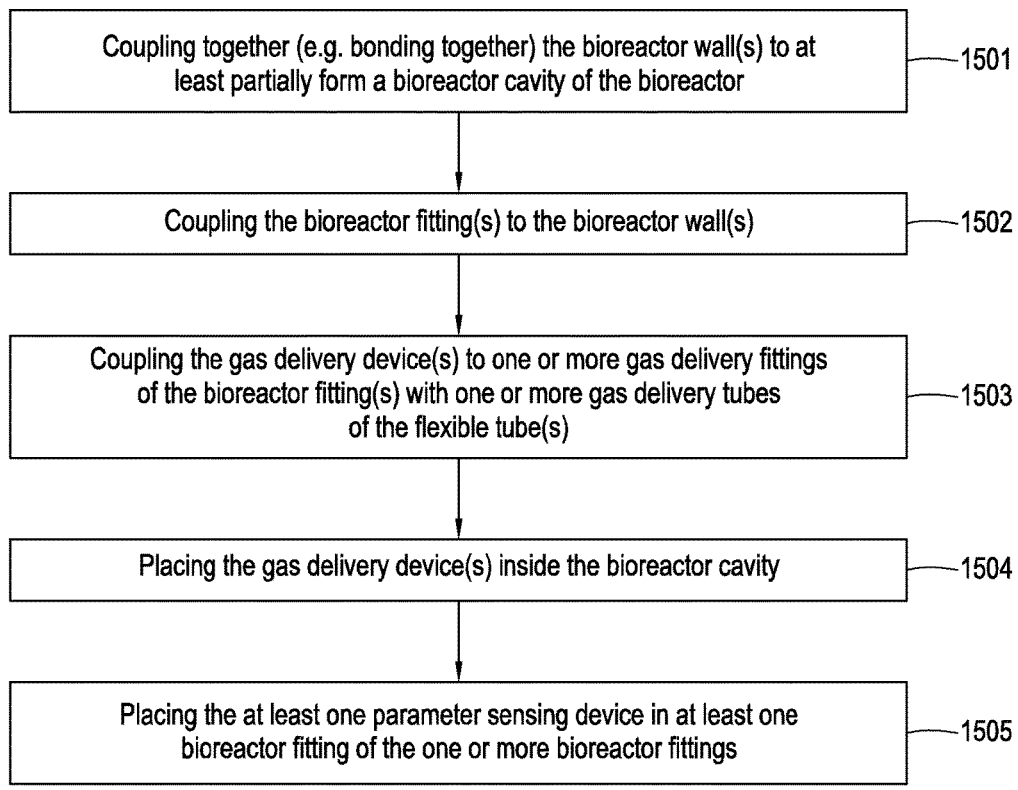
FIG. 15 illustrates a flowchart for an exemplary activity of assembling the bioreactor, according to the method of FIG. 13.

In some embodiments, method 500 can comprise activity 506 of assembling the bioreactor. In these or other embodiments, performing activity 506 can be similar or identical to assembling bioreactor 101 (FIG. 1) as described above with respect to system 100 (FIG. 1). FIG. 15 illustrates an exemplary activity 506, according to the embodiment of FIG. 5.

For example, activity 506 can comprise activity 1501 of coupling together (e.g., bonding together) the bioreactor wall(s) to at least partially form a bioreactor cavity of the bioreactor. In many embodiments, performing activity 1501 can be performed similarly or identically to coupling together bioreactor wall(s) 103 (FIG. 1) to at least partially form bioreactor cavity 102 (FIG. 1) of bioreactor 101 (FIG. 1) as described above with respect to system 100 (FIG. 1). For example, activity 1501 can comprise heat welding together the bioreactor wall(s) to at least partially form the bioreactor cavity of the bioreactor.

In some embodiments, activity 506 can comprise activity 1502 of coupling the bioreactor fitting(s) to the bioreactor wall(s). In some embodiments, activity 1502 can be performed before, after, or approximately simultaneously with activity 1502. Meanwhile, in many embodiments, performing activity 1502 can be similar or identical to coupling bioreactor fitting(s) 104 (FIG. 1) to the bioreactor wall(s) 103 (FIG. 1) as described above with respect to system 100 (FIG. 1).

In some embodiments, activity 506 can comprise activity 1503 of coupling the gas delivery device(s) to one or more gas delivery fittings of the bioreactor fitting(s) with one or more gas delivery tubes of the flexible tube(s). In these embodiments, the gas delivery fitting(s) can be similar or identical to gas delivery fitting(s) 105 (FIG. 1) and/or gas delivery fitting(s) 205 (FIG. 2); and/or the gas delivery tube(s) can be similar or identical to gas delivery tube(s) 106 (FIG. 1) and/or gas delivery tube(s) 206 (FIG. 2). In some embodiments, activity 1503 can be performed before, after, or approximately simultaneously with activity 1501 and/or activity 1502.

In some embodiments, activity 506 can comprise activity 1504 of placing the gas delivery device(s) inside the bioreactor cavity. In these embodiments, activity 1504 can be performed before activity 1501 is completed.

In some embodiments, activity 506 can comprise activity 1505 of placing the at least one parameter sensing device in at least one bioreactor fitting of the one or more bioreactor fittings. In many embodiments, performing activity 1505 can be similar or identical to placing parameter sensing device(s) 109 (FIG. 1) in at least one bioreactor fitting of bioreactor fitting(s) 104 (FIG. 1).

Figure 6:
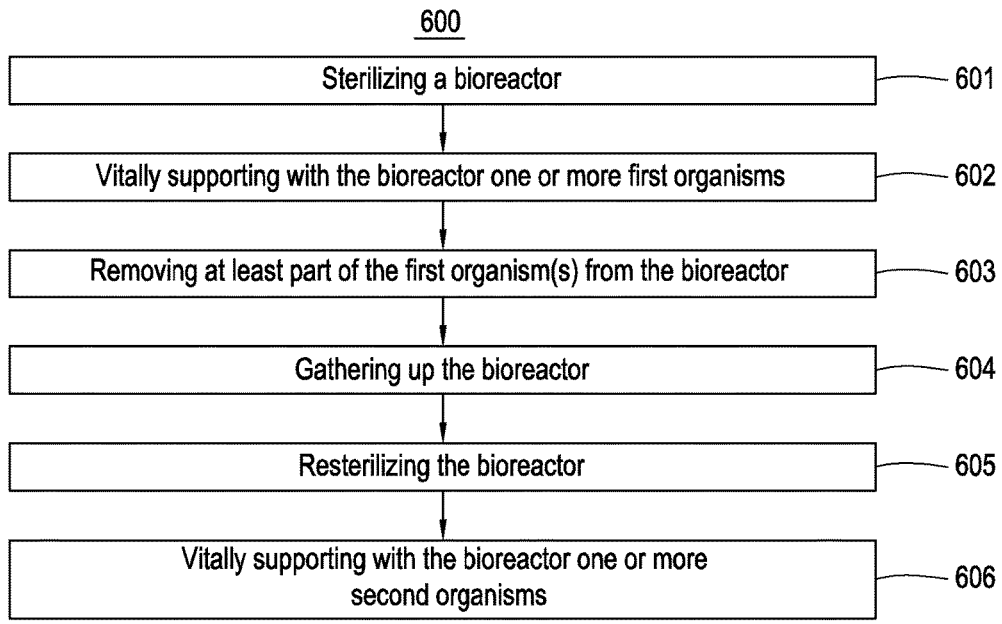
FIG. 6 illustrates a flow chart for an embodiment of a method.

Turning ahead again in the drawings, FIG. 6 illustrates a flow chart for an embodiment of a method 600. Method 600 is merely exemplary and is not limited to the embodiments presented herein. Method 600 can be employed in many different embodiments or examples not specifically depicted or described herein. In some embodiments, the activities of method 600 can be performed in the order presented. In other embodiments, the activities of method 600 can be performed in any other suitable order. In still other embodiments, one or more of the activities of method 600 can be combined or skipped.

Figure 7:
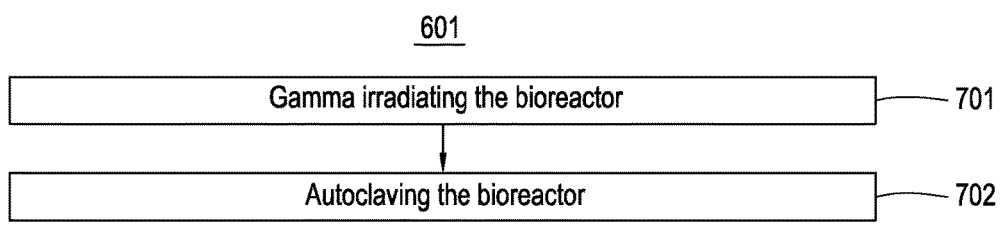
FIG. 7 illustrates a flow chart of an exemplary activity of sterilizing a bioreactor, according to the embodiment of FIG. 6.

In many embodiments, method 600 can comprise activity 601 of sterilizing a bioreactor. In these embodiments, the bioreactor can be similar or identical to bioreactor 101 (FIG. 1) and/or bioreactor 201 (FIG. 2). FIG. 7 illustrates a flow chart of an exemplary activity 601, according to the embodiment of FIG. 6.

For example, activity 601 can comprise activity 701 of gamma irradiating the bioreactor. In many embodiments, activity 701 can be performed by exposing the bioreactor to a radioactive isotope configured to emit gamma radiation.

In some embodiments, activity 601 can comprise activity 702 of autoclaving the bioreactor. Activity 702 can be performed similarly or identically to autoclaving bioreactor 101 (FIG. 1) as described above with respect to system 100 (FIG. 1). In some embodiments, activity 701 can be omitted when activity 702 is performed, or vice versa. In other embodiments, both activity 701 and activity 702 can be performed.

Figure 8:
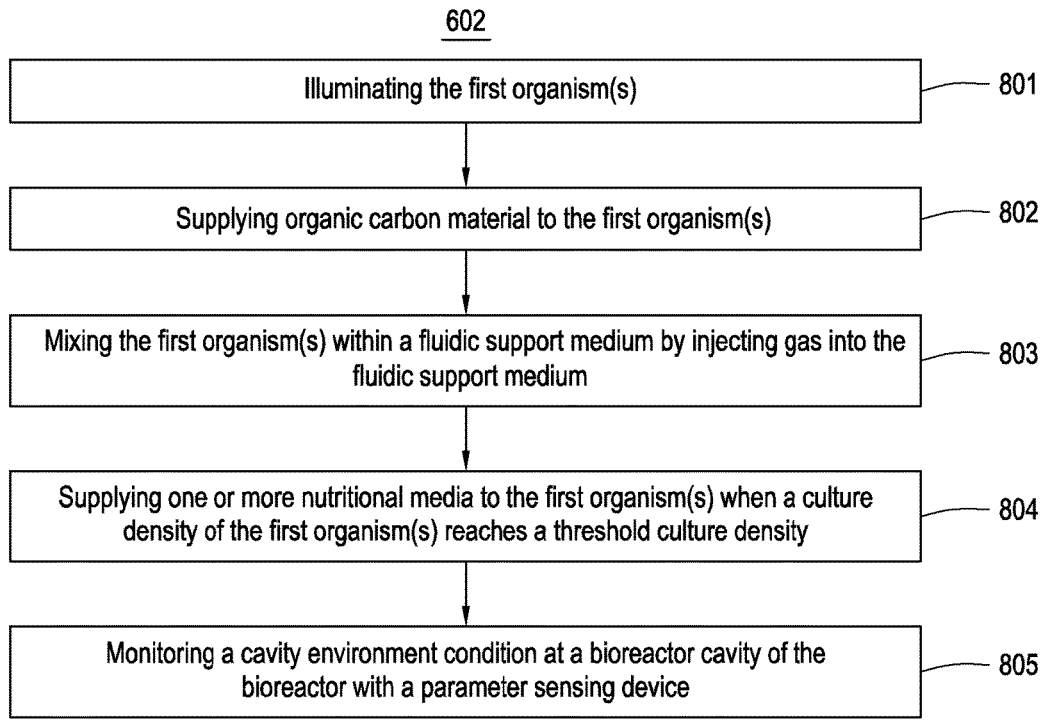
FIG. 8 illustrates a flow chart of an exemplary activity of vitally supporting with the bioreactor one or more first organisms, according to the embodiment of FIG. 6

Referring now back to FIG. 6, method 600 can comprise activity 602 of vitally supporting with the bioreactor one or more first organisms. In these embodiments, the first organism(s) can be similar or identical to the organism(s) described above with respect to system 100 (FIG. 1). Further, activity 602 can be performed similarly or identically to vitally supporting one or more organisms with bioreactor 101 (FIG. 1) as described above with respect to system 100 (FIG. 1). In many embodiments, activity 602 can be performed after activity 601. FIG. 8 illustrates a flow chart of an exemplary activity 602, according to the embodiment of FIG. 6.

For example, activity 602 can comprise activity 801 of illuminating the first organism(s). In many embodiments, activity 801 can be performed using one or more light source(s), which can be similar or identical to light source(s) 337 (FIG. 3) and/or light source(s) 437 (FIG. 4). In some embodiments, performing activity 801 can comprise supplying a quantity of light to the first organism(s) based on a culture density of the first organism(s). In some embodiments, activity 801 can be omitted, such as, for example, when the first organism(s) are not phototrophic organism(s).

In some embodiments, activity 602 can comprise activity 802 of supplying organic carbon material to the first organism(s). Activity 802 can be performed similarly or identically to supplying organic carbon material to the organism(s) as described above with respect to system 100 (FIG. 1). Further, the organic carbon material can be similar or identical to the organic carbon material described above with respect to system 100 (FIG. 1). In some embodiments, activity 802 can be omitted, such as, for example, when the first organism(s) comprise autotrophic organism(s).

In many embodiments, activity 602 can comprise activity 803 of mixing the first organism(s) within a fluidic support medium by injecting gas into the fluidic support medium. The fluidic support medium can be similar or identical to the fluidic support medium described above with respect to system 100 (FIG. 1). Further, the gas can be similar or identical to the gas described above with respect to gas delivery device(s) 105 (FIG. 1) of system 100 (FIG. 1). Further still, activity 803 can be performed similarly or identically to mixing the organism(s) within a fluidic support medium by injecting gas into the fluidic support medium as described above with respect to system 100 (FIG. 1).

In further embodiments, activity 602 can comprise activity 804 of supplying one or more nutritional media to the first organism(s) when a culture density of the first organism(s) reaches a threshold culture density. In some embodiments, performing activity 804 can be similar or identical to supplying one or more nutritional media to the first organism(s) when a culture density of the first organism(s) reaches a threshold culture density as described above with respect to system 100 (FIG. 1). The one or more nutritional media can be similar or identical to the one or more nutritional media described above with respect to system 100 (FIG. 1).

In some embodiments, activity 602 can comprise activity 805 of monitoring a cavity environment condition at a bioreactor cavity of the bioreactor with a parameter sensing device. The bioreactor cavity can be similar or identical to bioreactor cavity 102 (FIG. 1) and/or bioreactor cavity 202 (FIG. 2); and/or the parameter sensing device can be similar or identical to one of parameter sensing device(s) 109 (FIG. 1).

In some embodiments, activity 602 can comprise activity 806 of operating the bioreactor in substantially axenic conditions. In many embodiments, activity 806 can be performed simultaneously with one or more of activities 801-805.

Referring back to FIG. 6, method 600 can comprise activity 603 of removing at least part of the first organism(s) from the bioreactor. In many embodiments, activity 603 can be performed similarly or identically to partially or fully harvesting (e.g., removing) the organism(s) from bioreactor 101 (FIG. 1) as described above with respect to system 100 (FIG. 1). In some embodiments, activity 603 can be performed after activity 602 and/or before one or both of activities 604 and 605. In many embodiments, activity 603 can be repeated one or more times, such as, for example, when the first organism(s) reach one or more culture densities as described above with respect to system 100 (FIG. 1).

Figure 9:
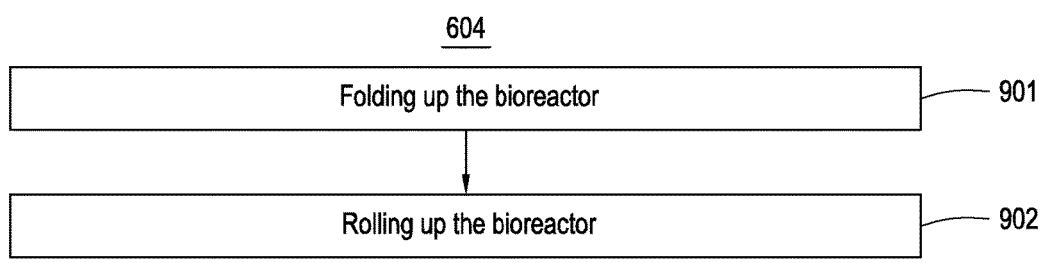
FIG. 9 illustrates a flow chart of an exemplary activity of gathering up the bioreactor, according to the embodiment of FIG. 6.

In many embodiments, method 600 can comprise activity 604 of gathering up the bioreactor (e.g., after removing the organism(s) from the bioreactor). Activity 604 can be performed similarly or identically to gathering up bioreactor 101 (FIG. 1) as described above with respect to system 100 (FIG. 1). In various embodiments, activity 604 can be performed one or more times. For example, activity 604 can be performed before activity 601 (e.g., when activity 601 comprises activity 702) and/or before activity 605. FIG. 9 illustrates a flow chart of an exemplary activity 604, according to the embodiment of FIG. 6.

Activity 604 can comprise activity 901 of folding up the bioreactor (e.g., after removing the first organism(s) from the bioreactor). Further, activity 604 can comprise activity 902 of rolling up the bioreactor (e.g., after removing the first organism(s) from the bioreactor. In some embodiments, only one or both of activity 901 and activity 902 can be performed.

Referring again to FIG. 6, method 600 can comprise activity 605 of resterilizing the bioreactor. Performing activity 605 can be similar or identical to performing activity 702 (FIG. 7).

Further, method 600 can comprise activity 606 of vitally supporting with the bioreactor one or more second organisms with the bioreactor. Performing activity 606 can be similar to performing activity 602 but with respect to the second organism(s). In many embodiments, activity 606 can be performed after activity 605.

Figure 10:
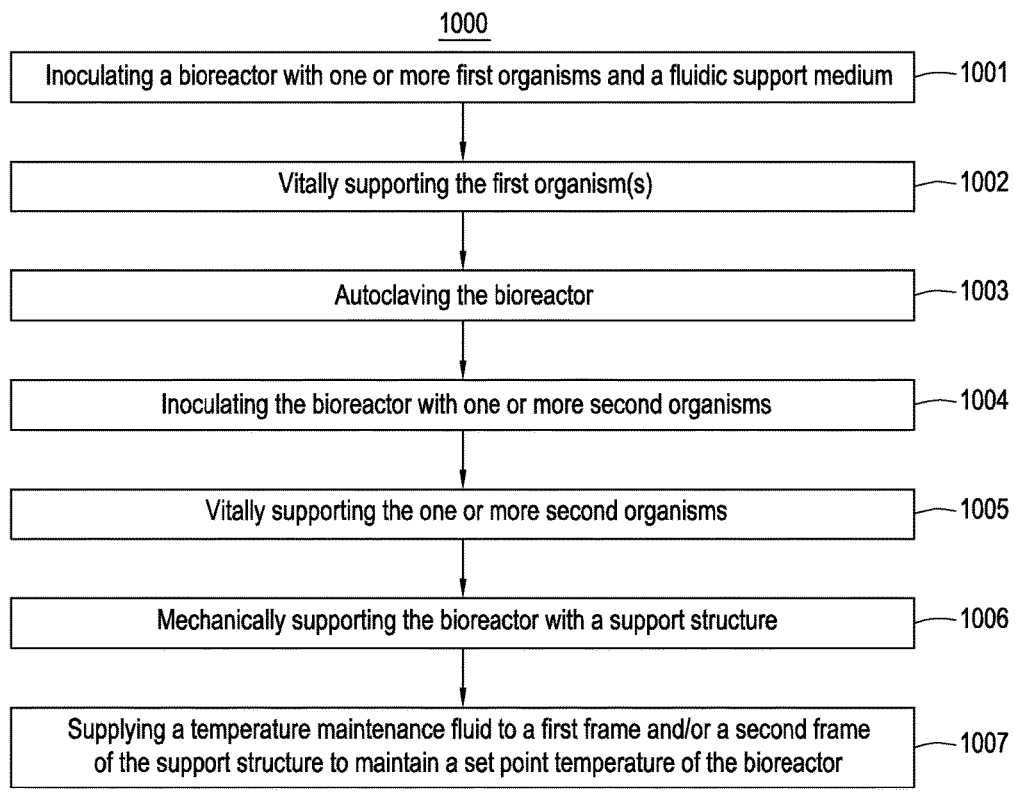
FIG. 10 illustrates a flow chart for an embodiment of a method.

Turning ahead again in the drawings, FIG. 10 illustrates a flow chart for an embodiment of a method 1000. Method 1000 is merely exemplary and is not limited to the embodiments presented herein. Method 1000 can be employed in many different embodiments or examples not specifically depicted or described herein. In some embodiments, the activities of method 1000 can be performed in the order presented. In other embodiments, the activities of method 1000 can be performed in any other suitable order. In still other embodiments, one or more of the activities of method 1000 can be combined or skipped.

In many embodiments, method 1000 can comprise activity 1001 of inoculating a bioreactor with one or more first organisms and a fluidic support medium. In some embodiments, activity 1001 can be performed similarly or identically to inoculating bioreactor 101 with one or more organisms and a fluidic support medium as described above with respect to system 100 (FIG. 1). The bioreactor can be similar or identical to bioreactor 101. Further, the first organism(s) and/or the fluidic support medium can be similar or identical to the organism(s) and/or the fluidic support medium as described above with respect to system 100 (FIG. 1).

In these or other embodiments, method 1000 can comprise activity 1002 of vitally supporting the first organism(s). In many embodiments, performing activity 1002 can be similar or identical to performing activity 602 (FIG. 6). In further embodiments, activity 1002 can be performed after activity 1001. Further, activity 1002 can be performed to achieve the average densities and/or average maximum production rates of the first organism(s) as described above with respect to system 100 (FIG. 1).

Further, method 1000 can comprise activity 1003 of autoclaving the bioreactor. For example, performing activity 1003 can be similar or identical to performing activity 702 (FIG. 7). In many embodiments, activity 1003 can be performed after activity 1001 and/or activity 1002.

In some embodiments, method 1000 can comprise activity 1004 of inoculating the bioreactor with one or more second organisms. The second organism(s) can be similar or identical to the organism(s) described above with respect to system 100 (FIG. 1). In many embodiments, performing activity 1004 can be similar or identical to performing activity 1001. In these or other embodiments, activity 1004 can be performed after activity 1003.

Further, method 1000 can comprise activity 1005 of vitally supporting the one or more second organisms. In many embodiments, performing activity 1005 can be similar or identical to performing activity 1002. In these or other embodiments, activity 1005 can be performed after activity 1004.

In some embodiments, method 1000 can comprise activity 1006 of mechanically supporting the bioreactor with a support structure. The support structure can be similar or identical to support structure 323 (FIG. 3) and/or support structure 423 (FIG. 4). Further, activity 1006 can be performed similarly or identically to mechanically supporting one of bioreactor(s) 324 (FIG. 3) with support structure 323 (FIG. 3) as described above with respect to system 300 (FIG. 3).

In further embodiments, method 1000 can comprise activity 1007 of supplying a temperature maintenance fluid to a first frame and/or a second frame of the support structure to maintain a set point temperature of the bioreactor. The temperature maintenance fluid can be similar or identical to the temperature maintenance fluid described above with respect to system 300 (FIG. 3). Further, the set point temperature can be similar or identical to the set point temperature described above with respect to system 100 (FIG. 1) and/or system 300 (FIG. 3). Meanwhile, the first frame can be similar or identical to first frame 330 (FIG. 3) and/or first frame 430 (FIG. 4); and/or the second frame can be similar or identical to second frame 331 (FIG. 3) and/or second frame 431 (FIG. 4). Activity 1007 can be performed similarly or identically to supplying a temperature maintenance fluid to first frame 330 (FIG. 3) and/or second frame 331 (FIG. 3) of support structure 323 (FIG. 3) to maintain a set point temperature of bioreactor 328 (FIG. 3) as described above with respect to system 300 (FIG. 3) and/or temperature maintenance fluid manifold 343 (FIG. 3). In some embodiments, activity 1006 and/or activity 1007 can be omitted.

Figure 11:
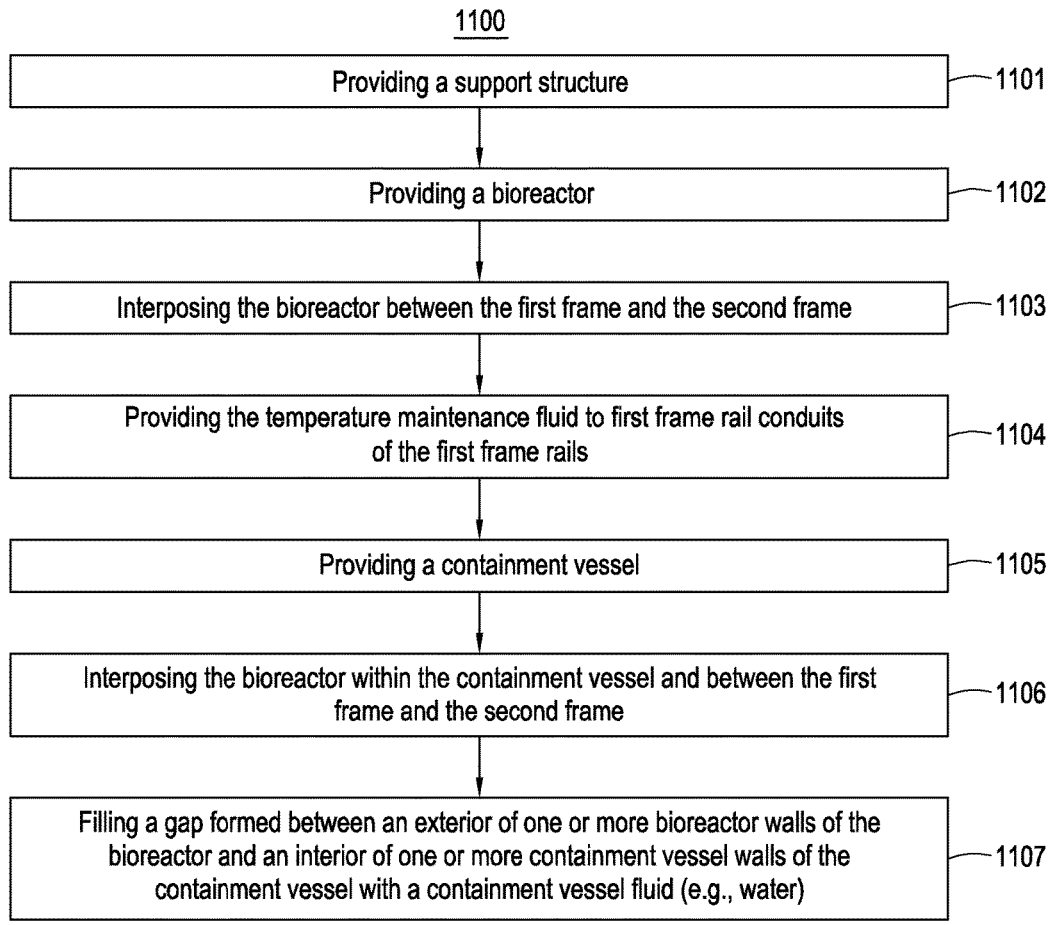
FIG. 11 illustrates a flow chart for an embodiment of a method.

Turning ahead again in the drawings, FIG. 11 illustrates a flow chart for an embodiment of a method 1100. In some embodiments, method 1100 can comprise a method of providing a system. The system can be similar or identical to system 300 (FIG. 3) and/or system 400 (FIG. 4). Method 1100 is merely exemplary and is not limited to the embodiments presented herein. Method 1100 can be employed in many different embodiments or examples not specifically depicted or described herein. In some embodiments, the activities of method 1100 can be performed in the order presented. In other embodiments, the activities of method 1100 can be performed in any other suitable order. In still other embodiments, one or more of the activities of method 1100 can be combined or skipped.

Figure 12:
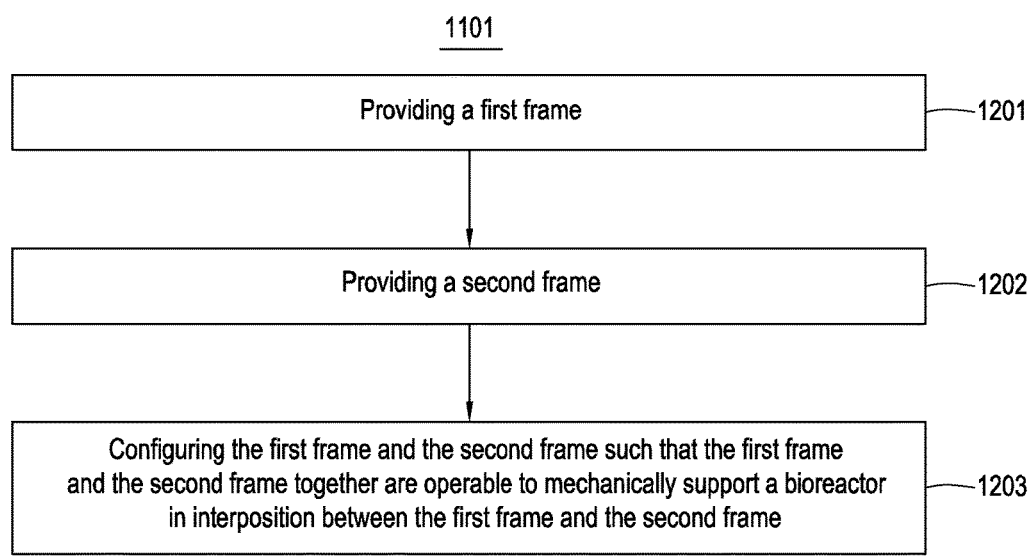
FIG. 12 illustrates a flow chart of an exemplary activity of providing a support structure, according to the embodiment of FIG. 11.

In many embodiments, method 1100 can comprise activity 1101 of providing a support structure. In these embodiments, the support structure can be similar or identical to support structure 323 (FIG. 3) and/or support structure 423 (FIG. 4). FIG. 12 illustrates a flow chart for an exemplary activity 1101, according to the embodiment of FIG. 11.

For example, activity 1101 can comprise activity 1201 of providing a first frame. In these embodiments, the first frame can be similar or identical to first frame 330 (FIG. 3), first frame 430 (FIG. 4), and/or first frame 332 (FIG. 3). For example, performing activity 1201 can comprise providing two or more first frame rails. The first frame rails can be similar or identical to first frame rails 334 (FIG. 3) and/or first frame rails 434 (FIG. 4).

Further, activity 1101 can comprise activity 1202 of providing a second frame. For example, performing activity 1202 can comprise providing two or more second frame rails. The second frame rails can be similar to first frame rails 334 (FIG. 3) and/or first frame rails 434 (FIG. 4) and similar or identical to the second frame rails described above with respect to system 300 (FIG. 3).

In some embodiments, activity 1101 can comprise activity 1203 of configuring the first frame and the second frame such that the first frame and the second frame together are operable to mechanically support a bioreactor in interposition between the first frame and the second frame. For example, performing activity 1203 can comprise orienting the first frame and the second frame vertically and parallel to each other to form a slot in between.

Referring back to FIG. 11, in some embodiments, method 1100 can comprise activity 1102 of providing the bioreactor. The bioreactor can be similar or identical to bioreactor 101 (FIG. 1), bioreactor 200 (FIG. 2), one of bioreactor(s) 324 (FIG. 3), and/or bioreactor 328 (FIG. 3).

Further, method 1100 can comprise activity 1103 of interposing the bioreactor between the first frame and the second frame. For example, performing activity 1103 can comprise lowering the bioreactor into the slot formed between the first frame and the second frame. In some embodiments, activity 1103 can be performed approximately simultaneously with or after activity 1102.

Meanwhile, in some embodiments, method 1100 can comprise activity 1104 of providing the temperature maintenance fluid to first frame rail conduits of the first frame rails. The first frame rail conduits can be similar or identical to the hollow conduits of first frame rails 334 (FIG. 3). In some embodiments, activity 1104 can be omitted.

In some embodiments, method 1100 can comprise activity 1105 of providing a containment vessel. In many embodiments, the containment vessel can be similar or identical to the containment vessel described above with respect to system 100 (FIG. 1).

Further, method 1100 can comprise activity 1106 of interposing the bioreactor within the containment vessel and between the first frame and the second frame. In many embodiments, performing activity 1106 can be similar or identical to interposing the bioreactor within the containment vessel and between the first frame and the second frame as described above with respect to system 100 (FIG. 1).

Further still, method 1100 can comprise activity 1107 of filling a gap formed between an exterior of one or more bioreactor walls of the bioreactor and an interior of one or more containment vessel walls of the containment vessel with a containment vessel fluid (e.g., water). In many embodiments, the containment vessel fluid can be similar or identical to the containment vessel fluid described above with respect to system 100 (FIG. 1). In these or other embodiments, performing activity 1107 can be similar or identical to filling a gap formed between an exterior of one or more bioreactor walls of the bioreactor and an interior of one or more containment vessel walls of the containment vessel with a containment vessel fluid as described above with respect to system 100 (FIG. 1).

Figure 13:
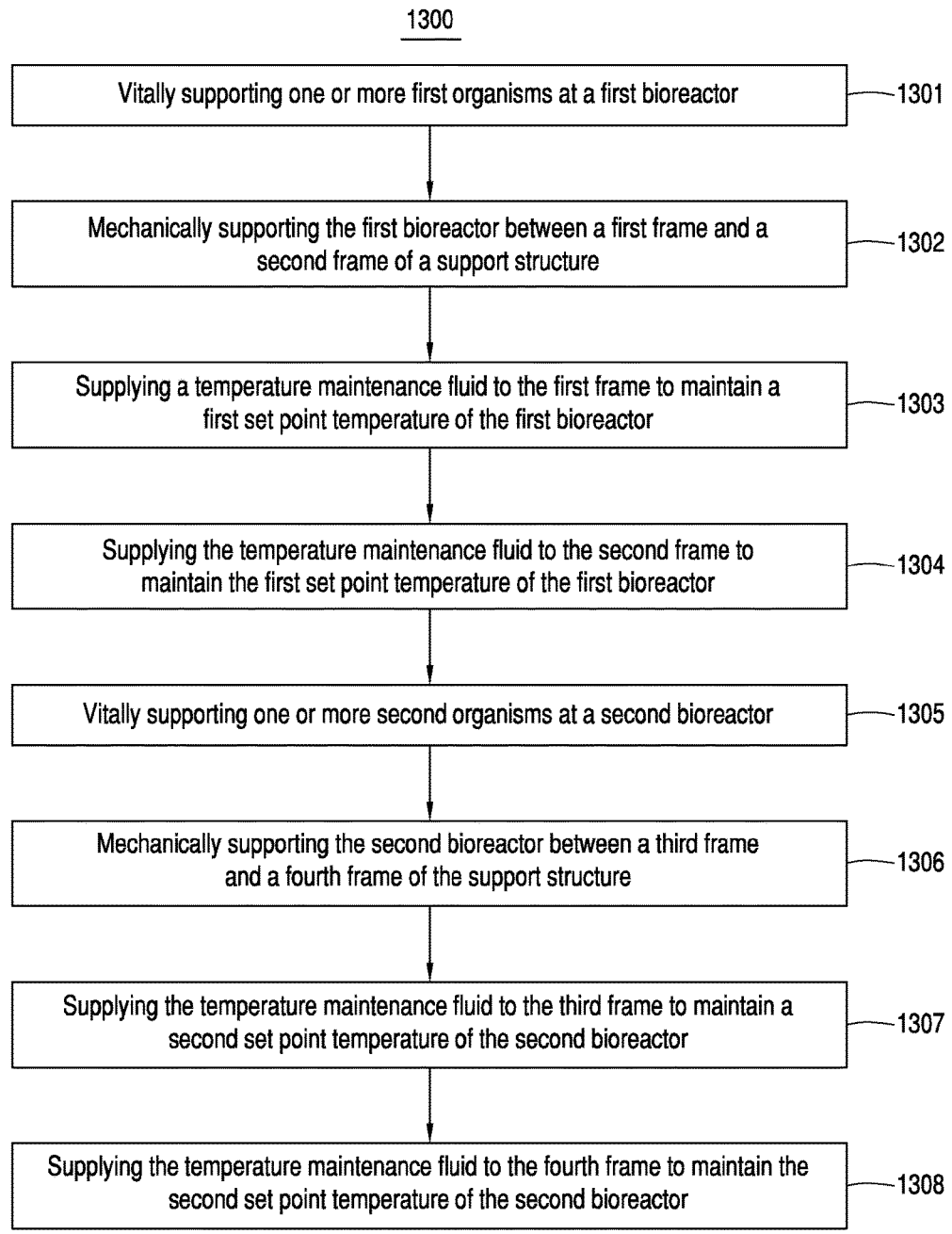
FIG. 13 illustrates a flow chart for an embodiment of a method.

Turning ahead again in the drawings, FIG. 13 illustrates a flow chart for an embodiment of a method 1300. Method 1300 is merely exemplary and is not limited to the embodiments presented herein. Method 1300 can be employed in many different embodiments or examples not specifically depicted or described herein. In some embodiments, the activities of method 1300 can be performed in the order presented. In other embodiments, the activities of method 1300 can be performed in any other suitable order. In still other embodiments, one or more of the activities of method 1300 can be combined or skipped.

In some embodiments, method 1300 can comprise activity 1301 of vitally supporting one or more first organisms at a first bioreactor. The first bioreactor can be similar or identical to bioreactor 101 (FIG. 1), bioreactor 200 (FIG. 2), one or bioreactor(s) 324 (FIG. 3), and/or first bioreactor 328 (FIG. 3). Also, the first organism(s) can be similar or identical to the organism(s) described above with respect to system 100 (FIG. 1).

Further, method 1300 can comprise activity 1302 of mechanically supporting the first bioreactor between a first frame and a second frame of a support structure. In these embodiments, the support structure can be similar or identical to support structure 323 (FIG. 3) and/or support structure 423 (FIG. 4); the first frame can be similar or identical to first frame 330 (FIG. 3) and/or first frame 430 (FIG. 4); and/or the second frame can be similar or identical to first frame 331 (FIG. 3) and/or second frame 431 (FIG. 4).

In some embodiments, method 1300 can comprise activity 1303 of supplying a temperature maintenance fluid to the first frame to maintain a first set point temperature of the first bioreactor. The temperature maintenance fluid and the first set point temperature can be similar or identical to the temperature maintenance fluid and the set point temperature described above with respect to system 300 (FIG. 3). In some embodiments, activity 1303 can be omitted.

In further embodiments, method 1300 can comprise activity 1304 of supplying the temperature maintenance fluid to the second frame to maintain the first set point temperature of the first bioreactor. In some embodiments, activity 1304 can be omitted.

Meanwhile, in many embodiments, method 1300 can comprise activity 1305 of vitally supporting one or more second organisms at a second bioreactor. The first bioreactor can be similar or identical to bioreactor 101 (FIG. 1), bioreactor 200 (FIG. 2), one or bioreactor(s) 324 (FIG. 3), and/or second bioreactor 329 (FIG. 3). Also, the second organism(s) can be similar or identical to the organism(s) described above with respect to system 100 (FIG. 1).

Further, method 1300 can comprise activity 1306 of mechanically supporting the second bioreactor between a third frame and a fourth frame of the support structure. In these embodiments, the third frame can be similar or identical to first frame 332 (FIG. 3) and/or first frame 432 (FIG. 4); and/or the fourth frame can be similar or identical to first frame 333 (FIG. 3) and/or second frame 431 (FIG. 4). In some embodiments, method 1300 can comprise activity 1307 of supplying the temperature maintenance fluid to the third frame to maintain a second set point temperature of the second bioreactor. The second set point temperature can be similar or identical to the set point temperature described above with respect to system 300 (FIG. 3). In some embodiments, activity 1307 can be omitted.

In further embodiments, method 1300 can comprise activity 1308 of supplying the temperature maintenance fluid to the fourth frame to maintain the second set point temperature of the second bioreactor. In some embodiments activity 1308 can be omitted.

Meanwhile, in many embodiments, two or more of activities 1301-1308 can be performed approximately simultaneously with each other.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that one or more of the activities of method 500 (FIG. 5), method 600 (FIG. 6), method 1000 (FIG. 10), method 1100 (FIG. 11), and/or method 1300 (FIG. 13) may be comprised of many different activities, be performed by many different modules, and in many different orders, that any element of FIGS. 1-15 may be modified, and that the foregoing discussion of certain of these embodiments does not necessarily represent a complete description of all possible embodiments.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system comprising:
    a support structure configured to mechanically support a first bioreactor, the support structure comprising:
        a first frame; and
        a second frame, together with the first frame, being configured to mechanically support the first bioreactor in interposition between the first frame and the second frame;
    wherein:
        the first frame is configured to maintain a first set point temperature of the first bioreactor through an exchange of thermal energy between the first frame and the first bioreactor when the first bioreactor is vitally supporting one or more first microorganisms and when the support structure is mechanically supporting the first bioreactor; and
        the second frame is configured to maintain the first set point temperature of the first bioreactor through an exchange of thermal energy between the second frame and the first bioreactor when the first bioreactor is vitally supporting the one or more first microorganisms and when the support structure is mechanically supporting the first bioreactor;
        the first bioreactor comprises:
            a first bioreactor cavity configured to contain the one or more first microorganisms and a first fluidic support medium; and
            one or more first bioreactor walls at least partially enclosing the first bioreactor cavity, the one or more first bioreactor walls comprising at least one first bioreactor wall material and the at least one first bioreactor wall material being flexible;
        the first frame comprises two or more discrete first frame rails, each first frame rail of the two or more first frame rails comprising a first frame rail conduit, wherein each first frame rail is vertical and parallel with the other first frame rails;
        each first frame rail conduit of the two or more first frame rail conduits containing a temperature maintenance fluid configured to exchange thermal energy between the first bioreactor and the temperature maintenance fluid as it flows in an upward direction through each first frame rail conduit in order to maintain the first set point temperature of the first bioreactor when the first bioreactor is vitally supporting the one or more first microorganisms; and
        the two or more first frame rails are operable to simultaneously mechanically support the first bioreactor and exchange thermal energy between the first bioreactor and the temperature maintenance fluid contained in the two or more first frame rail conduits;
        the second frame of the support structure comprises two or more discrete second frame rails, each second frame rail of the two or more second frame rails comprising a second frame rail conduit, wherein each second frame rail is vertical and parallel with the other second frame rails;
        each second frame rail conduit of the two or more second frame rail conduits containing the temperature maintenance fluid configured to exchange thermal energy between the first bioreactor and the temperature maintenance fluid as it flows in an upward direction through each second frame rail conduit in order to maintain the first set point temperature of the first bioreactor when the first bioreactor is vitally supporting the one or more first microorganisms;
        a floor gap disposed beneath at least one of the first frame and the second frame between a floor and a lowest horizontal member of the at least one of the first frame and the second frame; and
        at least part of the one or more first bioreactor walls of the first bioreactor bulges to dispose at least part of the one or more first bioreactor walls into the floor gap when the support structure is mechanically supporting the first bioreactor.

2. The system of claim 1 wherein:
    the first bioreactor further comprises:
        one or more bioreactor fittings in communication with the first bioreactor cavity, the one or more bioreactor fittings comprising at least one gas delivery fitting;
        one or more gas delivery devices located within the first bioreactor cavity, the one or more gas delivery devices being operable to inject gas into the first bioreactor cavity to mix the one or more first microorganisms; and
        one or more flexible tubes located within the first bioreactor cavity, the one or more flexible tubes comprising at least one gas delivery tube coupling the one or more gas delivery devices to the at least one gas delivery fitting.

3. The system of claim 2 wherein:
    the two or more first frame rails and the two or more second frame rails are configured to receive the temperature maintenance fluid from only a single source of the temperature maintenance fluid in parallel in order to reduce a total path length of the temperature maintenance fluid upwardly through the two or more vertical first frame rails and through the two or more vertical second frame rails and in order to minimize temperature fluctuation.

4. The system of claim 1 wherein:
    the support structure further comprises one or more adjustable coupling mechanisms coupling the first frame to the second frame; and
    the second frame is configured to selectively move relative to the first frame in a direction orthogonal to the first frame when the one or more adjustable coupling mechanisms are adjusted.

5. The system of claim 2 further comprising:
    at least one light source mechanically supported by the support structure and operable to illuminate the one or more first microorganisms when the first bioreactor is vitally supporting the one or more first microorganisms and when the support structure is mechanically supporting the first bioreactor.

6. The system of claim 5 wherein:
    the support structure is further configured to mechanically support a second bioreactor;
    the support structure comprises a third frame and a fourth frame together being configured to mechanically support the second bioreactor in interposition between the third frame and the fourth frame, the third frame further being configured to maintain a second set point temperature of the second bioreactor through an exchange of thermal energy between the third frame and the second bioreactor when the second bioreactor is vitally supporting one or more second microorganisms and when the support structure is mechanically supporting the second bioreactor;

and
the second bioreactor comprises:
  a second bioreactor cavity configured to contain the one or more second microorganisms and a second fluidic support medium; and
  one or more second bioreactor walls at least partially enclosing the second bioreactor cavity, the one or more second bioreactor walls comprising at least one second bioreactor wall material and the at least one second bioreactor wall material being flexible.

* * * * *